(12) United States Patent
Milbodker et al.

(10) Patent No.: US 7,632,294 B2
(45) Date of Patent: Dec. 15, 2009

(54) DEVICES AND METHODS FOR SPINE REPAIR

(75) Inventors: Michael T Milbodker, Holliston, MA (US); Jeffrey A Wilson, Wrentham, MA (US); Robert M Arcangeli, Westborough, MA (US)

(73) Assignee: Promethean Surgical Devices, LLC, Woburn, MA (US)

( * ) Notice: Subject to any disclaimer, the term of this patent is extended or adjusted under 35 U.S.C. 154(b) by 0 days.

(21) Appl. No.: 10/873,899

(22) Filed: Jun. 22, 2004

(65) Prior Publication Data

US 2005/0070913 A1    Mar. 31, 2005

Related U.S. Application Data

(60) Provisional application No. 60/483,186, filed on Sep. 29, 2003, provisional application No. 60/483,260, filed on Nov. 17, 2003, provisional application No. 60/516,999, filed on Nov. 4, 2003.

(51) Int. Cl.
*A61B 17/88* (2006.01)
*A61B 17/58* (2006.01)
*A61F 2/44* (2006.01)

(52) U.S. Cl. .............. 606/279; 606/92; 606/93; 606/94; 623/17.11; 623/17.12; 623/17.16; 623/23.58

(58) Field of Classification Search ............. 623/17.16, 623/17.11, 17.12, 23.58; 606/92, 93, 94, 606/279
See application file for complete search history.

(56) References Cited

U.S. PATENT DOCUMENTS 3,867,728 A    2/1975    Stubstad
4,204,531 A    5/1980    Aginsky
4,309,777 A    1/1982    Patil
4,313,434 A    2/1982    Segal
4,349,921 A    9/1982    Kuntz
4,501,269 A    2/1985    Bagby
4,545,374 A    10/1985    Jacobson
4,554,914 A    11/1985    Kapp et al.

(Continued)

FOREIGN PATENT DOCUMENTS

CA    2 423 952 A1 *    4/2002

(Continued)

OTHER PUBLICATIONS

"Biomechanical efficiency of a Protein Polymer for Intervertebral Nucleus Augmentation and Replacement", World Cong. Biomech 2002.

(Continued)

*Primary Examiner*—David H Willse
*Assistant Examiner*—Javier G Blanco
(74) *Attorney, Agent, or Firm*—Rissman Hendricks & Oliverio

(57) ABSTRACT

Surgical methods of repairing defects and deficiencies in the spine are disclosed. The methods involve delivering a single part in-situ polymerizing fluid to (i) close a weakened segment or fissure in the annulus fibrosus, (ii) strengthen the annulus, (iii) replace or augment the disc nucleus, or (iv) localize a disc prosthesis. The methods may include placing a delivery conduit adjacent to the repair site and providing a liquid tissue adhesive to bond to and repair a disc defect or deficiency.

30 Claims, 18 Drawing Sheets

U.S. PATENT DOCUMENTS

| | | |
|---|---|---|
| 4,573,448 A | 3/1986 | Kambin |
| 4,636,217 A | 1/1987 | Ogilvie et al. |
| 4,759,766 A | 7/1988 | Buettner-Janz et al. |
| 4,772,287 A | 9/1988 | Ray et al. |
| 4,815,453 A | 3/1989 | Cotrel |
| 4,904,260 A | 2/1990 | Ray et al. |
| RE33,258 E | 7/1990 | Onik et al. |
| 4,946,458 A | 8/1990 | Harms et al. |
| 4,966,953 A | 10/1990 | Shikinami et al. |
| 4,997,432 A | 3/1991 | Keller |
| 5,005,562 A | 4/1991 | Cotrel |
| 5,015,247 A | 5/1991 | Michelson |
| 5,092,867 A | 3/1992 | Harms et al. |
| 5,192,326 A | 3/1993 | Bao et al. |
| 5,195,541 A | 3/1993 | Obenchain |
| 5,196,013 A | 3/1993 | Harms et al. |
| 5,197,971 A | 3/1993 | Bonutti |
| 5,207,678 A | 5/1993 | Harms et al. |
| 5,285,795 A | 2/1994 | Ryan et al. |
| 5,313,962 A | 5/1994 | Obenchain |
| 5,314,477 A | 5/1994 | Marnay |
| 5,423,850 A | 6/1995 | Berger |
| 5,430,072 A | 7/1995 | Muller et al. |
| 5,439,464 A | 8/1995 | Shapiro |
| 5,443,467 A | 8/1995 | Biedermann et al. |
| 5,468,804 A | 11/1995 | Schmalsteig et al. |
| 5,474,555 A | 12/1995 | Puno et al. |
| 5,480,400 A | 1/1996 | Berger |
| 5,489,308 A | 2/1996 | Kuslich |
| 5,514,153 A | 5/1996 | Bonutti |
| 5,520,690 A | 5/1996 | Errico et al. |
| 5,531,746 A | 7/1996 | Errico et al. |
| 5,549,608 A | 8/1996 | Errico et al. |
| 5,549,679 A | 8/1996 | Kuslich |
| 5,554,157 A | 9/1996 | Errico et al. |
| 5,562,736 A | 10/1996 | Ray et al. |
| 5,591,165 A | 1/1997 | Jackson |
| 5,607,426 A | 3/1997 | Ralph et al. |
| 5,624,442 A | 4/1997 | Mellinger et al. |
| 5,643,265 A | 7/1997 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,697,889 A | 12/1997 | Slotman et al. |
| 5,700,291 A | 12/1997 | Kuslich et al. |
| 5,733,286 A | 3/1998 | Errico et al. |
| 5,755,732 A | 5/1998 | Green et al. |
| 5,772,661 A | 6/1998 | Michelson |
| 5,797,909 A | 8/1998 | Michelson |
| 5,797,911 A | 8/1998 | Sherman et al. |
| 5,816,257 A | 10/1998 | Chin |
| 5,817,094 A | 10/1998 | Errico et al. |
| 5,817,303 A | 10/1998 | Stedronsky et al. |
| 5,821,275 A | 10/1998 | Madan et al. |
| 5,824,093 A | 10/1998 | Ray et al. |
| 5,876,402 A | 3/1999 | Errico et al. |
| 5,879,350 A | 3/1999 | Sherman et al. |
| 5,885,286 A | 3/1999 | Sherman et al. |
| 5,891,145 A | 4/1999 | Morrison et al. |
| 5,910,142 A | 6/1999 | Tatar |
| 5,928,242 A | 7/1999 | Kuslich et al. |
| 6,004,326 A | 12/1999 | Castro et al. |
| 6,022,376 A | 2/2000 | Assell et al. |
| 6,033,654 A | 3/2000 | Stedronsky et al. |
| 6,042,582 A | 3/2000 | Ray |
| 6,090,111 A | 7/2000 | Nichols |
| 6,127,597 A | 10/2000 | Beyar et al. |
| 6,132,465 A | 10/2000 | Ray et al. |
| 6,226,548 B1 | 5/2001 | Foley et al. |
| 6,261,287 B1 | 7/2001 | Metz-Stavenhagen |
| 6,264,659 B1 | 7/2001 | Ross et al. |
| 6,273,914 B1 | 8/2001 | Papas |
| 6,287,343 B1 | 9/2001 | Kuslich et al. |
| 6,306,177 B1 | 10/2001 | Felt et al. |
| 6,309,420 B1 | 10/2001 | Preissman |
| 6,315,797 B1 | 11/2001 | Middleton |
| 6,332,894 B1 | 12/2001 | Stalcup et al. |
| 6,376,698 B1 | 4/2002 | Bleys |
| 6,402,784 B1 | 6/2002 | Wardlaw |
| 6,416,465 B2 | 7/2002 | Brau |
| 6,419,706 B1 | 7/2002 | Graf |
| 6,423,333 B1 | 7/2002 | Stedronsky et al. |
| 6,425,919 B1 | 7/2002 | Lambrecht |
| 6,428,576 B1 * | 8/2002 | Haldimann .............. 623/17.16 |
| 6,482,235 B1 | 11/2002 | Lambrecht et al. |
| 6,508,839 B1 | 1/2003 | Lambrecht et al. |
| 6,533,817 B1 | 3/2003 | Norton et al. |
| 6,533,818 B1 | 3/2003 | Weber et al. |
| 6,565,565 B1 | 5/2003 | Yuan et al. |
| 6,569,442 B2 | 5/2003 | Gan et al. |
| 6,592,625 B2 | 7/2003 | Cauthen |
| 6,602,291 B1 | 8/2003 | Ray et al. |
| 6,630,050 B1 | 10/2003 | Moeller et al. |
| 6,726,721 B2 | 4/2004 | Stoy et al. |
| 6,764,514 B1 | 7/2004 | Li et al. |
| 6,805,715 B2 | 10/2004 | Reuter et al. |
| 6,818,018 B1 | 11/2004 | Sawhney |
| 6,821,276 B2 | 11/2004 | Lambrecht et al. |
| 6,883,520 B2 | 4/2005 | Lambrecht et al. |
| 7,223,227 B2 * | 5/2007 | Pflueger ..................... 600/12 |
| 2002/0077701 A1 | 6/2002 | Kuslich |
| 2002/0095154 A1 * | 7/2002 | Atkinson et al. .............. 606/61 |
| 2002/0156531 A1 | 10/2002 | Felt et al. |
| 2003/0028251 A1 * | 2/2003 | Mathews ................. 623/17.16 |
| 2003/0050644 A1 | 3/2003 | Boucher et al. |
| 2003/0050702 A1 | 3/2003 | Berger |
| 2003/0083642 A1 | 5/2003 | Boyd et al. |
| 2003/0125737 A1 | 7/2003 | Hammerslag |
| 2003/0135238 A1 | 7/2003 | Milbocker |
| 2004/0170597 A1 | 9/2004 | Beckman et al. |
| 2005/0129733 A1 | 6/2005 | Milbocker et al. |
| 2005/0182418 A1 | 8/2005 | Boyd et al. |

FOREIGN PATENT DOCUMENTS

| | | |
|---|---|---|
| FR | 2639823 | 12/1988 |
| WO | WO 01/32100 A2 | 5/2001 |

OTHER PUBLICATIONS

Injectable Biomaterials for Augmentation of the Nucleus Pulposus Kitchell & Cappello; Spine Orthplasty Soc. Global Symp., May 1, 2003.

Injectable Biomaterials for Augmentation of the Nucleus Pulposus Boyd, Mahar & Cappello; loc. Pub, not marked; prob. 2003.

* cited by examiner

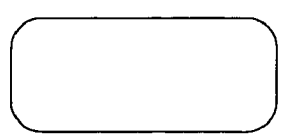
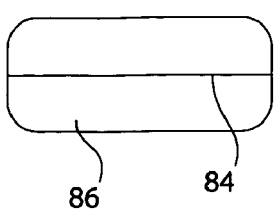
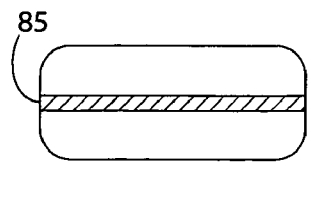
Fig. 9A   Fig. 9B   Fig. 9C
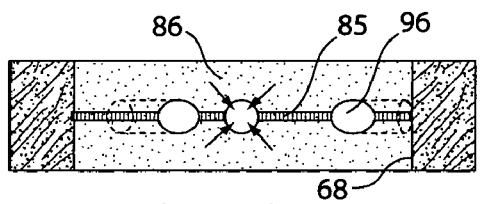
Fig. 9D
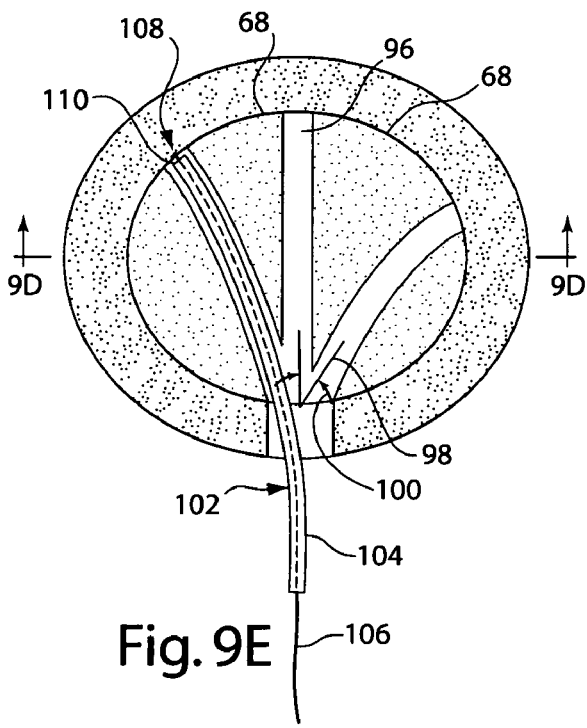
Fig. 9E
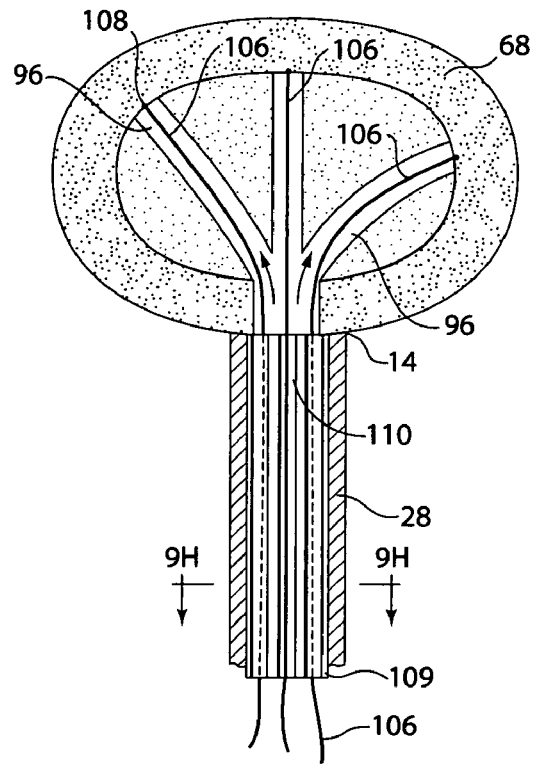
Fig. 9F
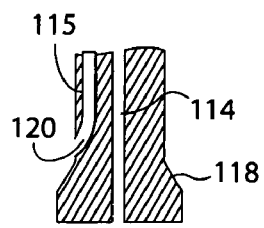
Fig. 9G
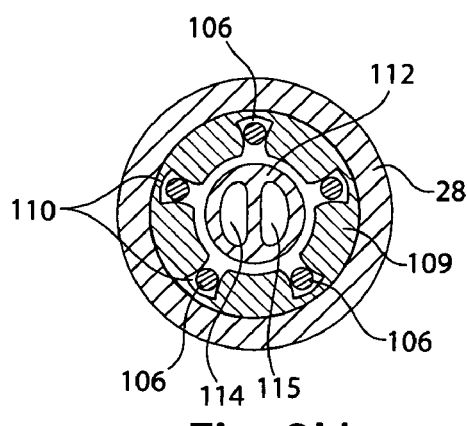
Fig. 9H

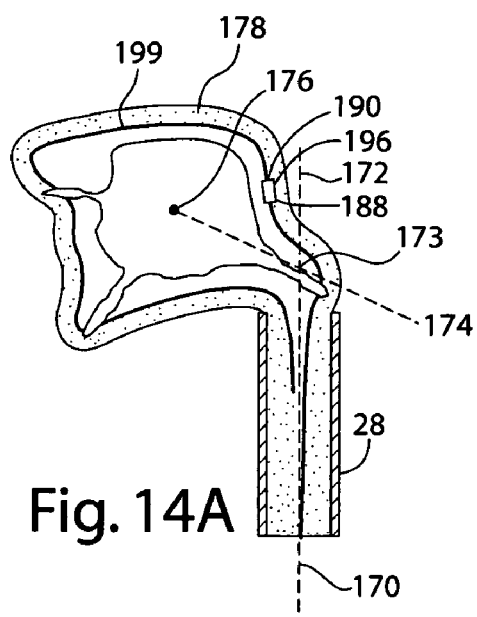
Fig. 14A
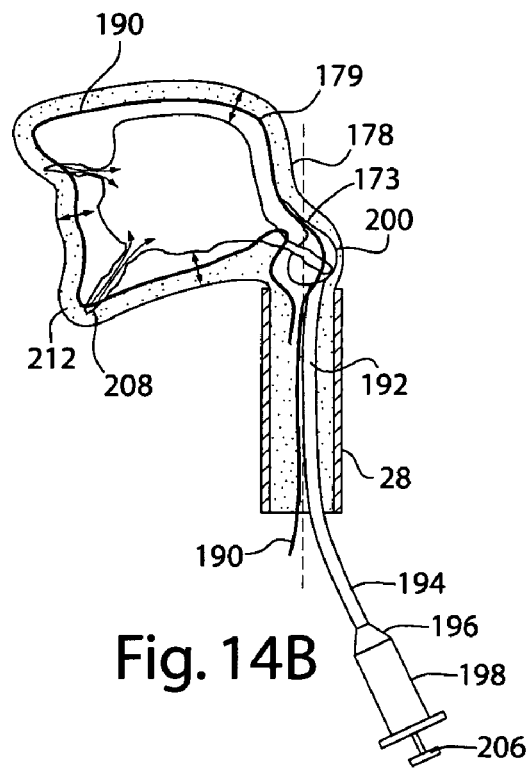
Fig. 14B
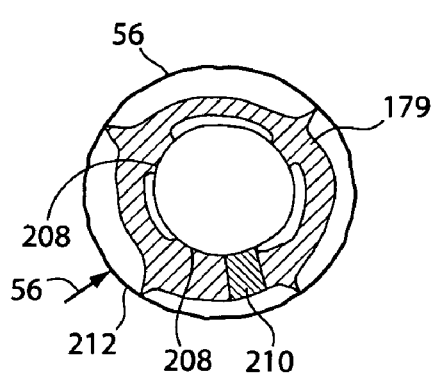
Fig. 14C
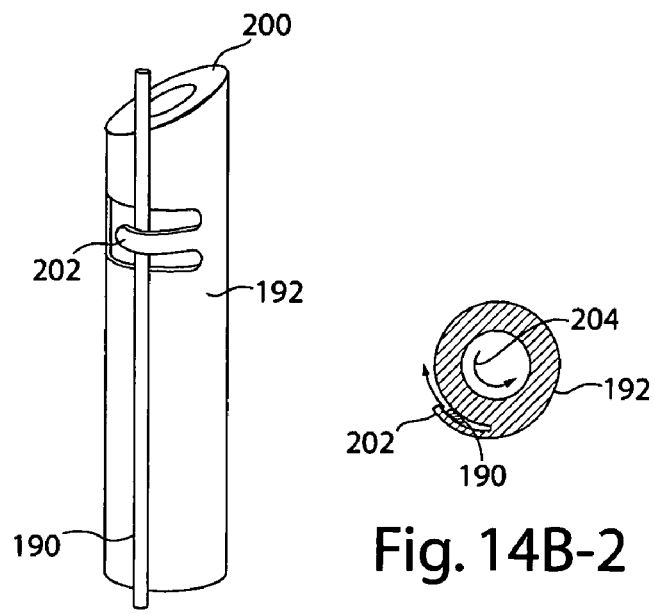
Fig. 14B-1
Fig. 14B-2

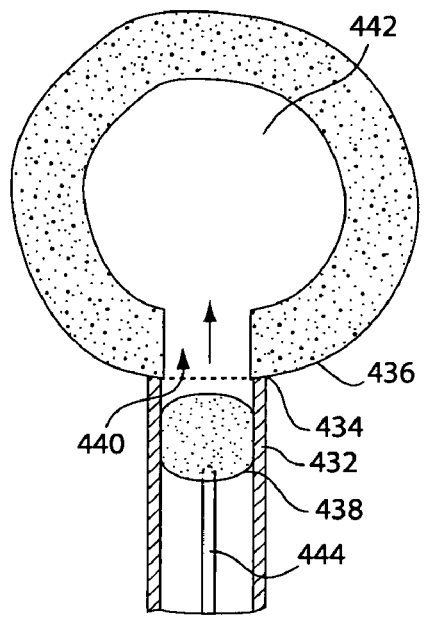
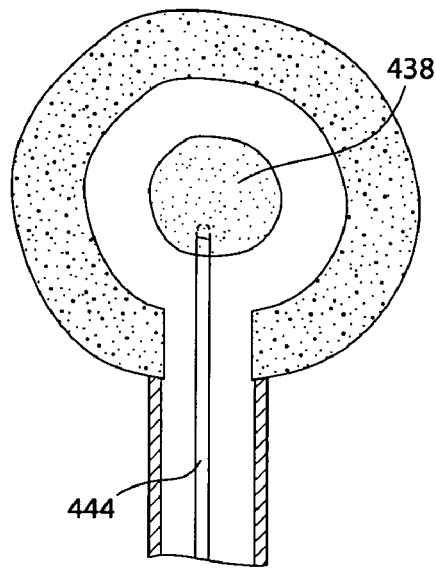
Fig. 19a　　　　Fig. 19b
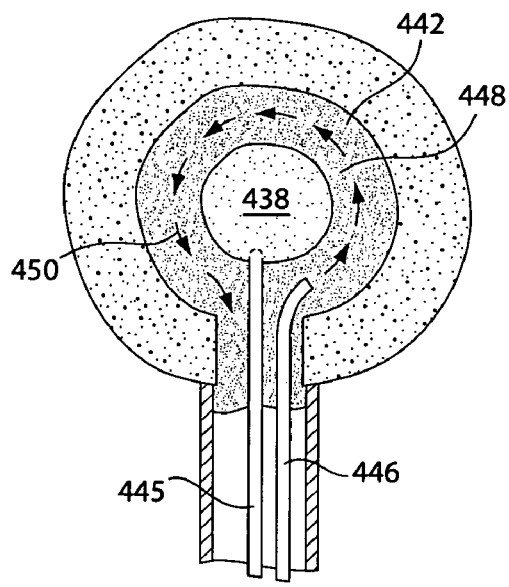
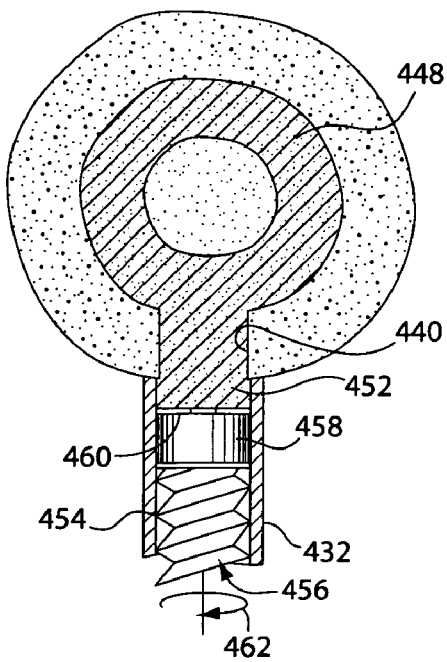
Fig. 19c　　　　Fig. 19d

DEVICES AND METHODS FOR SPINE REPAIR

This application claims the benefit of the priority of U.S. Provisional applications 60/483,186, having an official filing date of Sep. 29, 2003, and 60/516,999, filed Nov. 4, 2003, and 60/483,260, having an official filing date of Nov. 17, 2003, which are hereby incorporated in their entirety by reference.

TECHNICAL FIELD

This disclosure relates to methods and devices for modifying intervertebral disc tissue, spaces, and structure. More particularly, the methods disclosed relate to the treatment of weakening or rents of the annulus, disc nucleus insufficiency, and localization of disc prosthetics, using open and minimally invasive techniques. The preferred compositions for effecting repair are single-part, in-situ polymerizing self-curing adhesive compositions.

BACKGROUND

A. Treatment of Spinal Disc Abnormalities

Intervertebral disc abnormalities are common in the population and cause considerable pain, particularly if they affect adjacent nerves. Disc abnormalities result from trauma, wear, metabolic disorders and the aging process and include degenerative discs, localized tears or fissures in the annulus fibrosus, localized disc herniations with contained or escaped extrusions, and chronic, circumferential bulging discs. Disc fissures occur as a degeneration of fibrous components of the annulus fibrosus. Rather minor activities such as sneezing, bending or simple attrition can tear degenerated annulus fibers and create a fissure. The fissures may be further complicated by extrusion of nucleus pulposus material into or beyond the annulus fibrosus. Difficulties can still present even when there is no visible extrusion, due to biochemicals within the disc irritating surrounding structures and nerves. Initial treatment includes bed rest, pain killers and muscle relaxants, but these measures rarely correct the underlying cause. Surgical treatments include reduction of pressure on the annulus by removing some of the interior nucleus pulposus material by percutaneous nucleotomy. Surgical treatments meant to cure the underlying cause include spinal fusion with screws, rods and fusion cages. Devices and procedures involving screws, rods and plates are disclosed in the following U.S. patents, as well as others: Errico U.S. Pat. Nos. 37,665; 5,733,286; 5,549,608; 5,554,157; 5,876,402; 5,817,094; 5,690,630; 5,669,911; 5,647,873; 5,643,265; 5,607,426; 5,531,746 and 5,520,690; Metz-Stavenhagen U.S. Pat. No. 6,261,287; Puno U.S. Pat. No. 5,474,555; Byrd U.S. Pat. No. 5,446,237; Biedermann U.S. Pat. Nos. 5,672,176 and 5,443,467; Cotrel U.S. Pat. Nos. 4,815,453 and 5,005,562; Jackson U.S. Pat. No. 5,591,165; Harms U.S. Pat. Nos. 4,946,458; 5,092,867; 5,207,678 and 5,196,013; Mellinger U.S. Pat. No. 5,624,442; Sherman U.S. Pat. Nos. 5,885,286; 5,797,911 and 5,879,350; Morrison U.S. Pat. No. 5,891,145; Tatar U.S. Pat. No. 5,910,142; Nicholas U.S. Pat. No. 6,090,111; and Yuan U.S. Pat. No. 6,565,565. Fusion cages and related procedures are disclosed in Bagby U.S. Pat. No. 4,501,269; Michelson U.S. Pat. Nos. 5,015,247 and 5,797,909; Ray U.S. Pat. No. 6,042,582 and Kuslich U.S. Pat. Nos. 5,489,308; 6,287,343 and 5,700,291. Proposed disc replacement devices are disclosed in the following U.S. patents: Middleton U.S. Pat. No. 6,315,797; Marnay U.S. Pat. No. 5,314,477; Stubstad U.S. Pat. No. 3,867,728; Keller U.S. Pat. No. 4,997,432; and Buettner-Janz U.S. Pat. No. 4,759,766.

A contained disc herniation is not associated with free nucleus fragments migrating to the spinal canal. However, a contained disc herniation can still protrude and irritate surrounding structures, for example by applying pressure to spinal nerves. Escaped nucleus pulposus can chemically irritate neural structures. Current treatment methods include reduction of pressure on the annulus by removing some of the interior nucleus pulposus material by percutaneous nucleotomy. See, for example, Kambin U.S. Pat. No. 4,573,448. Complications include disc space infection, nerve root injury, hematoma formation, instability of the adjacent vertebrae and collapse of the disc from decrease in height. It has been proposed to treat weakening due to nucleus pulposus deficiency by inserting preformed hydrogel implants. See, Ray U.S. Pat. Nos. 4,772,287; 4,904,260 and, 5,562,736 and Bao U.S. Pat. No. 5,192,326.

Circumferential bulging of the disc also can result in chronic disc weakening. The joint can become mechanically less stable. As the bulging disc extends beyond its normal circumference, the disc height is compromised and nerve roots are compressed. In some cases osteophytes form on the outer surface of the disc and further encroach on the spinal canal and channels through which nerves pass. The condition is known as lumbar spondylosis. Continued disc degeneration can resulting in one vertebral body segment approaching and possibly contacting an adjacent vertebral body segment.

Treatment for segmental instability include bed rest, pain medication, physical therapy and steroid injection. Spinal fusion is the final therapy performed with or without discectomy. Other treatment includes discectomy alone or disc decompression with or without fusion. Nucleotomy can be performed by removing some of the nucleus matter to reduce pressure on the annulus. Complications include disc space infection, nerve root injury, hematoma formation, and instability of adjacent vertebrae. New fixation devices include pedicle screws and interbody fusion cages. Studies on fixation show success rates between 50% and 67% for pain improvement, and a significant number of patients have more pain postoperatively.

Delivery of tissue adhesives to the spine in a minimally invasive manner have been disclosed, and include procedures for restoring structural integrity to vertebral bodies. See Scribner U.S. Pat. Nos. 6,241,734 and 6,280,456; Reiley U.S. Pat. Nos. 6,248,110 and 6,235,043; Boucher U.S. Pat. No. 6,607,554 and Bhatnagar U.S. Pat. No. 6,395,007. Methods of repairing the spinal disc or portions thereof are disclosed in Cauthern U.S. Pat. No. 6,592,625, Haldimann U.S. Pat. No. 6,428,576, Trieu U.S. Pat. No. 6,620,196 and Milner U.S. Pat. No. 6,187,048.

B. Surgical Approaches to the Spine

The spine may be approached in open surgery using posterior, anterior or lateral approaches. The following is a brief description of several proposed surgical approaches which may be used to gain access to the spine in a less invasive manner to treat spinal insufficiency.

Posterior Lateral Approach Methods for disc access include laminectomy, a procedure wherein a channel is made from the dorsal side of the patient's back to the lumbar lamina of the disc. Blood vessels, ligaments, major back support muscles and spinal nerves located around the dural sac are retracted. Once the channel has been cleared, the standard procedure is to cut a hole in the disc capsule and pass instruments into the disc interior. This approach creates a defect that is oriented toward spinal nerves, thus typically the nucleus is completely removed to prevent extrusion of nuclear material and subsequent pressure on these nerves. Alternatively, under visual magnification with an operating microscope or operating loupe, small diameter microsurgical instruments can access the disc without cutting bone. It is possible to bypass the nerves and blood vessels entirely by inserting a cannula through the patient's side above the pelvic crest to reach a predetermined position along the lumbar portion of the spine. This procedure can be guided with use of fluoroscopy.

Kambin U.S. Pat. No. 4,573,448 describes a posterior lateral approach performed under local anesthesia by the insertion of a cannulated trocar over a guide wire extending through the patient's back toward a target disc at an angle of approximately 35 degrees with respect to the patient's perpendicular line. In particular, a hollow needle with a stylet is inserted at a location spaced from the midline so as to form a 35 degree angle in an oblique direction. When the needle reaches the annulus fibrosis it is withdrawn after a guide wire is introduced through the needle to the disc. A cannulated, blunt-tipped trocar is passed over the guide wire until the tip reaches the annulus. The guide wire is withdrawn. A closely-fitting, thin-walled cannula is passed over the trocar until it reaches the annulus. The trocar can be withdrawn. Cutting instruments or a punch can be used to expose the nucleus.

Paramedian Transabdominal Procedure In this procedure the patient is in the supine or lithotomy position. This transabdominal procedure involves splitting the paramedian rectus, retracting the bowel, incising the peritoneum on the posterior wall of the abdominal cavity and accessing the anterior spine. Alternatively, the anterior rectus sheath is exposed of the left rectus muscle. The anterior rectus sheath is incised to expose the body of the rectus muscle. The rectus muscle is then mobilized over an adequate length, preferably symmetrical with the incision, and the rectus is retracted medially. The posterior rectus sheath is cut to expose the peritoneum. The peritoneum is pushed aside and dissected to expose the psoas muscle. The ureter and the left iliac vessels are mobilized. The rectus muscle, ureter, iliac vessels, and peritoneum are retracted laterally to expose the lumbar region. For repair to lumbar vertebrae L3-4 and L4-5, access should be made to the left of the aorta and inferior vena cava, between the aorta and the psoas muscle, and through the posterior peritoneum and fatty tissue. In some cases it may be necessary to transverse the psoas muscle. For access to sites between L5 and S-1, the dissection is closer to the midline between the iliac branches of the great vessels.

Lateral Retroperitoneal Procedure The retroperitoneal procedure involves placing the patient in the right lateral recumbent position and making an incision in the abdomen at the border of the rectus muscle and subsequent dissection down to identify the peritoneum. Dissection can be performed bluntly or may be facilitated using a balloon cannula or expanding cannula as described by Bonutti (U.S. Pat. No. 5,514,153). The resulting retroperitoneal cavity can be held open with a retractor positioned to elevate the wall of the cavity adjacent to the patient's left side. The retractor may be a balloon retractor, see for example Moll U.S. Pat. No. 5,309,896 and Bonutti U.S. Pat. Nos. 5,331,975; 5,163,949; 6,277,136; 6,171,236; and 5,888,196. The peritoneum is dissected away from the abdominal wall in first a lateral and then a posterior direction until the spine is exposed. Under endoscopic visualization the iliopsoas muscle is dissected or retracted to facilitate disc repair.

Alternatively, dissection of the peritoneum can be accomplished using gas pressure into the preperitoneal and retroperitoneal space, thereby expanding the space and dissecting the peritoneal lining from the abdominal wall while relocating the peritoneal lining toward the midline of the abdomen. Access devices that may be used to gain minimally invasive access to the spine in several of the foregoing surgical approaches to the spine include expanding cannula structures such as Dubrul U.S. Pat. Nos. 5,183,464 and 5,431,676, Bonutti U.S. Pat. Nos. 5,674,240 and 5,320,611, and Davison U.S. Pat. Nos. 6,652,553 and 6,187,000.

Laparoscopic Approach It is also known to approach the lumbar spine anteriorly using a laparoscopic approach. See, for example, Green U.S. Pat. Nos. 5,755,732 and 5,620.458. Techniques for laparoscopic placement of spinal fusion cages are shown and described in Kuslich U.S. Pat. No. 5,700,291 and Castro U.S. Pat. No. 6,004,326. Implementing the laparoscopic approach requires that one or more laparoscopic access devices, commonly referred to as trocars (see for example Moll U.S. Pat. Nos. 4,601,710 and 4,654,030) be introduced into the abdominal cavity and that the cavity be insufflated to create working space. A laparoscope is inserted through one of the trocar ports to provide visualization of the abdominal cavity and surgical instruments may be introduced either through another trocar port or through a working channel of the laparoscope to dissect, manipulate and retract tissue to gain access to the posterior wall of the abdomen adjacent to the spine. Retractors, including balloon retractors, may be used to retract organs and tissue to maintain a clear working path. Care is taken to avoid damage to the major blood vessels, the aorta and femoral arteries, and the posterior wall of the peritoneum is opened to access the desired spinal vertebral body or disc segment.

C. Imaging Techniques

A variety of tools exist to assist the surgeon in assuring the desired access and treatment are achieved without compromising or adversely affecting adjacent healthy tissue. Treatment of the spine is usually planned based on CT or MR scans and fluoroscopy is commonly used during surgery to assure proper positioning and placement of surgical tools and devices. Image guided spinal surgery has been proposed and is contemplated for use with the surgical treatments proposed herein. See, for example, Cosman U.S. Pat. Nos. 5,662,111; 5,848,967; 6,275,725; 6,351,661; 6,006,126; 6,405,072; Bucholz U.S. Pat. Nos. 5,871,445; 5,891,034; 5,851,183; and Heilbrun U.S. Pat. Nos. 5,836,954 and 5,603,318. The position of instruments typically is detected using a camera and markers on the surgical tool, and an image of the working portion of the instrument is super-imposed upon a pre-operative image, such as a CT, MRI or ultrasound image to show the surgeon where the working instrument is located relative to anatomical landmarks and the tissue to be treated. As imaging techniques and equipment improve, it is contemplated that image guided surgery will evolve to using real time intraoperative images and that the position of the surgical instrument will be shown relative to these real-time intra-operative images in addition to or in place of pre-operative images.

D. Adhesives and Other Repair Materials.

Numerous patents describe previous approaches to disc repair. These include U.S. Pat. No. 6,332,894, Stalcup et al., which describes an orthopedic implant for implanting between adjacent vertebrae comprising an annular bag and a curable polymer and hard particulate with the bag. The polymer is cured after implantation to make it harder and to fuse the hard particulate into a single mass. U.S. Pat. No. 6,264,659, Ross et al., describes a process of injecting a thermoplastic material within an annulus fibrosis of a selected intervertebral disk. U.S. Pat. No. 6,127,597, Beyar et al., describes a solid phase formation device for orthopedic application. The expandable device includes a material that polymerizes after implantation. U.S. Pat. No. 6,419,706, Graf, describes a disc prosthesis comprising a preformed polymer core surrounded by a rigid material coating. U.S. Pat. No. 6,569,442, Gan et al., describes a polymer foam prepared outside the body for intervertebral disc reformation.

U.S. Pat. No. 6,022,376, Assell et al., describes a capsule-shaped prosthetic spinal disc nucleus for implantation into a human intradiscal space, made of a substantially inelastic constraining jacket surrounding a pre-formed amorphous polymer core. U.S. Pat. No. 6,132,465, Ray et al., describes a device similar to the device described in U.S. Pat. No. 6,022,376 with certain shape modifications. U.S. Pat. No. 6,306,177, Felt et al., describes an in situ polymerizing fluid used in tissue repair in the absence of a constraining structure, such as a balloon. The polymerizing materials comprise a quasi-prepolymer component and a curative component containing chain extenders, catalysts and the like. U.S. Pat. No. 4,743,632, Marinovic, discloses the use of a two-part adhesive for use in surgery, where a diisocyanate material is mixed with a polyamine or similar material to produce an in situ cure. Preferred materials are described in our U.S. Pat. No. 6,254,327, and our pending applications US 2003-0135238 and US-2004-0068078.

E. Other References providing Background Information.

These include U.S. Pat. No. Re. 33,258 (Onik et al.), U.S. Pat. No. 4,573,448 (Kambin), U.S. Pat. No. 5,192,326 (Bao et al.), U.S. Pat. No. 5,195,541 (Obenchain), U.S. Pat. No. 5,197,971 (Bonutti), U.S. Pat. No. 5,285,795 (Ryan et al.), U.S. Pat. No. 5,313,962 (Obenchain), U.S. Pat. No. 5,514,153 (Bonutti), U.S. Pat. No. 5,697,889 (Slotman et al.), U.S. Pat. No. 5,755,732 (Green et al.), U.S. Pat. No. 5,772,661 (Michelson), U.S. Pat. No. 5,824,093 (Ray et al.), U.S. Pat. No. 5,928,242 (Kuslich et al.), U.S. Pat. No. 6,004,326 (Castro et al.), U.S. Pat. No. 6.187,048 (Milner et al.), U.S. Pat. No. 6,226,548 (Foley et al.), U.S. Pat. No. 6,416,465 (Brau), WO 01/32100, and FR 2 639 823.

SUMMARY OF THE INVENTION

None of the techniques or devices described above are entirely satisfactory for providing percutaneous or open therapy to damaged spinal discs.

Accordingly, it is one aspect of the present invention to treat disc abnormalities at locations previously not accessible via standard percutaneous approaches and without substantial destruction to the disc. The treatment involves delivery of an in situ polymerizing tissue adhesive into the affected areas of the disc to seal openings in the annulus, to strengthen the annulus, particularly by intra-annular injection of adhesive, and to couple tissues to each other and/or to prosthetics to stabilize and strengthen the disc, or to form a nuclear prosthetic in situ. The improved techniques are particularly important at the posterior lateral and the posterior medial regions of the inner wall of the annulus fibrosus, and adjacent areas of the nucleus, which are poorly accessible with present techniques. The tissue adhesive is characterized in being hydrophilic, self-crosslinking in vivo, and tissue adherent. The invention also comprises suitable devices for administration of the adhesive.

The present invention discloses techniques for modifying the disc annulus and/or nucleus to restore nuclear integrity. The techniques do not involve creating a large defect in the disc capsule. The present invention provides open and minimally invasive surgical methods to treat disc abnormalities at locations previously not accessible via percutaneous approaches, and without substantial destruction of the disc and/or surrounding tissue. The treatment entails delivery of in-situ polymerizing substances to select locations within the disc, particularly including delivery to the location of an annular fissure. More particularly, the surgical methods disclosed herein involve delivering an in-situ polymerizing fluid to repair the annulus and/or nucleus, or to localize spinal prosthetics including nucleus replacement prosthetics.

In addition, the invention provides a surgical method that delivers tissue adhesive to the inner wall of the annulus fibrosus to provide localized repair at the site of an annular fissure. Included are surgical methods for clearing, shaping or cutting nuclear material in order to repair an annular fissure at such a location. Advantageously, the treatments may involve delivery of an in-situ polymerizing tissue adhesive in such a manner that the adhesive couples to and becomes intimately involved with the fibrous structure of the annulus fibrosis. This is particularly significant with respect to the repair of an annular fissure or fixation of an implant structure within the disc nucleus. In a preferred embodiment, the tissue adhesive for this procedure and others is a single-part adhesive, which can be administered to tissue without addition of other components.

The implant structure may comprise any suitable implant grade material, including metal, for example but not limited to titanium, cobalt, chromium, aluminum, nickel, stainless steel, nitinol, and alloys and mixtures; plastics and polymers, for example but not limited to PEEK, polylactide, polyglyclolide, polycaprolactone, polycarbonate, polyester, polyacrylate, polyalkylene, polyurethane, polyphenolic, and blends and copolymers thereof; and other materials, for example but not limited to graphite, ceramics including particulate ceramic fillers, gel-forming materials, and combinations of materials. It is also contemplated that the implant may be formed of the same material as the single-part adhesive. The adhesive can be delivered to seal a fissure in the annulus or to close an opening created to access the nucleus. The adhesive may be introduced to the nucleus after insertion of a nucleus replacement to surround and bind to the implant and form a strong bond to the surrounding annular fibers to hold the implant in place within the disc nucleus. The tissue adhesive may also be used to bond a prosthetic disc replacement in place. Various excipients and additives can be comprised in the implant, such as plasticizers, antioxidants, emulsifiers, colorants, fillers, radioopacifiers, coatings, and similar materials approved for in vivo medical implantation.

In a further embodiment, it is contemplated that the in-situ curing tissue adhesive may be introduced into the nucleus (which may be previously evacuated by nucleotomy) to form a nucleus implant in-situ. Additional tissue adhesive may be introduced at the same time or subsequent to curing of the initial insertion of material to bind the in-situ formed implant to the surrounding annulus. Advantageously, the methods and devices disclosed herein provide access to all regions of the inner wall of the annulus fibrosis to deliver tissue adhesive to the interior nucleus space. Advantageously, the methods and devices disclosed herein provide access to the difficult-to-reach posterior, posterior lateral and posterior medial regions of the inner wall of the annulus.

The proposed methods generally involve the steps of:
1. Accessing a desired portion of spinal disc region by known surgical techniques, preferably in a minimally invasive manner such as a percutaneous posterior-lateral, retroperitoneal, or anterior laparoscopic method. The surgical approach selected may vary depending upon the portion of the spinal disc segment to be treated.
2. Optionally, removing tissue, preferably minimizing removal of healthy tissue while removing diseased or degenerated tissue (e.g. removing bulging portions of the annulus fibrosis, or nucleus pulposis, removal of osteophytes, etc.)

3. Delivering an in-situ polymerizing tissue adhesive to perform a desired repair, which may included repairs to any or all of the exterior of the annulus, the interior wall of the annulus, or within the wall of the annulus fibrosis, augmenting or replacing all or a portion of the disc nucleus (which may have previously been removed during the same or prior surgery) with the in-situ polymerizing fluid, or securing a spinal disc replacement implant, disc nucleus replacement or other spinal implant in place.

4. If the disc annulus has been compromised during surgery and is to be closed as part of the surgical procedure, closing the opening in the disc nucleus. Preferably, the in-situ polymerizing fluid is used to close the opening in the disc annulus.

5. Closing any openings created to gain access to the spine.

The present invention further provides methods for manipulating a disc tissue with herniation, or with a fissure or tear in an intervertebral disc, the disc having a nucleus pulposus and an annulus fibrosus, the annulus having an inner wall of the annulus fibrosus. The methods employ a variety of externally guidable cutting and delamination devices to repair the disc. The procedure is performed with one or more cutting, shaping, and/or delivery devices passed through a trocar having a distal end, a proximal end, a longitudinal axis, and an intradiscal section at the catheter's distal end on which there is at least one functional element. A series of cannulae of gradually increasing diameter may be used to provide a small initial entry diameter gradually increased to the desired diameter to access the spine. Alternatively, an expanding cannula device such as disclosed in the previously mentioned Dubrul, Bonutti or Davison patents may be used to provide minimal entry opening size increased to a larger desired diameter access the spine.

A variety of surgical approaches such as the posterior lateral and retroperitoneal approaches described above can be used. One method employs a wire, ribbon or catheter to be advanced through the annulus and into the nucleus pulposus and around an inner wall of an annulus fibrosus by applying a force to the proximal end. In the case where the annulus is open, the applied force is insufficient for the intradiscal section to puncture the annulus fibrosus. In the case where the annulus is not open, the intradiscal section of the device may be substantially sharper to provide a first passage through the annulus and into the nucleus. The functional element, which may simply be a hollow needle, is positioned at a selected location in the disc by advancing or retracting the device and optionally twisting the proximal end of the device. The catheter and/or the needle may be steerable in order to deliver the tissue adhesive to a particular location within the disc or annulus. The procedure allows the administration of tissue adhesive to treat annular fissures, to fill the nucleus to form an implant in-situ, or to bind a pre-formed implant in place within the disc nucleus.

A method of treating an intervertebral tissue comprises the steps of placing a catheter adjacent to the defect and delivering tissue adhesive sufficient to strengthen and bond collagen and to seal the fissure. This operation may include filling portions of the nucleus. Alternatively, the fissure may be sealed and subsequently the annulus filled and pressurized allowing for the injected polymer to solidify before removing the needle.

In addition to the method, there is provided a tissue adhesive sufficient to provide the therapeutic effect of strengthening the intervertebral space and preventing extrusion of the disc or a prosthetic. The preferred adhesive is a single-component polyisocyanate based adhesive as described in U.S. Pat. Nos. 6,254,327, 6,296,607, and co-pending U.S. provisional patent application Ser. No. 60/557,314, which is incorporated herein by reference in its entirety. In one aspect, the present invention provides a minimally invasive method and device for treating fissures of discs at selected locations within the disc.

Another aspect of the invention is to provide an apparatus that delivers tissue adhesive to the inner wall of the annulus fibrosus to provide localized repair at the site of an annular fissure.

Another aspect of the invention is to provide a device that has a distal end that is inserted into the disc and accesses the posterior, posterior lateral and the posterior medial regions of the inner wall of the annulus fibrosus in order to repair an annular fissure at such a location.

Another aspect of the invention is to provide a minimally invasive method and device for treating discs at selected locations within the annulus fibrosus. In particular it relates to fixing the fibers of the annulus in a preferred orientation and providing increased rigidity to the annulus by increasing its volume with a polymerizing fluid.

Another aspect of the invention is to provide an apparatus which delivers tissue adhesive within the wall of the annulus fibrosus to provide increased support and space between vertebral bodies.

Another aspect of the invention is to provide a device that has a distal end that is inserted into the wall of the annulus and accesses the posterior, posterior lateral and the posterior medial regions of the annulus fibrosus in order to repair an annulus at such a location.

Another aspect of the invention is to provide a minimally invasive method and device for fixing, fitting, and augmenting the size of prosthetic nucleus replacement devices either during implantation or at any time post implantation.

Another aspect of the invention is to provide a new method of implanting a nucleus prosthetic that includes closing the hole created in the annulus by implantation of the prosthetic.

Another aspect of the invention is to provide an apparatus which delivers tissue adhesive to the inner wall of the annulus fibrosus to localize and fit a nucleus prosthetic.

Another aspect of the invention is to provide a device that has a distal end that is inserted into the disc and accesses the posterior, posterior lateral and the posterior medial regions of the inner wall of the annulus fibrosus in order to localize and fit a nucleus prosthetic.

Another aspect of the invention is to provide a method of treating an intervertebral tissue comprises the steps of placing a catheter adjacent to the tissue, or an adjacent prosthetic, and delivering tissue adhesive sufficient to strengthen and bond collagen and other local tissues to repair a fissure or hole, to strengthen an annulus, and to localize and fit a nucleus prosthetic. These operations may include filling portions of a nucleus cavity, or of a fissure or other deficit, under pressure. Alternatively or in addition, filling operations may be facilitated by unloading the particular region of the spine to enhance filling of an intervertebral space.

Another aspect of the invention is to provide a tissue adhesive sufficient to provide the therapeutic effect of strengthening the intervertebral space and preventing extrusion of the disc. The tissue adhesive may be of a wide variety of types, but preferably is a one part adhesive that cures in situ, and which is a preferred embodiment is a hydrophilic, substantially water soluble isocyanate derivative of a polyol or polyols.

These and other aspects of the invention have been accomplished by the present invention which provides methods and systems for manipulating annulus tissue with and without a fissure or tear, and native or prosthetic nucleus tissue, in an intervertebral disc, the disc having a nucleus pulposus and an annulus fibrosus, the annulus having an inner wall of the annulus fibrosus.

BRIEF DESCRIPTION OF THE FIGURES

The invention is understood by reference to the following figures.

FIG. 9 illustrates an alternative approach of creating multiple channels in the disc nucleus and delivering adhesive to the channels, wherein FIG. 9A shows a disc;

FIG. 9B shows a disc sectioned horizontally;

FIG. 9C shows the sliced disc augmented by a layer of injected material;

FIGS. 9D and 9E show side and top views of a disc augmentation technique;

FIG. 9F shows the catheter system used to inject the filler;

FIG. 9G shows a luer connection with vent port; and

FIG. 9H shows a cross section of FIG. 9F;

FIG. 10 illustrates a nucleus bore, with

FIG. 11 illustrates an alternative approach to disc nucleus removal, with

FIG. 14 illustrates an alternative approach to annulus augmentation using a wire or ribbon to delineate layers of the annulus to create space to facilitate adhesive placement, wherein FIG. 14A shows insertion of a wire;

FIG. 14B shows injection of adhesive;

FIGS. 14B-1 and 14B-2 show detail of the snaring of the returned wire; and

FIG. 14C shows the adhesive-filled channel;

FIG. 17 illustrates a two-step technique wherein a first application of adhesive to the disc nucleus is allowed to substantially or completely polymerize, and a second application of adhesive expands and fills the first material to expand and fill the disc space, where

FIG. 19 illustrates delivery of a disc nucleus implant and adhesive securement of the implant in the disc, wherein FIG. 19a shows the implant delivery via a catheter;

FIG. 19b shows placement of the implant in the nucleus space;

FIG. 19c shows injection of adhesive, and

FIG. 19d shows removal of excess cured adhesive;

DETAILED DESCRIPTION OF THE INVENTION AND PREFERRED EMBODIMENTS

The present invention provides methods and apparatus for treating intervertebral disc disorders by delivering a tissue adhesive to the spinal disc space, preferably within the disc nucleus to repair a fissure, particularly a fissure of the annulus fibrosis, which may or may not be accompanied with contained or escaped extrusions. The adhesive may also be used to create a disc nucleus implant in-situ, or bond a pre-formed disc nucleus implant in place. Preferably, the methods and devices are used to deliver a single-part in-situ polymerizing tissue adhesive to accomplish the desired surgical results.

In one aspect, the invention comprises coupling a tissue-polymerizing agent with a guidable intervertebral disc apparatus for accessing and delivering an in-situ polymerizing agent at a location in an intervertebral disc having a nucleus pulposus and an annulus fibrosus, the annulus having an inner wall. The invention is distinguished from conventional percutaneous interventions in not being reliant on reference measurements and selection of appropriate instrument sizes. Such conventional instruments are typically designed for one disc size. Additionally, in some embodiments the present invention can be used with any of a variety of insertional apparatus to provide proximity to the disc, such as insertional apparatus known in the art as "introducers". An introducer has an internal lumen with a distal opening at a terminus of the introducer to allow insertion/manipulation of the operational parts into the interior of a disc.

The elements of the invention function in combination to modify or change certain features of the disc anatomy. For purposes of this specification, the inner wall of the annulus fibrosus can include the young wall comprised primarily of fibrous material as well as the transition zone, which includes both fibrous material and amorphous colloidal gels.

Figure 1A:
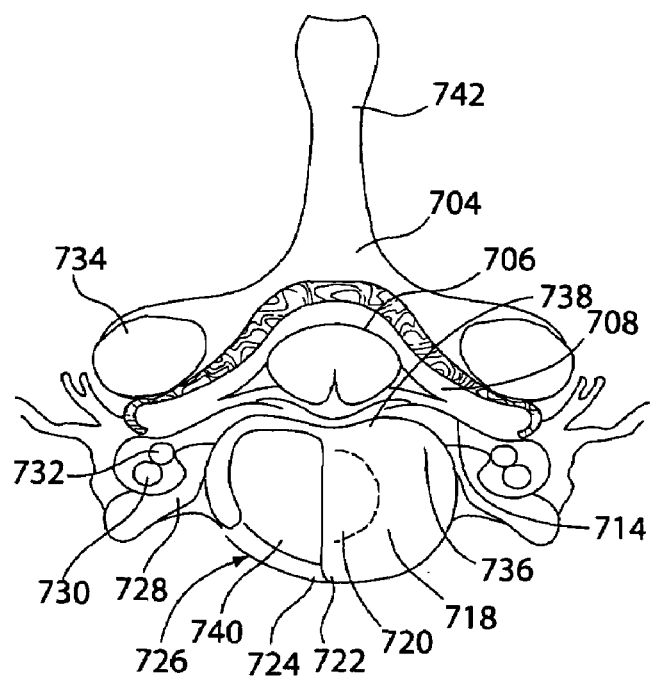
FIG. 1(a) is a superior cross sectional anatomical view of a cervical disc and vertebra.
Figure 1B:
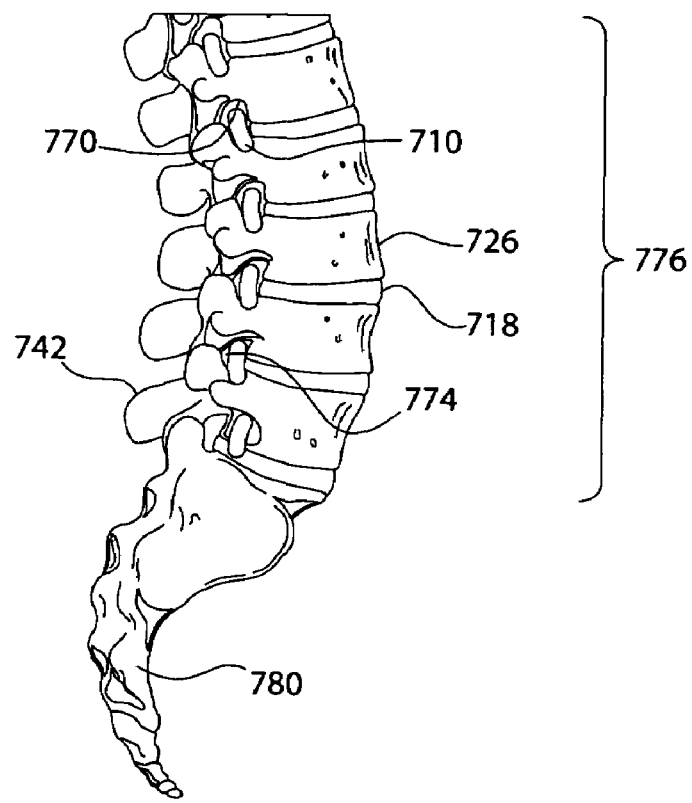
FIG. 1(b) is a lateral anatomical view of a portion of a lumbar spine.
Figure 1C:
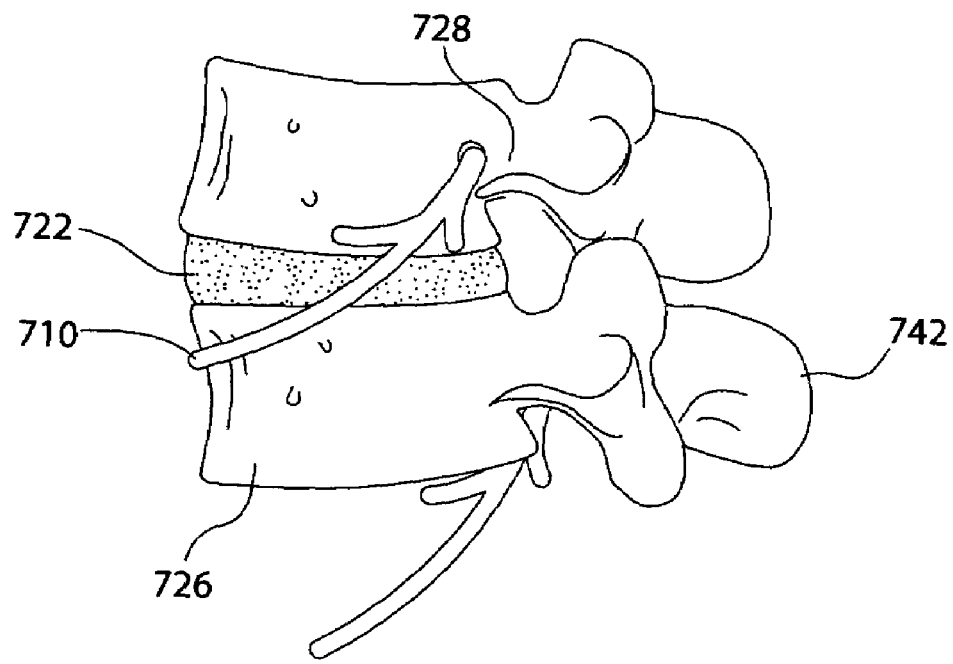
FIG. 1(c) is a posterior-lateral anatomical view of two lumbar vertebrae and illustration of the triangular working zone.

To appreciate the situation in which repairs to spinal discs is attempted, the anatomy is illustrated in FIGS. 1a and 1b, which illustrate a cross sectional view of the anatomy of a vertebra and associated disc and a lateral view of a portion of a lumbar and thoracic spine, respectively. (A more detailed and three-dimensional view of the parts of the vertebrae and disc than can be provided here can be found in good anatomy references and textbooks.) Structures of a typical cervical vertebra (superior aspect) are shown in FIG. 1(a): 704—lamina; 706—spinal cord; 708—dorsal root of spinal nerve; 714—ventral root of spinal nerve; 718—intervertebral disc; 720—nucleus pulposus; 722—annulus fibrosus; 724—anterior longitudinal ligament; 726—vertebral body; 728—pedicle; 730—vertebral artery; 732—vertebral veins; 734—superior articular facet; 736—posterior lateral portion of the annulus; 738—posterior medial portion of the annulus; 740—vertebral plate, and 742—spinous process. In FIG. 1(a), one side of the intervertebral disc 718 is not shown so that the anterior vertebral body 726 can be seen. FIG. 1(b) is a lateral aspect of the lower portion of a typical spinal column showing the entire lumbar region and part of the thoracic region and displaying the following structures: 718—intervertebral disc; 726—vertebral body; 742—spinous process; 770—inferior vertebral notch; 710—spinal nerve; 774—superior articular process; 776—lumbar curvature; and 780—sacrum. FIG. 1c shows a posterior-lateral anatomical view of two lumbar vertebrae, including the pedicle 728, the spinal nerve 710, the annulus fibrosus 722, the vertebral body 726, and the spinous process 742.

The presence of the spinal cord 706 and the posterior portion of the vertebral body, including the spinous process 742, and superior articular 774 and inferior articular processes (inferior is not visible; behind superior process 774), prohibit introduction of a needle or trocar from a directly posterior position. This is important because it is most frequently the posterior disc wall that is the site of symptomatic annulus tears and disc protrusions/extrusions that compress or irritate spinal nerves in degenerative disc syndromes. The inferior articular process, along with the pedicle 728 and the lumbar spinal nerve 710, form a small "triangular" window through which introduction can be achieved from the posterior lateral approach. It is well known that percutaneous access to the disc is achieved by placing an introducer into the disc from this posterior lateral approach, but the triangular window does not allow much room to maneuver. Once the introducer pierces the tough annulus fibrosus, the introducer is fixed at two points along its length and is restricted in movement. Hence, this common approach allows only restricted access to portions of the nucleus pulposus. Specifically, the posterior half of the nucleus or the posterior wall of the disc is inaccessible.

Figure 1D:
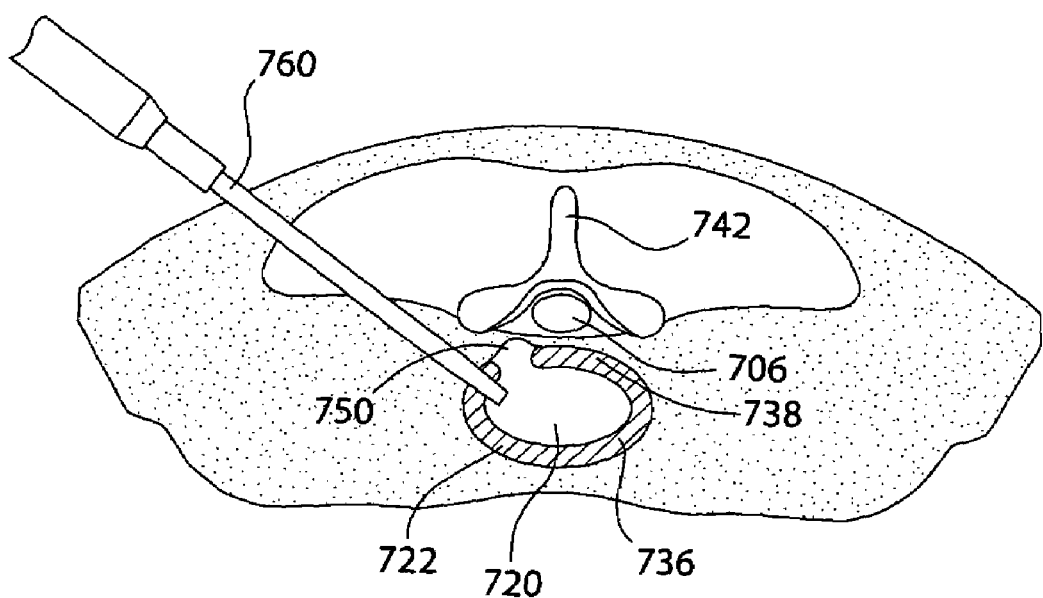
FIG. 1(d) is a superior cross sectional view of the required posterior lateral approach.

FIG. 1d illustrates the posterior lateral approach through the triangle, and allows visualization of the problem. In this illustration, there is a fissure 750 in the posterior wall of the annulus 722, through which the nucleus 720 is bulging, thereby exerting pressure on the spinal cord 706 or on a spinal nerve (not illustrated). A rigid apparatus 760 inserted through the posterior lateral region 738 of the annulus 722 can access the nucleus 720, for example to remove it, but cannot readily treat the fissure 750, or strengthen the posterior medial annulus 738 to prevent recurrence. Although a nuclear prosthetic can be delivered into the space formerly occupied by the nucleus, it will not be attached to the surrounding annulus 722, nor will the fissure 750 be closed.

Figure 1E:
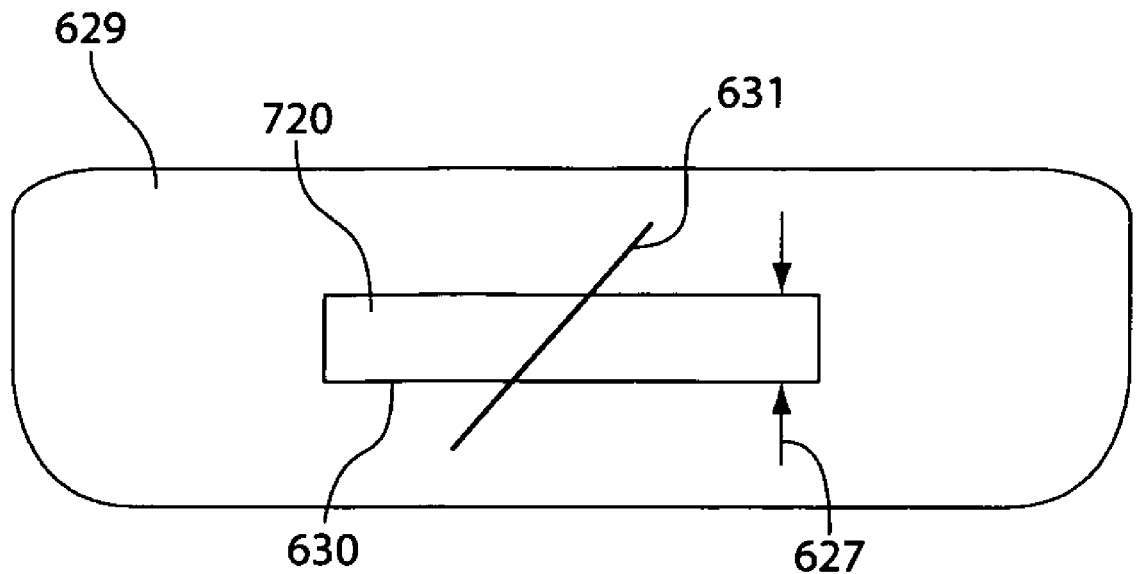
FIG. 1e is a side view.
Figure 1F:
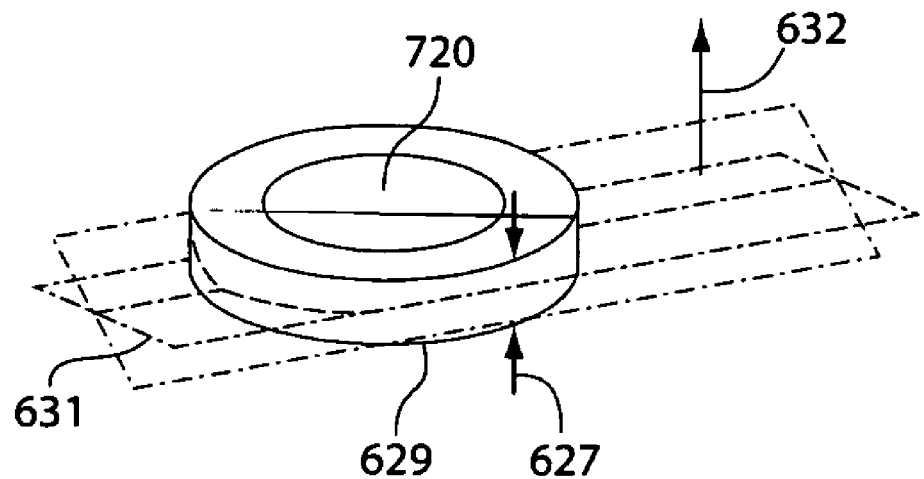
FIG. 1f is a perspective view of a disc and some critical measurements.

FIGS. 1e and 1f are schematic views of the anatomy of the disc itself, and of key orientations in it. As used herein, the terms "disc plane", oblique plane" and "cephalo-caudal plane" refer to orientations of a catheter within the intervertebral disc. Referring to FIG. 1e, a disc plane 630 of the intervertebral disc 629 is generally a plane of some thickness 627 within the nucleus pulposus 720. The disc plane 630 is orthogonal to the axis 632 formed by the spinal column. An oblique plane 631 is a plane which is tilted in orientation relative to axial plane 630. However, when the oblique plane 631 is tilted 90 degrees with respect to plane 632, such a plane 631 would be substantially vertical in a standing human and is referred to as a cephalo-caudal plane. Disc plane 630 has a thickness no greater than the thickness of the intervertebral disc, preferably a thickness no greater than 75% of the thickness of the intervertebral disc, and more preferably a thickness no greater than 50% of a thickness of an intervertebral disc. In a healthy disc, the spinal axis 632 is orthogonal to disc plane 630, and the angle between plane 630 and plane 631 is zero. One aspect of the present invention is the alteration of the thickness 627 of disc 629 to achieve a zero angle.

Nucleus replacement devices are intended to be used where the annulus and vertebral endplates remain intact, and the prosthesis is implanted into the nucleus cavity through a window formed in the annulus. Insertion of the prosthetic through a window in the annulus requires that the prosthetic be smaller than the nucleus cavity. Current devices expand when implanted to a relatively large post-implant size that is as much as 3 times the original implantation volume. The use of a reduced size nucleus prosthesis means that the prosthesis can move within the nucleus cavity until the prosthesis reaches its target size, which can require as much as three days to achieve. In some cases the prosthesis explants through the annulus opening. Even when the opening is closed with sutures the implant can still push through the annulus opening. Additionally, a reduced size implant generally means the implant must be stiffer than the optimal flexibility the implant is intended to achieve once enlarged. This further reduces the size of the implant so that it will fit through the annulus window. The result is a compromise between ease of implantation and final state implant flexural characteristics. This situation can be remedied using an in situ acting surgical adhesive and bulking agent. A variety of surgical adhesives are potentially useable in the invention, but a preferred adhesive is described here.

Surgical Adhesives and Bulking Agents

Turning now to the functional aspects of the invention, the two principal material components of the invention are a suitable tissue adhesive and bulking agent ("adhesive"), and a suitable apparatus ("injector") for depositing the adhesive. The invention further comprises improved methods for use of an adhesive to repair defects in a disc, including repair of the annulus, optionally accompanied by immobilization of a prosthesis and/or filling of a nuclear space. Regarding the adhesive or bulking agent, a liquid material is introduced into the intervertebral space to repair the tissue and fluids contained therein. The liquid material must have a low viscosity and be capable of delivery through a small diameter needle, cannula or catheter, for example through a typical catheter having a diameter ranging from 16 G to 25 G (but smaller diameter devices can be used if viscosity is sufficiently low.) Low viscosity is important in three respects: 1) ease of delivery, 2) prevention of delayed pressure transference from source to the target tissue site, and 3) permits sensing of resistance feedback by the operator to determine appropriate delivery volumes.

The preferred material of the present invention is a single component, self-curing adhesive that polymerizes in-situ forming internal cross links as well as bonds to surrounding tissue and bone. The polymerization of the preferred material is initiated either by aqueous fluids present in the tissue or by addition of physiological saline or other medicinal solution. The polymerization of these adhesives preferably does not require the addition of cross linkers, catalysts, chain extenders, or complementary components of an adhesive. Preferably, cross linking and tissue bonding is mediated either by aqueous fluids present in the tissue, or by premixing of the adhesive with physiological saline or other medicinal saline solution at the time of administration. The polymerization time of preferred adhesives is variable, and preferably is in the range of about 30 seconds to 30 minutes or more, depending on the application. Preferred materials are described in our U.S. Pat. No. 6,254,327, and our pending applications US 2003-0135238 and US 2004-0068078, each of which is hereby incorporated by reference (where permitted).

Polymerization time can be adjusted by selection of properties and components of the tissue adhesive. Principally, the material is a liquid comprising a polyisocyanate-capped polyol, typically macromolecular in size, having a molecular weight of about 1000 Daltons or more, more typically at least about 2000 Daltons, and yet more typically in a range of about 3000 D to about 10,000 D, depending on application. Higher molecular weight macromers may be of use in adhesives having great pliability (and lower tensile strength). The adhesive also typically comprises a certain amount of low-molecular weight polyisocyanate, for example with a molecular weight less than about 1000 D. This may comprise the polyisocyanate used to cap the polyols. The capped polyol is multifunctional, and typically at least partially trifunctional or higher. The polyol may be any of various biocompatible substances such as polyethylene oxide, polypropylene oxide, polyethylene glycol, and copolymers of these. A preferred polyol has about 10% to about 30% by weight propylene oxide subunits, and the rest ethylene oxide. The polyisocyanate is typically difunctional. Fast reacting formulations use an aromatic diisocyanate such as toluene diisocyanate. Slow reacting formulations use an aliphatic diisocyanate such as isophorone diisocyanate. Alternatively, the polymerization time can be adjusted by selection of appropriate molecular weight polyols. The higher molecular weight polyols produce lower viscosity capped reaction products and faster reacting solutions.

The cure times achieved using the approaches described above depend, in part, on controlling one or more of the rate of water diffusion into the prepolymer, the rate of isocyanate to amine conversion, and the activity of the isocyanate-functionalized ends. There are various additions to the prepolymer that can be made at the time of application to speed prepolymer curing. For example, when water is added to the prepolymer just before application, the cure time dependence on water diffusion is reduced. Generally, addition of water in volumetric ratios of approximately 50% maximally reduces cure time. When additional water is added, such as 80 or more % by volume, the cure time increases from its fastest mixed cure time because the polymer density decreases. Similarly, when using higher concentrations of prepolymer, such at 80% or more by volume, the cure time increases from its fastest cure time because the water availability decreases. However, all mixtures with water, from 1% up to about 95% by volume, cure faster than application of prepolymer placed directly on tissue. It is sometimes desirable to lightly irrigate the location with water after pure prepolymer has been applied to tissue.

The first action of water with the prepolymer is to convert some of the active isocyanate ends on the isocyanate capped polyol and some of the active isocyanate ends on the free isocyanate to amine groups. Amine groups react with other isocyanate groups to cause rapid chain extension and eventual crosslinking. Therefore, reduced cure times can also be achieved by substituting some or all of the water admixture with aqueous amines.

The preferred material is an aromatic isocyanate made by end capping a deionized, dried polyalkylene diol with toluene diisocyanate (TDI), and then reacting the end-capped diol with a deionized dried triol. The preferred diol is a polyethylene glycol/polypropylene glycol co-polymer (random, block or graft), with EO (ethylene oxide) and PO (propylene oxide) in weight ratios ranging from about 95:5 to about 25:75, and more preferably about 75% EO and 25% PO. The preferred triol is trimethylol propane (TMP). The preferred composition is the reaction product of from about 25% to 35% TDI, from about 65% to 75% diol (75% EO: 25% PO) and from about 1% to about 8% TMP. Most preferably, the composition is the reaction product of about 30% TDI, about 70% of the 75:25 diol, and about 1% to about 2% TMP.

These polymer mixtures have the added advantage of being water-soluble. Their water solubility enables them to be injected into tissue to polymerize the tissue; or, alternatively to solidify as gels to stabilize tissue or structures. The material acts as a self-sealing fluid when injected into body cavities.

Isocyanate-capped polyols, while preferred, are not the sole adhesives suitable for use in the invention. An adhesive for use in the invention is preferably hydrophilic in character, and more preferably is water-soluble before being crosslinked. This hydrophilicity enable the adhesive to be injected into tissue to polymerize in contact with, and bond to, the tissue, as adhesive and/or as local bulking agent to fill gaps or fissures, or to stabilize implants. The adhesive acts as a self-sealing fluid when injected into cavities or gaps. Once cured in situ, the hydrophilic adhesive will absorb fluid from the tissue, forming a structure that will be at least somewhat gel-like in character. The cured adhesive will swell to a controlled extent, exerting a controlled amount of local pressure. The tensile properties of the cured adhesive can be adjusted so that the adhesive, like the native tissues of the annulus or of the nucleus, yields under pressure while exerting a restorative force on the surrounding structures. Hence, the adhesive-tissue composite tends to return to its original shape and location after movement of the spine. These properties can be controlled by the composition of the adhesive, or by providing a controlled degree of dilution with saline at the time of administration. This is in contrast with rigid materials, which tend to fracture rather than yield, and to flowable media, which have no tendency to return to their original shape after relaxation of stress. In particular, hydrophobic adhesives tend to become rigid, favoring fracture of the cured adhesive at the surface of the tissue or implant. They also tend not to bond to tissue, which is highly hydrophilic.

The unpolymerized adhesive is preferably polymeric in nature, as opposed to being a low molecular weight monomer before curing, such as a cyanoacrylate. A number of known polymers are potentially useful in formation of suitable adhesives. The polymers are preferably hydrophilic, for example, sufficiently hydrophilic to swell in water. A suitable range of swelling can be, at atmospheric pressure, between from 5% to about 100%, and more typically is from about 10% to about 50%. More preferably, the prepolymers are sufficiently hydrophilic to have substantial solubility in water, such as, for instance, 1 g/l or more, preferably 10 g/l or more, optionally 100 g/l or more. The molecular weight of the prepolymers is not critical. In the present application, number-average MW, or alternatively the MW number on the label of a commercial product, is in the range extending from about 500 D, more preferably about 1000, most preferably about 2000, up to 100,000 D, more preferably 50,000 D, most preferably 25,000 D. The molecular weight will vary by application and with polymer backbone. It will generally be as low as feasible, to minimize viscosity, while being sufficiently high to provide the desired materials properties, such as strength of adherence to tissue, or adequate tensile strength. However, higher viscosities may be desirable in some cases, especially when curing time is longer. The polymers are preferably selected from those approved for in-vivo medical application. The polymers may be stable in the body, or may degrade in the body to smaller, excretable molecules ("degradable"). A wide variety of linkages are known to be unstable in the body. These include, without limitation, esters of hydroxy acids, particularly alpha and beta hydroxy carboxylic acids; esters of alpha and beta amino acids; carboxylic acid anhydrides; phosphorous esters; and certain types of urethane linkages. Generally, it is preferred that the adhesive be stable in the body for prolonged periods, as the fibrous materials of the annulus have very limited self-repair capabilities, and the nucleus has virtually none. However, if methods are found to enhance natural biological repair of the nucleus or annulus, then degradable adhesives or fillers could be preferred.

The polymers also have reactive groups covalently attached to them, or part of the backbone. The reactive groups are suitable for reaction with tissue, and for crosslinking in the presence of water or components of bodily fluids, for example water and protein. Suitable groups include isocyanate, isothiocyanate, anhydrides and cyclic imines (e.g., N-hydroxy succinimide, maleimide, maleic anhydride), sulfhydryl, phenolic, polyphenolic, and polyhydroxyl aromatic, and acrylic or lower alkyl acrylic acids or esters. Such reactive groups are most commonly bonded to a preformed polymer through suitable linking groups in the polymer. Commonly found linking groups include, without limitation, amines, hydroxyls, sulfhydryls, double bonds, carboxyls, aldehydes, and ketone groups. Of these groups, aliphatic hydroxyls are among the most widely used.

Thus, suitable base polymers include poly(alkyl)acrylic acids and polyhydroxyalkyl acrylates, polysaccharides, proteins, polyols, including polyetherpolyols, polyvinyl alcohol, and polyvinylpyrrolidone, and these same structures with amine or sulfur equivalents, such as polyethyleneimine, aminosugar polymers, polyalkylamine substituted polyethers, and others. Any of these polymers can be substituted with two or three reactive groups, as is required to form a crosslinkable polymer. When there are many substitutable linking groups, as with polysaccharides, only a few of the substitutable groups (here, mostly hydroxyls) should be substituted, and the derivatized polymer will have a somewhat random substitution. Preferably, the hydrophilic polymer will have only a few substitutable linking groups. Polyether polyols grown on glycol or amine starters will typically have reactive groups only at the end of the polyether chains, allowing for detailed control of stoichiometry. Such polymers are preferred. Most preferably, the base polymer is a polymer of ethylene glycol, or a copolymer of ethylene glycol with one or more of propylene glycol, butylene glycol, trimethylene glycol, tetramethylene glycol, and isomers thereof, wherein the ratio of ethylene glycol to the higher alkanediol in the polymer is sufficient to provide substantial water solubility at room or body temperature. Such polymer substrates can be synthesized by known methods. More typically, preformed polyetherpolyols are purchased, optionally in a prequalified medical grade, from any of numerous catalogs or manufacturers.

As noted above, the preferred reactive material comprises a polyisocyanate-capped polymeric polyol and a small amount of free poly isocyanate. Such materials and their synthesis are described in detail in U.S. Pat. No. 6,524,327. The small amount of excess polyisocyanate, typically of molecular weight less than about 1000 Daltons, maximizes the reactivity of the polyols, and by directly and rapidly reacting with tissue, promotes bonding of the adhesive to tissue. Typically the small isocyanate contains up to about 3% of the number of active isocyanate groups on the polymer. The capped polyol is multifunctional, and typically is trifunctional or tetrafunctional, or a mixture of trifunctional and/or tetrafunctional with difunctional. The polyol is preferably at least in part a polyether polyol as described above.

The polyisocyanate is typically difunctional, but tri- or tetrafunctional, or star, forms of isocyanate are known and can be useful. Branching (tri- or tetra-functionality) may be provided by a trifunctional polymer, or by providing a tri- or tetrafunctional low molecular weight polyol, such as glycerol, erthyritol or isomer, or trimethylolpropane (TMP). Fast reacting formulations use an aromatic diisocyanate such as toluene diisocyanate. Slow reacting formulations use an aliphatic diisocyanate such as isophorone diisocyanate. Many additional diisocyanates are potentially useful. Some are listed in U.S. Pat. No. 6,524,327, and these and others are found in chemical catalogs, for example from Aldrich Chemical. Alternatively, the polymerization time can be adjusted by selecting appropriate molecular weight polyols. The higher molecular weight polyols produce lower viscosity capped reaction products and slower reacting solutions. However, at any molecular weight of the polyol(s), the reaction rate is most significantly determined by the reactivity of the functional end group attached to the polyol.

The adhesive preferably is liquid at room temperature (ca. 20 degrees C.) and body temperature (ca. 37 degrees C.), for ease of administration and of mixture with additives, etc. The adhesive preferably is stable in storage at room temperature, when protected from moisture and light.

The reactive polymer tissue adhesive may be supplemented by the addition, during manufacture or at the time of administration, of ancillary materials. These may include reinforcing materials, drugs, volume or osmotic pressure controlling materials, and visualization aids for optical, fluoroscopic ultrasound or other visualization of fill locations. Reinforcing materials may include particulate materials, fibers, flocks, meshes, and other conventionally used reinforcers. It is preferred that these be commercial materials approved for in vivo medical use. Visualization materials include a wide variety of materials known in the art, such as, among others, small particles of metals or their oxides, salts or compounds for fluoroscopy, gas-filled particles for ultrasound, and dyes or reflecting particles for optical techniques.

Osmotic properties can be adjusted for immediate or long-term effects. The preferred polyether polyol isocyanates have little ionic charge either before or after polymerization. However, in some situations, as described below, it is desirable to have a controlled degree of swelling in water after curing. This can be controlled in part by the ratio of ethylene glycol to other polyols in the formulation. It can also be adjusted by adding charged groups to the formulation. A simple method is to add charged polymers or charged small molecules to the adhesive at the time of application, for example dissolved in an aqueous solution. Charged polymers, such as polyacrylic acids, will react poorly with the isocyanates, but will tend to be trapped in the polymerized matrix. They will tend to increase the swelling of the cured material. In turn, this would allow the use of higher proportions of non-ethylene glycol monomers in the polyols. Alternatively, charge could be introduced by addition of hydroxy carboxylic acids, such as lactic acid, or tartaric acid, during synthesis or during administration. Added polymers could instead be polyamines, but, to avoid rapid polymerization, should be tertiary or quaternary amines or other amine types that will not react with isocyanate. A method of increasing swelling is to incorporate higher concentration of diffusible ions, such as soluble salts—e.g., sodium chloride—into the adhesive at the time of application. The salt will attract water into the adhesive polymers; after polymerization, the salt will diffuse away and the gel will remain expanded.

The reactive polymer can be adjusted in several ways to optimize its post-cure properties for the particular situation. A preferred method of adjustment of properties is dilution of the polymer with water, saline, or other aqueous solution. A typical dilution would be in the range of 5% or less (volume of saline in liquid polymer), for formation of dense, high-tensile, low-swelling deposits, up to about 95% (19 vol. saline/vol. polymer) for readily swelling, highly compliant deposits or bonds. In formulation, allowance must be made for the amount of water that will flow into the adhesive from the tissue during reaction. This will usually be relatively small for bulk deposits, but is of more concern for thin adhesive layers. In thin layers, fast-curing compositions will be preferred, such as compositions with a higher proportion of aromatic diisocyanates. In general, dilution will reduce the tensile strength and the modulus. The amount of dilution will tend to be different depending on whether the modulus or tensile strength is to match that of the annulus (higher) or the nucleus (lower).

Various non-reactive ingredients can be added to the polymer solution either in the prepolymer or in the aqueous solution to alter the hydrogel mechanical properties, e.g., tensile strength, elasticity and bubble size. Inert particulate such as tantalum powder will result in bubble nucleation and a finer bubble size, increase the modulus of the hydrogel, and make the hydrogel radio opaque. Emulsifiers can be added to increase mix homogeneity, reduce bubble size, and provide a higher elongation at break. It is possible to use the same diol used to construct the prepolymer as an emulsifier. Alternatively, a higher or lower molecular weight diol may be used. The ratio of EO/PO can be altered to increased mixability, or pure forms of EO or PO can be used. When pure EO is used, the mixture of prepolymer and aqueous solution becomes non-Newtonian, and tends to take on a stringy consistency, which can further improve elasticity.

Other adjustable factors include the molecular weight of the polymer, and its degree of branching; and its hydrophilicity, which is a function of the particular polyol or polyols used in the formulation. In addition, additives, as described above, can also influence these properties.

Examples of the Polymeric Composition

The invention comprises a liquid preparation for use in medicine, and its uses therein. The liquid preparation contains a reactive polymer, which comprises a "base polymer" or "backbone polymer", reactive groups on the backbone polymer, and a slight excess of "free" (low molecular weight) polyreactive molecules. The liquid composition is prepared by a method requiring no catalysts and essentially no solvent. The reactive liquid polymer is self-curing when applied to tissue, by absorption of water and other reactive molecules from the tissue. The cured polymer is used to seal tissue to tissue, or to devices; to apply a protective coating to tissue; to form an implant within or upon tissue; to deliver drugs. The cured polymer is optionally provided with biodegradable groups, and has a controllable degree of swelling in bodily fluids.

Backbone Polymers

The backbone polymer will comprise a polymeric segment, of molecular weight about 500 D or more, preferably about 1000 to about 10,000 D, optionally up to about 15 kD or 20 kD. The backbone polymer will contain groups that can be easily derivatized ("capped") to form the final reactive group. Such groups are preferably alcohols or amines, or optionally sulfhydryls or phenolic groups. Examples include polymers such as a polymeric polyol, or optionally a polymeric polyamine or polyamine/polyol. The preferred polyols are polyether polyols, such as polyalkylene oxides (PAOs), which may be formed of one or more species of alkylene oxide. The PAO, when comprising more than one species of alkylene oxide, may be a random, block or graft polymer, or a polymer combining these modes, or a mixture of PAO polymers with different properties. Preferred alkylene oxides are ethylene oxide and propylene oxide. Other oxiranes may also be used, including butylene oxide. PAOs are typically made by polymerization onto a starter molecule, such as a low molecular weight alcohol or amine, preferably a polyol. Starting molecules with two, three, four or more derivatizable alcohols or other derivatizable groups are preferred. The multi-armed PAOs obtained from such starters will typically have one arm for each group on the starter. PAOs with two, three or four terminal groups are preferred. Mixtures of PAOs or other backbone polymers, having variable numbers of arms and/or variation in other properties, are contemplated in the invention.

Common polyols useful as starters in the present invention are aliphatic or substituted aliphatic molecules containing a minimum of 2 hydroxyl or other groups per molecule. Since a liquid end product is desired, the starters are preferably of low molecular weight containing less than 8 hydroxyl or other groups. Suitable alcohols include, for illustration and without limitation, adonitol, arabitol, butanediol, 1,2,3-butanetriol, dipentaerythritol, dulcitol, erythritol, ethylene glycol, propylene glycol, diethylene glycol, glycerol, hexanediol, iditol, mannitol, pentaerythritol, sorbitol, sucrose, triethanolamine, trimethylolethane, trimethylolpropane. Small molecules of similar structures containing amines, sulfhydryls and phenols, or other groups readily reactive with isocyanates, are also useable.

The PAO, or other backbone polymer, may optionally incorporate non-PAO groups in a random, block or graft manner. In particular, non-PAO groups are optionally used to provide biodegradability and/or absorbability to the final polymer. Groups providing biodegradability are well known. They include hydroxy carboxylic acids, aliphatic carbonates, 1,4-dioxane-2-one (p-dioxanone), and anhydrides. The hydroxy carboxylic acids may be present as the acid or as a lactone or cyclic dimmer, and include, among others, lactide and lactic acid, glycolide and glycolic acid, epsilon-caprolactone, gamma-butyrolactone, and delta-valerolactone. Amino acids, nucleic acids, carbohydrates and oligomers thereof can be used to provide biodegradability, but are less preferred. Methods for making polymers containing these groups are well known, and include, among others reaction of lactone forms directly with hydroxyl groups (or amine groups), condensation reactions such as esterification driven by water removal, and reaction of activated forms, such as acyl halides. The esterification process involves heating the acid under reflux with the polyol until the acid and hydroxyl groups form the desired ester links. The higher molecular weight acids are lower in reactivity and may require a catalyst making them less desirable.

The backbone polymers may also or in addition carry amino groups, which can likewise be functionalized by polyisocyanates. Thus, the diamine derivative of a polyethylene glycol could be used. Low molecular weight segments of amine containing monomers could be used, such as oligolysine, oligoethylene amine, or oligochitosan. Low molecular weight linking agents, as described below, could have hydroxyl functionality, amine functionality, or both. Use of amines will impart charge to the polymerized matrix, because the reaction product of an amine with an isocyanate is generally a secondary or tertiary amine, which may be positively charged in physiological solutions. Likewise, carboxyl, sulfate, and phosphate groups, which are generally not reactive with isocyanates, could introduce negative charge if desired. A consideration in selecting base polymers, particularly other than PAOs or others that react only at the ends, is that the process of adding the reactive groups necessarily requires adding reactive groups to every alcohol, amine, sulfhydryl, phenol, etc. found on the base polymer. This can substantially change the properties, particularly the solubility properties, of the polymer after activation.

Reactive Groups

The base or backbone polymer is then activated by capping with low molecular weight (LMW) reactive groups. In a preferred embodiment, the polymer is capped with one or more LMW polyisocyanates (LMW-PIC), which are small molecules, typically with molecular weight below about 1000 D, more typically below about 500 D, containing two or more reactive isocyanate groups attached to each hydroxyl, amine, etc of the base molecule. After reaction of the LMW-PIC with the backbone, each capable group of the backbone polymer has been reacted with one of the isocyanate groups of the LMW-PIC, leaving one or more reactive isocyanates bonded to the backbone polymer via the PIC. The LMW-PIC are themselves formed by conjugation of their alcohols, amines, etc. with suitable precursors to form the isocyanate groups. Starting molecules may include any of those mentioned above as starting molecules for forming PAOs, and may also include derivatives of aromatic groups, such as toluene, benzene, naphthalene, etc. The preferred LMW-PIC for activating the polymer are di-isocyanates, and in particular toluene diisocyanate (TDI) and isophorone diisocyanate, both commercially available, are preferred. When a diisocyanate is reacted with a capable group on the base polymer, one of the added isocyanates is used to bind the diisocyanate molecule to the polymer, leaving the other isocyanate group bound to the polymer and ready to react. As long as the backbone polymers have on average more than two capable groups (hydroxyl, amine, etc.), the resulting composition will be crosslinkable.

A wide variety of isocyanates are potentially usable in the invention as LMW-PICs. Suitable isocyanates include 9,10-anthracene diisocyanate, 1,4-anthracenediisocyanate, benzidine diisocyanate, 4,4'-biphenylene diisocyanate, 4-bromo-1,3-phenylene diisocyanate, 4-chloro-1,3-phenylene diisocyanate, cumene-2,4-diisocyanate, cyclohexylene-1,2-diisocyanate, cyclohexylene-1,4-diisocyanate, 1,4-cyclohexylene diisocyanate, 1,10-decamethylene diisocyanate, 3,3'dichloro-4,4'biphenylene diisocyanate, 4,4'diisocyanatodibenzyl, 2,4-diisocyanatostilbene, 2,6-diisocyanatobenzfuran, 2,4-dimethyl-1,3-phenylene diisocyanate, 5,6-dimethyl-1,3-phenylene diisocyanate, 4,6-dimethyl-1,3-phenylene diisocyanate, 3,3'-dimethyl-4,4'diisocyanatodiphenylmethane, 2,6-dimethyl-4,4'-diisocyanatodiphenyl, 3,3'-dimethoxy-4,4'-diisocyanatodiphenyl, 2,4-diisocyantodiphenylether, 4,4'-diisocyantodiphenylether, 3,3'-diphenyl-4,4'-biphenylene diisocyanate, 4,4'-diphenylmethane diisocyanate, 4-ethoxy-1,3-phenylene diisocyanate, ethylene diisocyanate, ethylidene diisocyanate, 2,5-fluorenediisocyanate, 1,6-hexamethylene diisocyanate, isophorone diisocyanate, lysine diisocyanate, 4-methoxy-1,3-phenylene diisocyanate, methylene dicyclohexyl diisocyanate, m-phenylene diisocyanate, 1,5-naphthalene diisocyanate, 1,8-naphthalene diisocyanate, polymeric 4,4'-diphenylmethane diisocyanate, p-phenylene diisocyanate, 4,4',4"-triphenylmethane triisocyanate, propylene-1,2-diisocyanate; p-tetramethyl xylene diisocyanate, 1,4-tetramethylene diisocyanate, toluene diisocyanate, 2,4,6-toluene triisocyanate, trifunctional trimer (isocyanurate) of isophorone diisocyanate, trifunctional biuret of hexamethylene diisocyanate, and trifunctional trimer (isocyanurate) of hexamethylene diisocyanate.

In general, aliphatic isocyanates will have longer cure times than aromatic isocyanates, and selection among the various available materials will be guided in part by the desired curing time in vivo. In addition, commercial availability in grades suitable for medical use will also be considered, as will cost. At present, toluene diisocyanate (TDI) and isophorone diisocyanate (IPDI) are preferred. The reactive chemical functionality of the liquids of the invention is preferably isocyanate, but may alternatively or in addition be isothiocyanate, to which all of the above considerations will apply.

Methods of Synthesis

The method will be described in reference to a polymeric polyol, but it should be noted that the description is also applicable to a polymeric polyamine, polysulfhydryl, or polyphenol, or combination of these groups. The term "polymeric polyol" is used herein to also encompasses polymers containing such groups in addition to, or in place of, hydroxyl groups, unless otherwise stated, or unless inherently not possible.

The objective in the synthesis is to take a backbone polymer with two or more hydroxyl groups (a polymeric polyol) (or other derivatizable groups) and convert it into a reactive polymer in which the reactive groups each carry an active isocyanate group. The synthesis is preferably accomplished without addition of solvents, or of catalysts. A preferred method of adding an isocyanate group to every alcohol is to mix an excess of a di-isocyanate with the base polymer. For example, mixing ethylene diisocyanate (an example of a LMW-PIC) with $R(OH)_n$ yields $R[OC(=O)NHCH_2CH_2N=C=O]_n$, which is a poly-isocyanate polymer with $\underline{n}$ pendant isocyanate groups. This is typically accomplished by slow addition of the LMW-PIC to the polymer at elevated temperatures under nitrogen sparging, to improve reaction rate and to remove the water generated by the reaction.

Physical Properties of the Product

The polymerizable materials of the invention are typically liquids at or near body temperature (i.e., below about 45 deg. C.), and preferably are liquid at room temperature, ca. 20-25 deg. C., or below. The liquids are optionally carriers of solids. The solids may be biodegradable or absorbable. The liquid polymerizable materials are characterized by polymerizing upon contact with tissue, without requiring addition of other materials, and without requiring pretreatment of the tissue, other than removing any liquid present on the surface(s) to be treated. A related property of the polymerizable materials is that they are stable for at least 1 year when stored at room temperature (ca. 20-25 degrees C.) in the absence of water vapor. This is because the material has been designed so that both the reaction that polymerizes the polymers, and the reactions that optionally allow the polymer to degrade, both require water to proceed.

In contrast to previous formulations, the polymeric polyisocyanates contain a low residual level of low molecular weight (LMW) polyisocyanates (PIC). For example, the final concentration of LMW-PIC isocyanate groups in the formulation, expressed as the equivalent molarity of isocyanate groups attached to LMW compounds, is normally less than about 1 mM (i.e., 1 mEq), more preferably less than about 0.5 mEq and most preferably less than about 0.4 mEq. However, it is preferred that the level of LMW isocyanate groups be finite and detectable, for example greater than about 0.05 mEq, and more preferably greater than about 0.1 mEq. It is believed that having a low but finite level of LMW-PIC molecules tends to promote adherence between the applied polymer formulation and the tissue being treated. However, decreased levels of LMW-PIC may tend to decrease tissue irritation during application and cure of the liquid polymer preparation. It is believed that the range of about 1 mEq to about 0.05 mEq is approximately optimal. In situations requiring tissue adherence in the presence of significant biological fluid, or in adherence to difficult tissues, greater levels of LMW-PIC isocyanate groups may be preferred.

Swellability

The active prepolymers of this invention may form intertwined polymer chains after reaction that may change their intertwined geometry under action by fluids within the body. In particular, one or more components may cause the formed polymeric material, whether as coating, adhesive, or solid, to swell. Swelling may have several consequences, and can be controlled. In one mode, swelling can lead to subsequent break-up (physical disintegration) of an implant or other final form, rendering the entire implant absorbable. Or, one or more of the components may dissolve in the body rendering the remaining components absorbable. (Dissolvable materials could be added as solids, or as nonreactive polymers diluting the reactive components.) Or, one or more components may be biodegradable rendering the remaining components absorbable. For example, liquids of the present invention containing a polyethylene/polypropylene random coblock polyol capped with polyisocyanate are capable of forming elastic gels with water content as high as 90%. When these polyethylene/polypropylene polyols are esterified with a carboxylic acid and reacted with a trifunctional molecule such as trimethylolpropane, or alternatively when the trifunctional molecule is esterified and reacted with diols of polyethylene/polypropylene, useful activated polyols are formed. These polyols, when end capped with a polyisocyanate are capable of forming gels or solids in a living organism that decrease in volume and strength over time.

However, the ratio of propylene oxide to ethylene oxide can be varied, and the two monomers can be polymerized into block copolymers, random copolymers, or graft copolymers. These types are commercially available. While the ethylene oxide groups tend to absorb water, and so to swell the crosslinked material formed in the body, the propylene oxide groups are less hydrophilic, and tend to prevent swelling in aqueous fluids. Thus, the degree of swelling of the polymerized material in water can be controlled by the design of the reactive polymers. Another route of swelling control is by incorporation of non-PAO groups, such as aliphatic or aromatic esters, into the polymer (as, or in addition to, esters used to confer degradability.)

The prepolymer of the present invention is formed by capping the polyols (as backbone polymer) with polyisocyanate, preferably a diisocyanate. However, suitable isocyanates have the form $R(NCO)_x$, where x is 2 to 4 and R is an organic group. Another approach to creating an in situ polymerizing liquid that biodegrades in the body is to graft the polyol onto a biodegradable center. Suitable polymers for inclusion as center molecules are described in U.S. Pat. No. 4,838,267. They include alkylene oxalates, dioxepanone, epsilon-caprolactone, glycolide, glycolic acid, lactide, lactic acid, p-dioxanone, trimethylene carbonate, trimethylene dimethylene carbonate and combinations of these.

The center molecule may be a chain, a branched structure, or a star structure. Suitable star structures are described in U.S. Pat. No. 5,578,662. Isocyanate capped alkylene oxide can be reacted with these molecules to form one or more extended chains. The ends of these chains can therefore participate in crosslinking with other centers or bond to tissue.

Center molecules such as those listed above will form rigid solids upon polymerization. Therefore, it is generally more useful to ensure at least 80% alkylene oxide is in the final polymerized structure. Furthermore, the alkylene oxide should be comprised of at least 70% ethylene oxide.

These criteria ensure that the polymerized product is flexible enough to prevent stress localization and associated tissue bond failure. Furthermore, star molecules in general will not be preferred since they contain numerous branches. More numerous branching of the center molecule is associated with higher liquid viscosity. Furthermore, highly branched prepolymers will form polymerized products more slowly and with higher modulus. For example, U.S. Pat. No. 5,578,662 quotes a cross-linking reaction time of 5 minutes to 72 hours. Both of these characteristics are undesirable when the prepolymer is intended as a surgical adhesive or sealant.

Absorbable Compositions and Particulate Additives

Absorbable prepolymer systems can be composed of discontinuous (solid) and continuous (liquid) parts. The solid part may be absorbable or may not be absorbable. One of the simplest forms of an absorbable implant is one that mechanically breaks into small pieces without appreciable chemical modification. Fracture of an implant can be seeded or propagated by the placement of hard centers in the polymer during formation.

Mixing the liquid polymer of the present invention with calcium triphosphate particles will after exposure to fluids or tissue polymerize into an elastic solid containing an inelastic particulate. Movement of the surrounding tissue will deform the elastic implant. Since the particulate cannot deform, stress will localize around these centers and cracks will begin to propagate from these centers. In this way, the rate of disintegration and size of the disintegrated parts can be controlled by varying the particulate size, the modulus of the formed continuous polymer, and the density distribution of the particulate.

Non-absorbable solids are well known and include, as examples and without limitation, calcium triphosphate, calcium hydroxylapatite, carbon, silicone, Teflon, polyurethane, acrylic and mixture of these. Absorbable solids are well known and include, as examples and without limitation, glycolic acid, glycolide, lactic acid, lactide, dioxanone, epsilon-caprolactone, trimethylene carbonate, hydroxybutyrate, hydroxyvalerate, polyanhydrides, and mixtures of these.

Other absorbable prepolymer liquids can be composed of two continuous mechanically mixed parts. For example, one part may be absorbable and the other not. Consequently, the absorption of one part results in the mechanical disintegration or weakening of the implant. Absorbable components may include liquid forms of cellulose ether, collagen, hyaluronic acid, polyglycolic acid, glycolide and others well known in the art. These systems are not excluded in the present invention, but are also not preferred for the reasons stated above.

Typical Polymer Structures

There are several ways in which the above-recited steps can be used to obtain a liquid reactive polymer system useful in the invention. In a very simple system, a polymeric polyol with a number of end groups on average greater than two is treated with a slight excess of a LMW-PIC, such as toluene diisocyanate. The reaction product is formed under nitrogen with mild heating, preferably by the addition of the LMW-PIC to the polymer. The product is then packaged under nitrogen, typically with no intermediate purification.

A preferred biodegradable polyol composition includes a trifunctional hydroxy acid ester (e.g., several lactide groups successively esterified onto a trifunctional starting material, such as trimethylolpropane, or glycerol). This is then mixed with a linear activated polyoxyethylene glycol system, in which the PEG is first capped with a slight excess of a LMW-PIC, such as toluene diisocyanate. Then the activated polymer is formed by mixing together the activated polyoxyethylene glycol and the lactate-triol. Each lactate triol binds three of the activated PEG molecules, yielding a prepolymer with three active isocyanates at the end of the PEG segments, and with the PEG segments bonded together through degradable lactate groups. In the formed implant, the lactate ester bonds gradually degrade in the presence of water, leaving essentially linear PEG chains that are free to dissolve or degrade. Interestingly, in this system, increasing the percentage of degradable crosslinker increases rigidity, swell and solvation resistance in the formed polymer.

Other polyol systems include hydroxy acid esterified linear polyether and polyester polyols optionally blended with a low molecular weight diol. Similarly, polyester and polyether triols esterified with hydroxy acid are useful. Other polyol systems include the use of triol forming components such as trimethylolpropane to form polyols having three arms of linear polyether chains.

Examples of Polymer Synthesis

NCO-terminated prepolymers were prepared by mixing each deionized, dried polyether polyol with each polyisocyanate and reacting them at 60° C. for 6 hours to 3 days.

Example 1: A tri-functional polyether polyol was formed by reacting a PE/PO 80:20 random copolymer having an average MW of 2600 with BASF Luparnate T80-1 (80:20 2,4- and 2,6-toluenediisocyanate) and trimethylolpropane (1-5%) to obtain a NCO-terminated hydrophilic prepolymer having a free NCO content of 3%.

Example 2: A tri-functional polyether polyol was formed by reacting a PE/PO 80:20 random copolymer having an average MW of 2600 with IPDI and trimethylolpropane (1-5%) to obtain a NCO-terminated hydrophilic prepolymer having a free NCO content of 1.5%.

Example 3: A tri-functional polyether polyol was formed by reacting a PE/PO 80:20 random copolymer having an average MW of 2600 (30-20%) and polyethylene glycol of 1000 MW (30-50%) with IPDI (23-39%) and trimethylolpropane (1-5%) to obtain a NCO-terminated hydrophilic prepolymer having a free NCO content of 1.5%.

Example 4: A tri-functional polyether polyol was formed by reacting a PE/PO 80:20 random copolymer having an average MW of 2600 (30-20%) and polyethylene glycol of 1000 MW (30-50%) with BASF Luparnate T80-1 (80:20 2,4- and 2,6-toluenediisocyanate) (23-39%) and trimethylolpropane (1-5%) to obtain a NCO-terminated hydrophilic prepolymer having a free NCO content of 1.5%.

Example 5: A tri-functional polyether polyol was formed by reacting a PE/PO 80:20 random copolymer having an average MW of 2600 (5-10%) and polyethylene glycol of 1000 MW (45-70%) with BASF Luparnate T80-1 (80:20 2,4- and 2,6-toluenediisocyanate) (23-39%) and trimethylolpropane (1-5%) to obtain a NCO-terminated hydrophilic prepolymer having a free NCO content of 1.5%.

Example 6: A tri-functional polyether polyol Voranol CP 1421 average MW of 1421 was reacted with BASF Luparnate T80-1 (80:20 2,4- and 2,6-toluenediisocyanate) (23-39%) to obtain a NCO-terminated hydrophilic prepolymer having a free NCO content of 3.1%.

Example 7: A tri-functional polyether polyol Voranol CP 1421 average MW of 1421 was reacted with BASF Luparnate T80-1 (80:20 2,4- and 2,6-toluenediisocyanate) (23-39%) to obtain a NCO-terminated hydrophilic prepolymer having a free NCO content of 3.1%.

Devices

A device of the invention can be prepared as is common in the art from a number of different forms and can consist of a single instrument with multiple internal parts or a series of instruments that can be replaceably and sequentially inserted into a hollow fixed instrument that guides the operational instruments to a selected location in or adjacent to an annular fissure, or other site in the spine in need of repair. A detailed description of an entire apparatus or series of apparatuses for each instance should not be necessary to enable those skilled in the art to make a device for, or to practice, the present invention, since most of the individual components are conventional. The method of the invention can be accomplished with endoscopic instruments, automated surgical systems, or any system with structural parts that function as set forth herein.

1. The Injector

Figure 2:
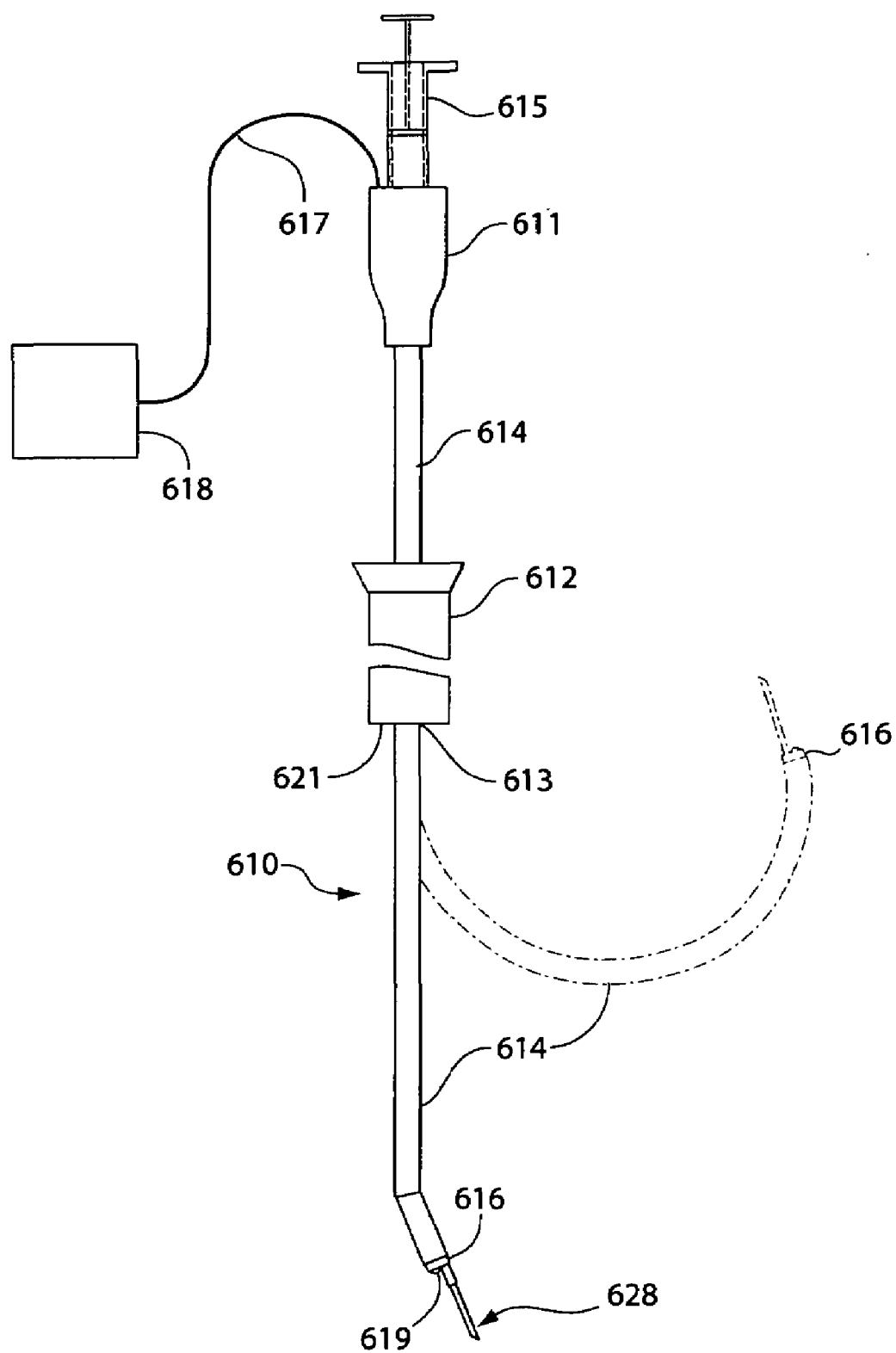
FIG. 2 is a plan view of an introducer and an instrument of the invention in which solid lines illustrate the position of the instrument in the absence of bending forces and dotted lines indicate the position of the distal portion of the instruments would assume under bending forces applied to the intradiscal section of the instrument.

A fundamental device of the invention is an injector, which applies the adhesive polymer or bulking agent to the site. An example of an injector 610 useful in the invention is shown in a schematic way (not to scale) in FIG. 2. The device illustrated is constructed in the same general manner as an intravascular catheter, although it may be considerably shorter in overall length. FIG. 2 shows the handle 611, which holds a catheter-like compound tube 614, which in this embodiment encloses an injection lumen (not visible) terminating at distal tip 616, and an optical fiber 617 supplied with visualization device (light source and viewing screen) 618. The injection lumen connects to a port near to or within the handle 611 for connecting a polymer source 615, which as illustrated can be a syringe, but could instead be a pump. The tube 614, when being introduced into the patient, passes through the lumen 613 of an introducer 612. The introducer 612 can be as simple as a hollow needle. An introducer can simply consist of a hollow needle device or a combination of a simple exterior cannula that fits around a trocar. The goal is to place a hollow tube through skin and tissue to provide access into the annulus fibrosus. More complex variations exist in percutaneous instruments designed for other parts of the body and can be applied to design of instruments intended for disc repairs. The distal end 621 of the introducer will typically be inserted into tissue until it lies at a location into which material is to be injected. The distal tip 616 of the tube 614 has a viewing port 619 connected to the fiber optic 617 or equivalent, and a needle tip 628 connected via the injection lumen to the polymer source 615. A suitable outer diameter for the tube portion 614 is in the range of 0.2 to 5 mm. In the illustrated embodiment, the fiber and the injection lumen are held together inside tube 614, in the manner of an intravascular catheter. However, the fiber or other visualization medium could, in an alternative embodiment, be present in a separate device, for example in a separate needle, in which case the tube 614 would constitute the injection lumen. In another alternative, the tube 614 could end at a fixed distance from the handle, and an injection lumen, carrying the needle tip 628, could be slidably carried within tube 614, to allow its extension into the disc without requiring penetration by the viewing system.

An important optional feature of the injector is the ability to bend the tube 614 during introduction into the spinal disc. This is schematically illustrated in FIG. 2 by a dotted outline of the tube 614 and the distal end 616. A number of methods are known, and can readily be found in the literature, for making a bendable injection device. A simple method is to include a wire or other connector extending from the handle 611 to the tip 616. When the wire is effectively shortened, for example by pulling or twisting, then the tube 614 and the tip region 616 are bent to be at an angle with respect to the handle 611, preferably forming a curve, as illustrated. Typically, the wire is confined to one side of the tube 614 (i.e., off-center), to cause bending to occur in a predictable direction with respect to the handle 611. Alternatively, wires can be paired, as is known in the control of catheters. Instead or in addition, all or part of the tube 614 may be prepared to have an elastic bend, which can be straightened to allow passage through the introducer 612, but which will re-assume a bent or curved configuration inside the disc. Other options for bending the tube can be adapted from the catheter art.

Visualization, which is preferred but not required, may be by direct optical imaging, as illustrated above, but may instead or in addition be by other techniques. Many suitable techniques are known, including ultrasound, fluoroscopy, and light scattering or timed optical pulses ("optical tomography"). If a pump is used for injection, any type of pump can be used that can deliver small volumes in a predictable way. This can be accomplished, for example, by small volume piston pumps or syringe pumps; by pressurization of a reservoir; by peristaltic pumps and similar devices; and by gravity feed.

Control of pressure and/or delivery volume can be important. Control of injection can be provided by placing a pressure transducer in a suitable location. With pumps, a pressure sensor can be placed on or in the tube, or at the tip. With a syringe, a pressure-sensitive pad can be placed on the proximal end of the plunger, as well as on the tube or in the tip. A pressure sensor can be coupled to a display, or a gauge, and/or can be coupled to a microprocessor for automatic or semiautomatic control. In the later case, the variance of pressure with time can be used to help decide when injection has been sufficient.

The injection of the polymer can be used to achieve several objectives, of which one or all may be used in a particular procedure. The polymer can be used to form an adhesive. This is accomplished by depositing a relatively thin layer of polymer on a surface, or more typically between two surfaces. The surfaces can be two layers of tissue, or a layer of tissue and a layer of a prosthetic. The polymer can also be used to form a coating, when there is space between a surface and another surface. For example, with care, a coating layer could be deposited on the inner surface of the annulus after partial or complete removal of a nucleus. The polymer can also be used to form a bulk deposit. In the context of treatment of the spine, this will normally be accompanied by contact of the polymer with surfaces, to which the adhesive polymer will tend to bond.

The injector may include one or more additional sensor and delivery lumens. It may further comprise extraction means for removing tissue, particularly in the nucleus, to help close a fissure in the annulus.

In the procedures described herein, it is advantageous for the adhesive material to enter into the interstices between the fibrous structures of the annulus, thereby becoming mechanically incorporated into the fibrous structure to increase the holding strength of the adhesive/annulus combination. This may be particularly important in annulus repair and in securing a disc nucleus implant within the annulus.

Other devices are useful in the practice of the invention and will be described in particular contexts below.

Exemplary Uses

The following examples of how the polymers and devices can be used are supplied to clearly illustrate the uses of the invention.

Herniated Disc Repair

The paramedial retroperitoneal procedure for exposing the spine should be used when the herniation, or a substantial portion of the herniation impinges on the trunk of the spinal nerve. In this approach entry into the disc is anterior to the defect. When the herniation is posterior lateral and impinging on one of the spinal nerve branches, the lateral retroperitoneal approach may be preferred. The entrance to the disc is preferably opposite the disc defect.

When the herniation is anterior of lateral the posterior lateral approach is preferred. The choices from this approach are through the lamina or between the lamina and the adjacent vertebral body. In going between the lamina and the next vertebral body an expandable trocar of considerable robustness will be required to increase the opening on this approach. Where the approach is through the bone of the lamina, the entrance aspect is substantially perpendicular to the plane of the disc. In such an approach, some of the techniques described below will not work.

Figure 3:
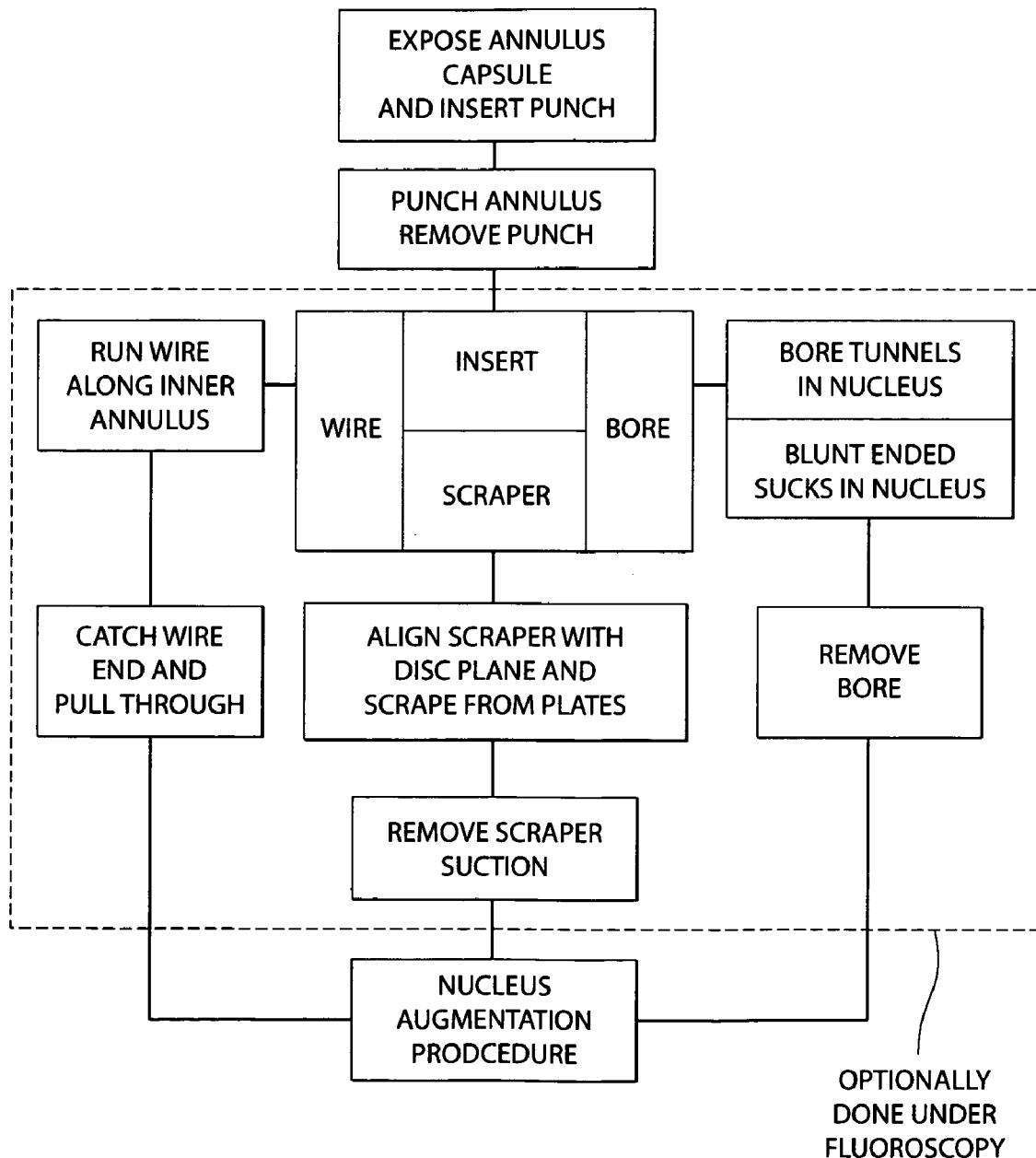
FIG. 3 is a flow diagram of a procedure for modifying the disc nucleus.

Treatments for disc herniation of the present invention will typically include shaping, cutting, or removing portions of the nuclear material, or all of it. For example, a generalized flow diagram for augmenting a damaged disc nucleus is given in FIG. 3. In each case, the annulus is exposed, and a hole is punched into the annulus. (Each technique will be described below). Three pathways can be taken from this point. Moving inside the dotted box, one of a wire, a scraper or a bore is inserted. If a wire, then, listed on the left, the wire is run along the inner annulus, completing a loop. The wire is caught, forming a loop; the wire is pulled through the nucleus, creating a cut in the disk plane. Then this flat cut is used as the locus for a nucleus augmentation procedure.

Another approach to preparing the nucleus for augmentation is shown in the center. A scraper is inserted into the nuclear space. The scraper is aligned with the disc plates, and disc material is scraped from the plates. The scraper is removed, and suction is applied to remove loose or friable nucleus materials. Then a nucleus augmentation procedure is begun. On the right, another approach involves the use of a bore to create tunnels in the nucleus. The debris is removed if required, and the nucleus is ready for augmentation.

Figure 4A:
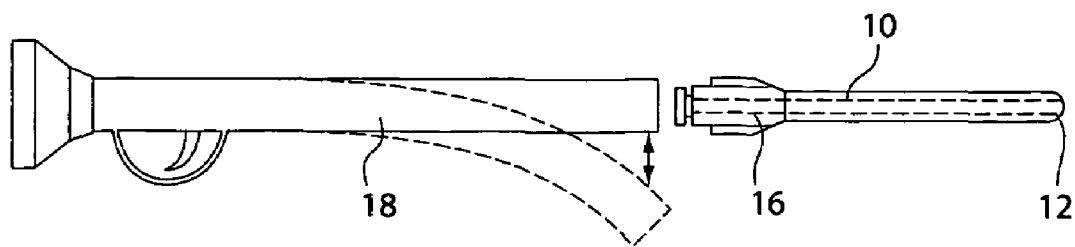
FIG. 4a, b is a plan view of an approach to the disc nucleus using a hollow needle to place a guidewire.
Figure 4B:
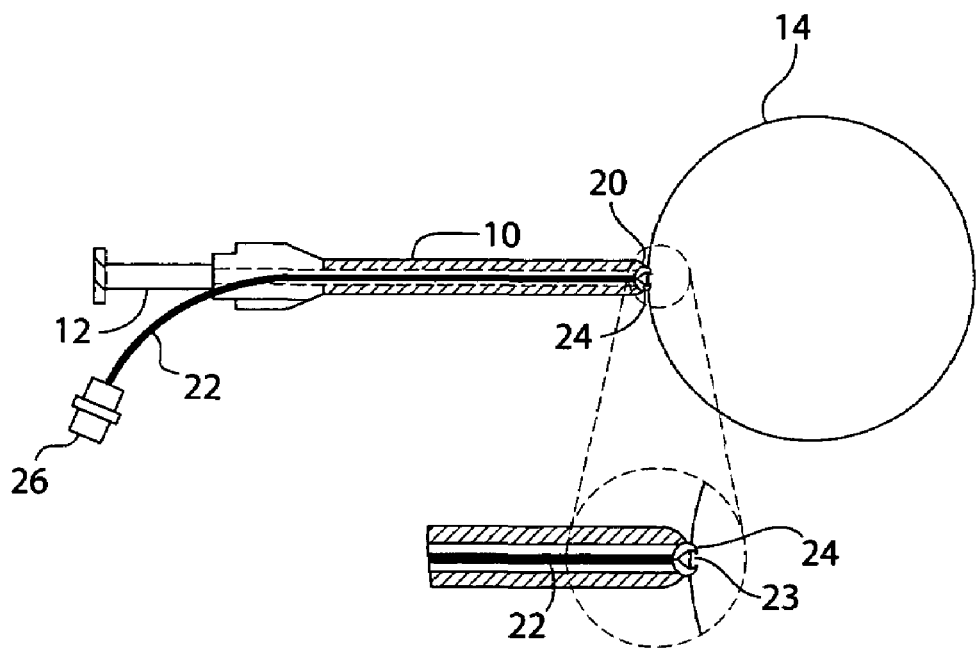
FIG. 4c is a plan view of a trocar obdurator approaching the disc over the guidewire.

These repair techniques are described in more detail in FIGS. 4 through 7. Referring to FIG. 4, in one preferred embodiment, a blunt, hollow needle 10 combined with a stylet 12 is used to dissect the overlying tissue from the skin down to the disc capsule 14 (FIG. 4b, middle). The needle may, for example, have an external diameter of 0.050 inch (1.25 mm) and internal diameter of about 0.038 inch (0.95 mm). The needle 10 has a proximal end fitted with a luer connection 16 that is connected to a steerable body 18, such as a syringe (FIG. 4a, top).

After insertion of the needle 10, with the distal end 20 of the needle resting on the surface of the disc capsule 14, the stylet 12 is removed and guidewire 22 is introduced through the needle lumen (FIG. 4b). Guidewire 22 has tines 24 on its distal end 23 capable of engaging tissue (FIG. 4b inset). Guidewire 22 also has a graspable member 26 having sufficient diameter or length to provide sufficient torque to the guidewire 22 to engage tines 24. With the distal end 23 of guidewire 22 resting on the disc capsule surface 14, axial pressure is applied along with rotational motion at the proximal end 26 so as to fixably attach the guidewire 22 to the capsule surface 14. Once guidewire 22 is engaged then detachable member 26 is removed and needle 10 is removed.

Figure 4C:
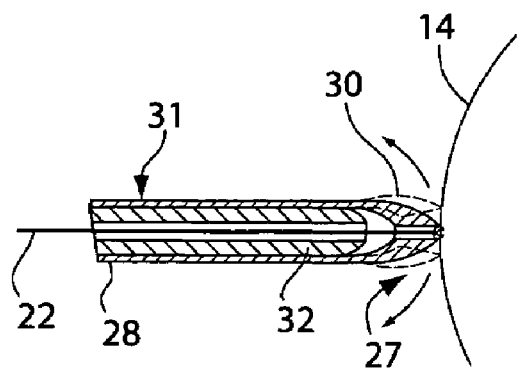

Referring to FIG. 4c (bottom), in an alternative embodiment, dissection through tissue to access the disc capsule 14 is instead performed using a trocar 28 with blunt, tapered distal end 27. The trocar 28 is preferably an expandable trocar, having an expandable, tapered distal end 27 of internal diameter of 0.050 inch (1.25 mm), for example, and a proximal end 31 having initially a larger internal diameter, such as 0.25 inch (6.25 mm). The trocar 28 is fitted with a hollow stylet 32 with internal diameter 0.050 inch and outer diameter 0.25 inch such that it can be slidably advanced along guidewire 22. Trocar 28 fitted with stylet 32 is advanced along guidewire 22 until reaching disc capsule surface 14. During insertion of trocar 28 tension is applied to guidewire 22 sufficient to control the direction of trocar 28. Stylet 32 is removed. Trocar 28 may include an expandable sleeve which may be expanded to retract surrounding tissue and increase access space to the disc. For example, the expandable sleeve may expanded, using one or more stylet or obdurator, from the initial 0.05 inch (ca. 1.25 mm), schematically shown at point 30, to as much as 10 to 12 mm (3/8 to 1/2 inch) to provide access to and visualization of the disc.

Figure 5:
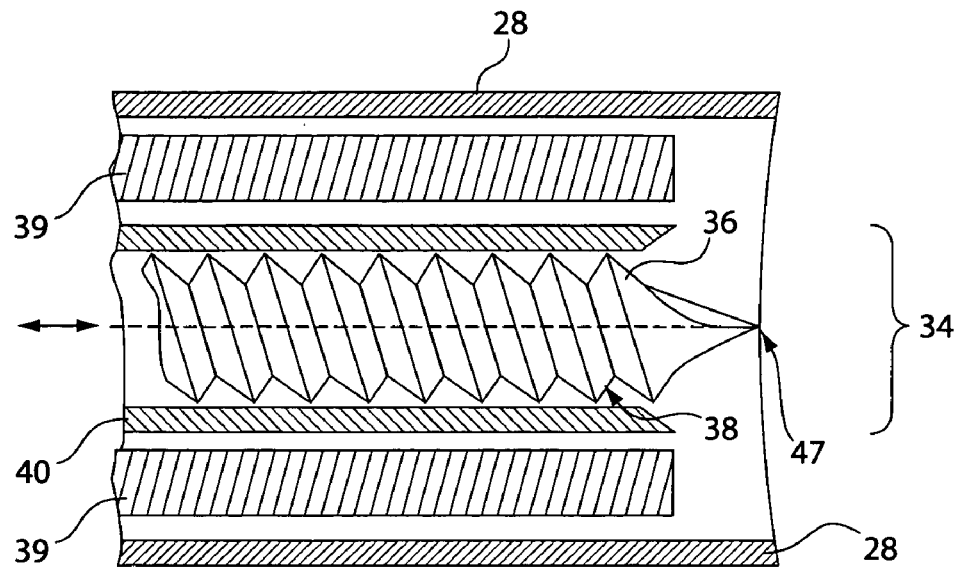
FIG. 5 is a cross-section view of a cannula with an annulus punch placed therethrough.
Figure 5A:
Figure 5B:
Figure 5C:
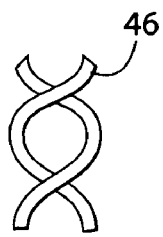
Figure 5D:
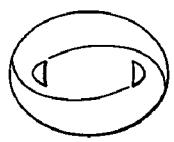

Referring to FIG. 5, an annulus punch, labeled generally as 34, is shown. The annulus punch may be provided in various diameters. Annulus punch 34 is comprised of engaging member 38 (corkscrew) and cutting hull 40. Engaging member 38 has an outer diameter matching the inner diameter of cutting hull 40 such that member 38 is slidable within hull 40. The distal tip 47 of engaging member 38 may have a fine screw surface 42 as in FIG. 5A, or engaging and cutting tines 44 as in FIG. 5B, or an open helical configuration 46 as shown in FIG. 5C. The body of the engaging member 38 can have a standard screw profile, or a thin profile as shown in FIG. 5D. Typically the outer diameter of cutting hull 40 will be in the range of 0.1 to 0.25 inch (2.5 to 6.25 mm). If the outer diameter of punch 34 is less than the inner diameter of trocar 28, then a stylet 39 is used to match these diameters by filling the space between them, and guidewire 22 of FIG. 4c is not used. Alternatively, no stylet is used and guidance is provided solely by the guidewire. In this case, punch 34 has a concentric bore 36 running through its center with a diameter matching that of the outer diameter of guidewire 22 (of FIG. 4c).

Figure 6:
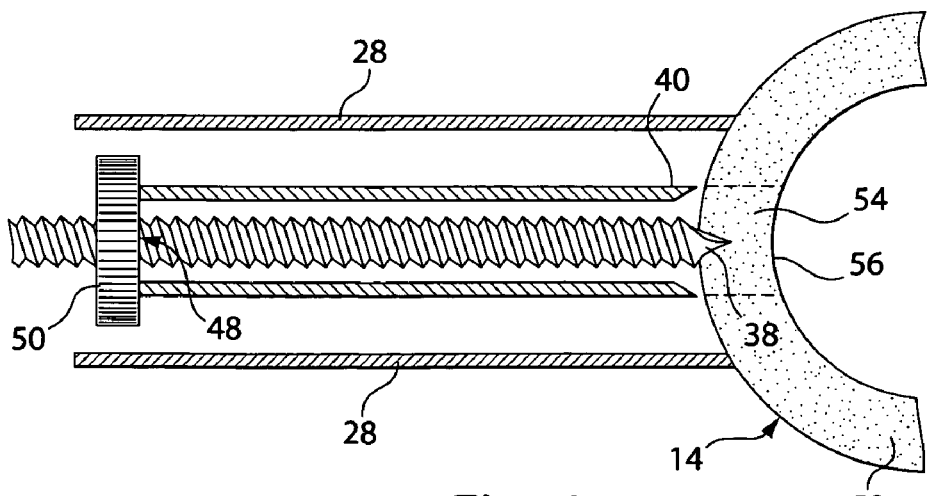
FIG. 6 illustrates the annulus punch penetrating the annulus.

Referring to FIG. 6, one way to use the apparatus of FIG. 5 to remove a core through the annulus is shown. Here, proximal end 48 of engaging member 38 has a slide stop 50, suitable for grasping, that forces cutting hull 40 with it as engaging member 38 is advanced through tissue. Slide stop 50 is adjusted to the surface of the proximal end of cutting hull 40 when the distal end of engaging member 38 is in contact with capsule surface 14. When engaging member 38 is engaged with capsule surface 14, slide stop 50 is turned so as to advance engaging member 38 through the annulus 52. During advance, cutting hull 40 cores a cylindrical volume 54 of annulus 52. Once punch 34 has traversed annulus 52, a noticeable drop in turning resistance is felt at slide stop 50. Turning is stopped, and punch 34 is drawn out of trocar 28. This action removes the cylindrical core 54, detaching from the nuclear surface 56.

Figure 7A:
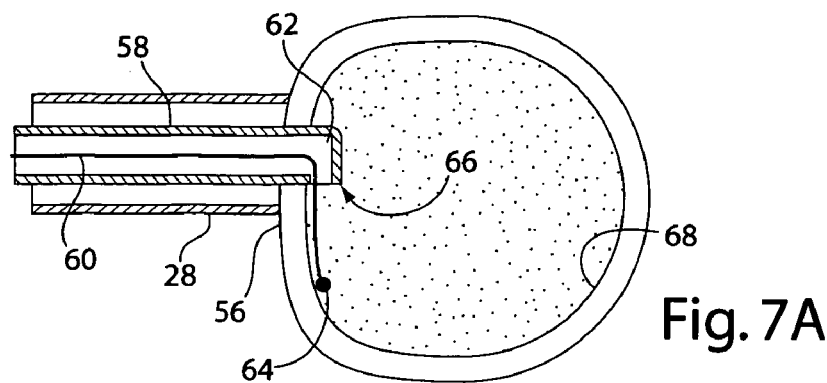
FIGS. 7A-7D are illustrations of cutting wire placement within the disc.
Figure 7B:
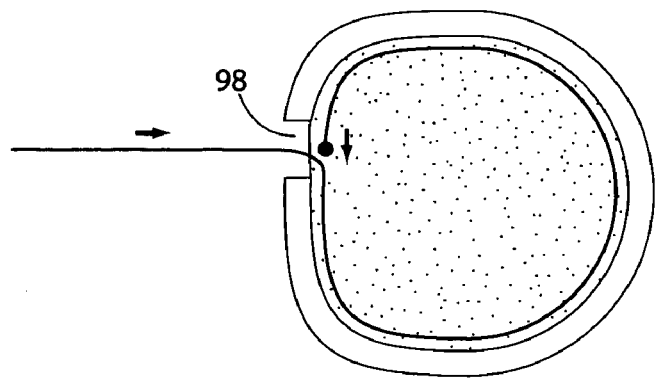

Referring now to FIGS. 7A-D, in FIG. 7A one embodiment of a catheter 58 comprising wire member 60 and side-directing distal end 62 is introduced with or without stylet through trocar 28 to nucleus surface 56. Wire member 60 has blunt end 64 which can pass through the aperture 66 of side directing end 62. With pressure, wire member 60 is advanced through aperture 66 and along the inner annulus surface 68. Wire 60 is sufficiently stiff to cause aperture 66 to force blunt end 64 along inner annular surface 68, while the blunt end 64 prevents the wire 60 from perforating the surface 68. Wire 60 is advanced until blunt end 64 returns to the distal end 62 of catheter 58. This can be detected by a combination of distance of wire pushed, and fluoroscopy. Then, pressure is applied to wire 60 while a pull force is applied to catheter 58 such that catheter 58 is removed leaving wire 60. The result is shown in FIG. 7B. There is now an opening 98 in wall 56 of the annulus.

Figure 7C:
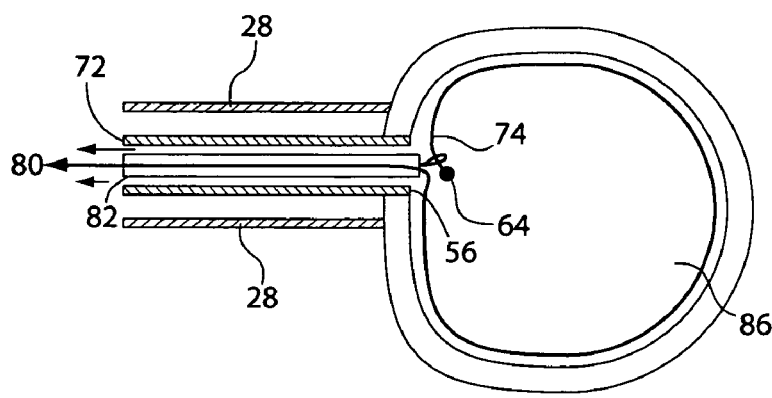
Figure 7D:
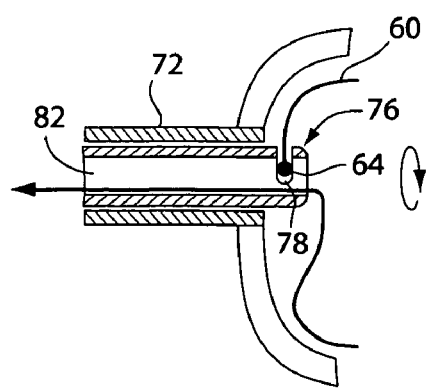

Next, as shown in FIG. 7C, second catheter 72, with or without stylet, is advanced through trocar 28 until it rests upon nuclear surface 56. Catheter 72 can be hollow with proximally actuated engaging loop 74. Alternatively, as shown in FIG. 7D, catheter 72 has tip 76 with engaging slot 78. In either case, catheter 72 is engaged with wire end 64. In both cases, both proximal wire end 80 and loop end 82 or catheter tip 76 is pulled causing wire 60 to cut a substantially flat plane, labeled 84 in FIG. 8, through substantially all of the nucleus 86. Radiofrequency or other energy may be applied to the wire to enhance the cutting effect.

2. Thickening the Disc

Figure 8:
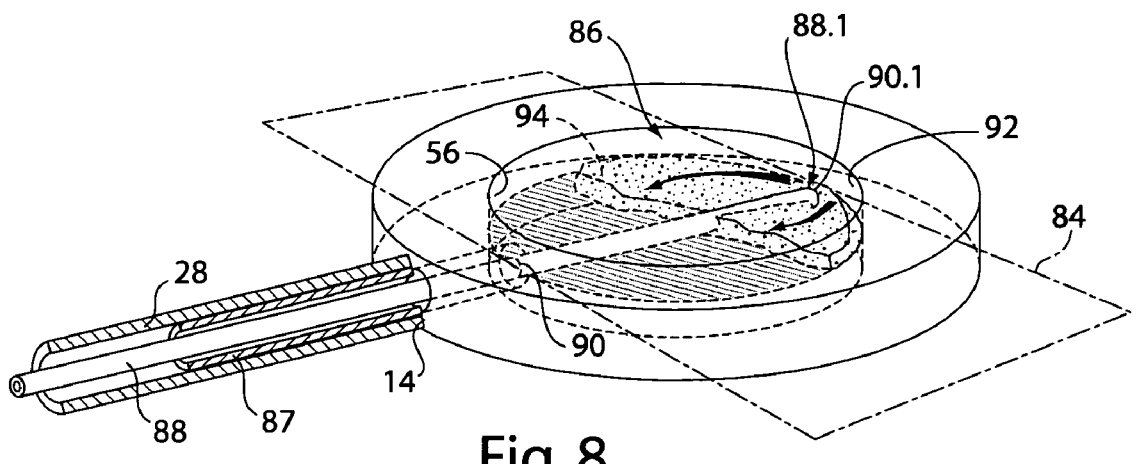
FIG. 8 is a partially sectioned perspective view of a disc with a delivery catheter for delivery of adhesive to the disc nucleus.

Referring now to FIG. 8, nucleus 86 has plane 84 which can be accessed through trocar 28. Any number of delivery systems can be used to deliver tissue adhesive to plane 84. In a preferred example, a stylet 87 is used that fills the space between an introducing catheter 88 and trocar 28. (Catheter 88 may be similar in construction to the injector 610 of FIG. 2, for example.) The stylet 87 is advanced to nuclear surface 56 and distal tip 90 of catheter 88 is advanced through the nucleus via plane 84 to the distal side 92 of the nucleus 86. Dashed lines 88.1 show the catheter after advancement, and label 90.1 shows the tip location after advancement. Then adhesive 94, shown exuding from tip 90. 1, is introduced through catheter 88 to bond and thicken nucleus 86. Adhesive 94 is a liquid and is introduced under pressure, and is localized by stylet 87, which makes a seal at the capsule surface 14. This arrangement is held in place until tissue adhesive 94 solidifies.

This procedure, shown without apparatus in FIGS. 9A, 9B and 9C, repairs a herniated or collapsed disc by returning nucleus 86 to a normal thickness via tissue adhesive and bulking agent pumped into plane cut 84, creating a layer 85 of injected material.

3. Pulling Back A Bulge in the Disc

It may be beneficial to reduce the radius of a herniated disc, especially when the herniation impinges on vessels or nerves by adding to the above procedure several additional steps that either reduce the pressure in the nucleus or actually draw in the annulus wall.

Figure 10A:
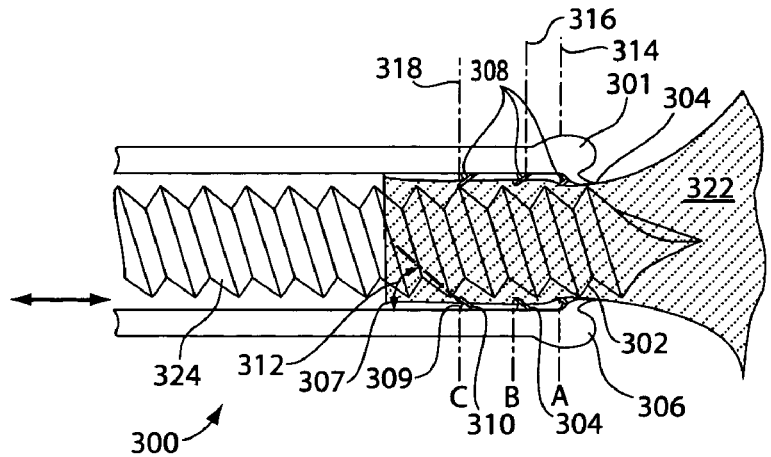
FIG. 10A showing the overall apparatus.
Figure 10B:
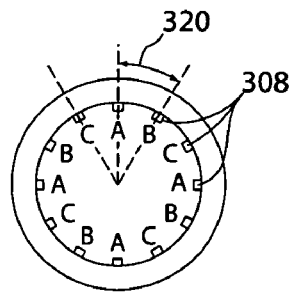
FIG. 10B showing the staggered arrangement of the spines.
Figure 10C:
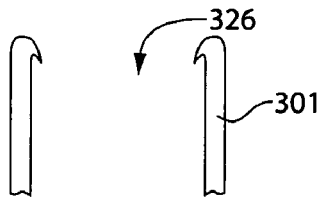
FIG. 10C showing a biased edge as an alternative to spines.

Returning now to FIG. 9, after completing the procedure of FIG. 7 or FIG. 8, an example of additional steps suitable to adjust the annulus wall includes boring radial channels 96 from annulus opening 98 to the inner annulus surface 68 using boring techniques analogous to annulus coring described above. An example of a suitable nuclear bore 300 is described in FIG. 10. It comprises a hollow cutting hull 301, shown in 10A, and internal screw-like grasper 302, the profile of which provides sufficient traction to distort and actively drive nuclear material onto cutting edge 304. Cutting edge 304 does not extend beyond blunt profile edge 306, so that when the bore encounters a substantially solid surface no further cutting occurs. The inner surface of cutting hull 301 can be studded with tines 308 whose sides of greatest surface area 309 are aligned with the axis of cutting hull 301. Additionally, the distal sides 310 of tines 308 are sharp so that when tissue is drawn into hull 301 the tissue is sliced through with minimal resistance. Conversely, the proximal sides 307 of tine 308 are blunt. The tines 308 may be biased proximally at angle 312. As seen in FIG. 10B, the tines may further be staggered along the axis of hull 301 such that tines A form a unit in a single plane 314 of hull 301, from which successive units B and C are arranged on successive planes 316 and 318, and are created by rotating through angle 320. The effect is that when the nuclear material is cored and core 322 and bore 300 are removed, surfaces 309 prevent rotation of core 322 which prevent it from sliding down screw-like grasper 302. Further bias 312, blunt edge 307, and grasper surface 324 prevent axial slippage of the core 322 of nuclear tissue. Alternatively, as shown in FIG. 10C, a biased edge 326 on hull 301 may be substituted for tines 308, or used in addition to them. Although the bore 300 is one example of a device that can remove tissue in a controlled way, other devices capable of such removal can be envisaged.

Returning to FIG. 9E, a multiplicity of nuclear channels 96 can be made from the same annulus opening 98 by tilting trocar 28 at angle 100 in the disc plane. Pressure can be relieved in the nucleus 86 by leaving channels 96 hollow and paving over annulus opening 98 with additional tissue adhesive or suitable mesh coated with tissue adhesive (FIG. 9D). To retract a bulge, or otherwise adjust the profile of the disc, a plurality of flexible catheters 102 may be introduced serially into the nuclear channels 96. A flexible catheter 102 comprises a hollow flexible shaft 104 with biocompatible strings 106 or wires with tissue snaring end 108 detachably localized on the distal end 110 of catheter 102. Biocompatible strings or wires 106 may be porous, such as expanded PTFE or woven stiff threads. First catheter 102 is introduced into a channel 96 until the distal end 108 touches inner annulus surface 68. Then under axial pressure, catheter 102 is twisted to fixably engage tissue snare 108 to inner annulus surface 68. First catheter 102 is left in place to help guide a second catheter 102 to a separate channel 96. When the desirable number of channels are drilled, the hollow flexible shafts 104 of catheters 102 are removed.

Next, catheter 109 is introduced into trocar 28 (FIG. 9F, 9H). Catheter 109 has an inner scalloped or grooved 110 cross section such that when strings 106 are put under tension they naturally fall into the groves 110. Second catheter 112 is introduced into catheter 109. Catheter 112 has a double internal lumen 114 and 115 and outer radius matching the inner radius 116 of catheter 109. Catheters 109 and 112 form a sealable surface 116 against capsule surface 14. The proximal end of catheter 112 has a luer connection 118 (FIG. 9G) connecting to lumen 114 and a port 120 allowing lumen 115 to vent to atmosphere The hernia reduction procedure comprises pulling strings or wires 106 tight so as to reduce bulging of the annulus 68. Tension can be applied differentially to strings 106 to affect a therapeutic annulus shape, as shown schematically in FIG. 9F compared to FIG. 9E. The proximal end of string 106 can be fixably attached to the proximal end of trocar 28 to hold strings 106 in place during the bonding procedure. Second a syringe of tissue adhesive is loaded on luer connection 118 and adhesive, preferably of the type described above, and more preferably fast curing, is advanced down lumen 114 to fill channels 96. Alternatively only the annulus opening 98 need be filled with adhesive. Once the adhesive is cured all catheters are removed from trocar 28. The strings or wires 106 and annulus opening 98 can be planed to smoothness using a planing auger described later in the section titled Nuclear Prosthetic Localization, below.

4. Removal of Disc Material to Treat Herniation

Figure 11A:
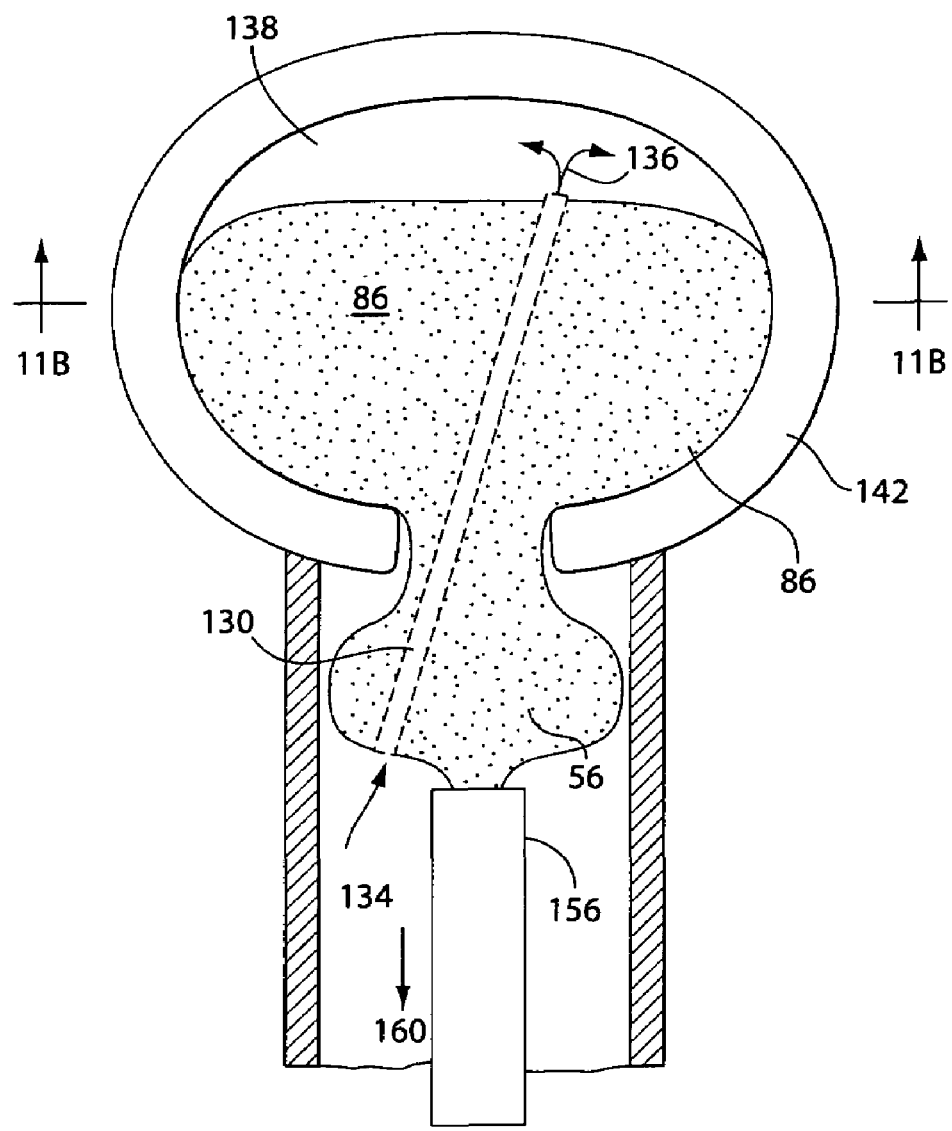
FIG. 11A being a plan view.
Figure 11B:
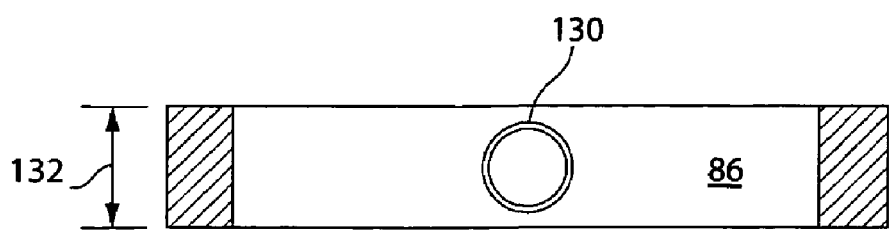
FIG. 11B a cross section.

The examples described above entail leaving the nucleus intact to at least some degree. The methods below describe treatment of disc herniation by removing some or all of the nucleus. Referring now to FIG. 11, a variation on the wire approach can be used to completely separate the nucleus from the annulus. As described above, the nucleus 86 is exposed by coring the annulus. A channel 130 is made through the nucleus 86, for example with the bore of FIG. 10. Channel 130 (delineated by dashed lines) preferably has a cross section of about 10% of the thickness of disc 132, ranging from about 5% to about 20% (see FIG. 11A). The purpose of channel 130 is to allow a suitable fluid medium, coming from a source 160, to flow from first end 134 to second end 136 of channel 130 to fill void 138 as nucleus 86 is removed from annulus 142, for example by aspiration through a catheter 156, or by removal any other means, such as a grasper (not shown.). However, channel 130 is not strictly necessary, and should be avoided if the nucleus 86 is friable. Alternatively, a balloon could be placed in space 138 via passage 130 and be inflated, either as the disc nucleus is removed or by itself to promote disc nucleus removal (not illustrated.)

Figure 12:
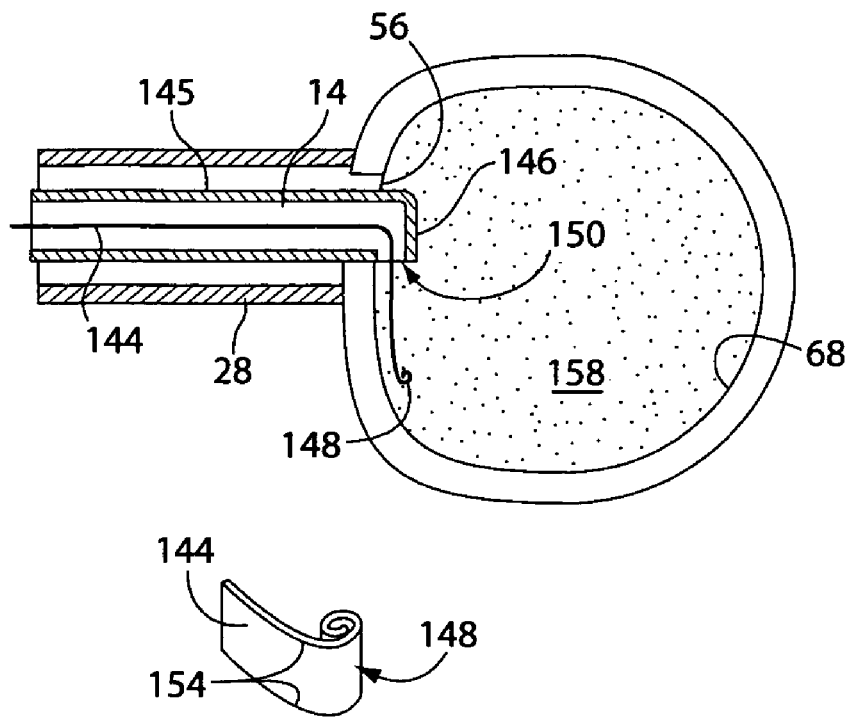
FIG. 12 illustrates blunt dissection of the disc nucleus from the annulus.

Referring to FIG. 12, an alternative is shown. A bore is removed, and catheter 143 comprising ribbon member 144 and catheter 145 with side directing end 146 is introduced with or without stylet through trocar 28 to nucleus surface 56. Wire ribbon member 144 has a blunt end 148 such that it can pass through the aperture 150 of side directing end 152. Additionally, axial edges 154 of ribbon 144 are sharp (see inset). With pressure, ribbon member 144 is advanced through aperture 150 and along the inner annulus surface 68. Ribbon 144 is sufficiently stiff to cause aperture 150 to force blunt end 148 along the inner annular surface 68 without perforating the surface. Ribbon 144 is advanced until blunt end 148 returns to the distal end 146 of catheter 145. Ribbon 144 is then removed by pulling proximally on the proximal ribbon end (not shown). Catheter 145 is removed.

Returning to FIG. 11, subsequently a grasper 156 is placed on nuclear surface 56 and advanced a sufficient distance into the nucleus 86. The integrity of nucleus 86 determines how far one must advance grasper 156. Once nucleus 86 is fixedly attached to grasper 156, grasper 156 is retracted proximally towards 160 to remove the nucleus 158 in one piece. Grasper 156 could be a catheter 156 for aspiration, as illustrated, or could be a screw-like grasper, as in FIG. 10. Alternatively, the ribbon 144 can be inserted first and then channel 130 created. The first sequence is preferred since creation of channel 130 allows the nucleus 158 to distort to accommodate passage of the ribbon 144.

Alternatively, the grasper 156 can be omitted and the ribbon 144 used to remove the nucleus 158. In this case, when ribbon end 154 appears after traversing inner annulus surface 68, hull 145 is removed leaving ribbon 144 in place. Then a loop grasper (not illustrated; analogous to the loop in FIG. 7C) is attached to ribbon blunt end 148 and grasper 160 and proximal ribbon end 154 are both pulled proximally. For use in this technique, ribbon 144 may have its sharp or serrated edges 154 bent at right angles to the ribbon plane to effect a cutting action, separating nucleus from vertebral end plates, as the ribbon is pulled out of the annulus.

Annulus Repair

The present invention provides a minimally invasive method and device for treating discs at selected locations within the annulus fibrosus. In particular, it relates to fixing the fibers of the annulus in a preferred orientation and providing increased rigidity to the annulus by increasing its volume and coupling adjacent layers of the annulus with a polymerizing fluid.

One important consequence of delivering tissue adhesive within the wall of the annulus fibrosus is to increase support and space between vertebral bodies by inflating tissue that is, by virtue of its internal structure, constrained laterally such that the inflating pressure is predominately direct toward the disc plate surfaces. In the unloaded condition, this force can substantially improve intervertebral distances without increasing disc diameter. This improved arrangement is then fixed through polymerization, both by binding adjacent tissue layers and by adding bulk to the annulus. In particular, the invention provides a device that has a distal end that is inserted into the wall of the annulus and accesses the posterior, posterior lateral and the posterior medial regions of the annulus fibrosus in order to repair an annulus at such a location. These and other objects of the invention have been accomplished by the present invention which provides methods for manipulating annulus tissue with and without a fissure or tear in an intervertebral disc, the disc having a nucleus pulposus and an annulus fibrosus, the annulus having an inner wall of the annulus fibrosus.

The method employs an externally guidable intervertebral disc apparatus, or injector. The injector may be generally similar to a catheter, for example as described above in FIG. 3, but any physical arrangement which allows controlled delivery of fluid to a site, optionally accompanied by visualization of the site or its surrounding, is suitable. The procedure is performed with an injector having a distal end, a proximal end, a longitudinal axis, and an intradiscal section at the injector's distal end on which there is at least one functional element. The injector is advanced in the annulus fibrosus in an orientation substantially parallel to the layers of the annulus by applying a force to the proximal end. In the case where the annulus is open, the opening may be sealed with the polymerizing fluid first. The functional element, which may simply be a hollow needle, is positioned at a selected location in the disc by advancing or retracting the injector and optionally twisting the proximal end of the injector. The procedure allows the administration of tissue adhesive to treat annular fissures.

A method of treating an annulus comprises the steps of placing an injector in a plane of the annulus layers and delivering tissue adhesive in sufficient quantity to strengthen and bond two or more adjacent layers. This operation may include filling portions of the nucleus. If the annulus is whole, the fluid may be injected under pressure sufficient to cause the fluid to separate and travel between layers encircling the entire disc before solidifying by polymerization. Once the layers are fully infiltrated, additional pressure will serve to pressurize the space between layers, and the natural adhesiveness between the layers of the annulus directs the inflation pressure substantially in a directions perpendicular to the plane of the disc plates. This generated force then serves to increase the intervertebral distance, preferably to about 10 to 15 mm. This procedure may be enhanced by several unloading methods known in the art, such as adjusting patient position, inserting a balloon in the region of the nucleus and inflating, and various mechanical means for separating the vertebral plates.

It may be advantageous to include various measuring means, for example measuring the fluid pressure inside the delivery device to control the degree of inflation of the annulus. Various imaging means, including fluoroscopy and the transmission of light through the annulus, may be used to directly observe delamination of the layers of the annulus. Furthermore, the procedure may include the use of polarized light or fluorescence or similar imaging methods to directly observe the orientation of the fibers within the annulus, and accordingly direct delivery efforts.

Annulus Augmentation—Example

Figure 13:
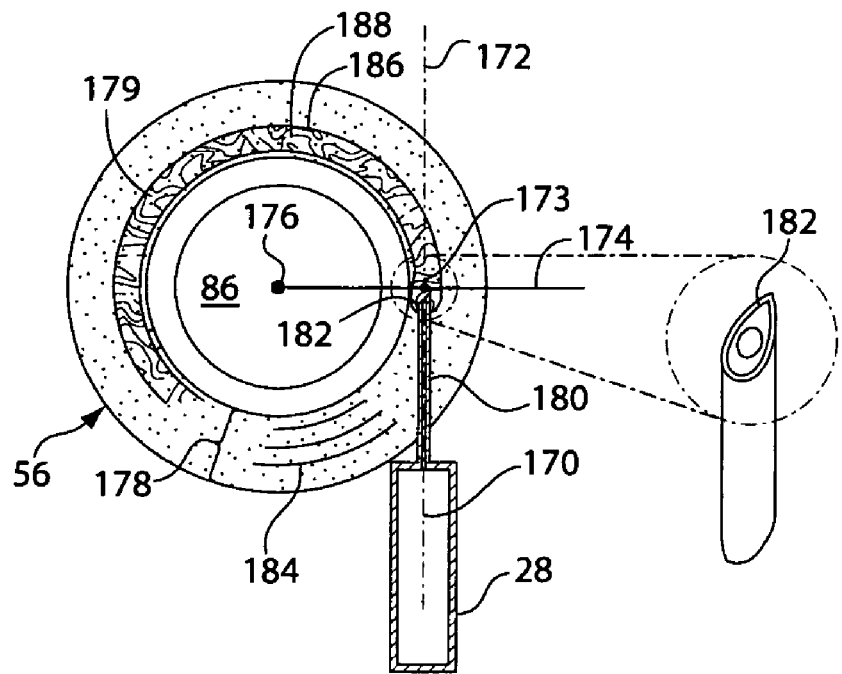
FIG. 13 illustrates augmentation of the annulus with adhesive.

Referring now to FIG. 13, the annulus surface 56 is exposed at a site where the axis 170 of trocar 28 is collinear with a tangent 172 at the point 173 of intersection of trocar axis 170 and a line 174 perpendicular to trocar axis 170 that passes through disc center 176. It should be appreciated that translation of trocar 28 laterally in the direction along line 174 satisfies the above condition but places point 173 at varying depths in the annulus wall 178. A beveled needle 180, flattened at tip 182 along a dimension parallel to line 174, is introduced along trocar axis 170 with the flattened dimension of tip 182 perpendicular to the plane defined by trocar axis 170 and disc bisector 174. Needle 180 is advanced through the annulus wall 178 along tangent 172 until needle tip 182 reaches intersection 173. This positioning can be achieved by estimation or fluoroscopy. This action causes needle 180 to cut through some of the layers 184 of the annulus.

Referring also to FIG. 14A, then the wire or ribbon method previously described is used to delaminate layer 186 from layer 188 of annulus wall 178, thereby forming a pocket 179. Wire or ribbon 190 is left in place. In FIG. 14B, flexible catheter 192 with proximal end 194 with luer fitting 196 is attached to adhesive syringe 198. Flexible catheter 192 is carefully primed with adhesive before introduced into trocar 28. This is done to prevent air injection into the relatively small volume pocket 179 formed in annulus wall 178. Flexible catheter 192 has a beveled but blunt end 200. Flexible catheter 192 may have an external engagement assembly 202 to allow it to be detachably attached to wire 190. (See FIGS. 14B-1 and 14B-2). Once catheter 192 is primed it is attached to wire 190 and introduced into the trocar 28 and advanced to intersection 173.

At this point catheter 192 may be detached from wire 190 by rotational motion 204 (see FIG. 14B-2) and wire 190 removed from the annulus wall 178. Alternatively, the wire and attachment may be left in place to help guide catheter 192. If this alternative is the case, the wire must be removed before adhesive is administered to pocket 179. Alternatively, a balloon on the tip of a catheter may be used to create the delineated space in the annulus wall.

Catheter 192 is then advanced along pocket 179 until catheter tip 200 has circumnavigated the annulus wall 178, or nearly so. Subsequently, pressure is applied to plunger 206 of adhesive syringe 198 and a small volume of adhesive, e.g. 0.01 cc, is dispensed forming plug 210 as shown in FIG. 14c.

Adhesive syringe 198 should be small, for example about 1 cc, so that resistance to injection of adhesive is readily transmitted to the surgeon's hand. The adhesive is then allowed to cure. Then pressure is applied to plunger 206 of adhesive syringe 198 while simultaneously pulling proximally on catheter 192. The rate of catheter extraction should be governed by the resistance to injection felt by the surgeon at plunger 206. It should be noted that dispersal of adhesive along the pocket is a high resistance condition. As catheter 192 is removed resistance to injection drops. As catheter tip 200 passes through the annulus pocket 179 dispersing adhesive, resistance to injection of adhesive will drop noticeably when at locations where pocket 179 intersects an annulus defect 208. When this drop in resistance is noticed, retraction of the catheter 192 is halted and adhesive is injected statically until the defect is filled. Since the portion of pocket 179 is sealed by plug 210 and the body of catheter 192, the pocket 179 can be pressured if desired. The pressure in pocket 179 will tend to pull aneurysms such as 212 toward disc center 176 (wavy arrows) due to hoop stress (double headed arrows, FIG. 14B).

Disc Dimensioning

Sometimes the goal of a nucleus replacement procedure involves the additional step of increasing the distance between vertebral plates (increasing disc thickness) beyond what is achieved by unloading the spinal column. In this case, pressure is introduced into the nuclear region. This has five clinically significant effects: 1) it further separates the vertebral plates and palliates pain associated with nerve damage caused by direct contact between the plate surfaces, 2) it increases the range of spinal movement by allowing the planes of the vertebral plates to be at larger different angles without touching, 3) it provides room for the normal variations in plate spacing due to acute compressive forces, 4) it equalizes the spacing in the treated disc with those of untreated normal discs so as to distribute forces more evenly along the spinal column, and 5) it reduces stress on the various branching elements of the spinal chord by restoring proper spacing between them.

Additionally, there is a morphological effect associated with the microscopic structure of the annulus. The annulus is comprised of concentric layers of tissue. Each layer is comprised of filaments of collagen arranged in sheets with the orientation of the filaments within a sheet aligned along one of two principal directions. The sheets are arranged so that the alignment of fibers alternate in direction, and the angle formed between fibers oriented in one sheet and fibers oriented in an adjacent sheet is substantially greater than zero, and approaches 30-45 degrees in the preferred case. The structural effect is to alternate layers of fibers in a crossing pattern such that the tension in an inner layer of fibers is counter balanced by the tension in an outer layer of fibers such that the layers maintain their respective positions within the annulus resulting in restorative forces counteracting the pressure force in the nucleus which tends to increase the radius of the annulus. The increase in the radius of the annulus is responsible for bulging of the disc, which ultimately leads to disc degeneration and nerve damage.

The process of annulus degeneration is accelerated when the radius of the annulus is increased. The effect of reducing disc thickness along with an increase in disc radius serves to reduce the angle between fiber layers. As the fibers become substantially more parallel, i.e., less crossing, the tension in the fibers is less effective in maintaining the radius of the annulus and distension occurs. Consequently, the restorative forces necessary for maintaining proper disc radius and preventing aneurysm or rupture can be realized in part by restoring (increasing) the distance between vertebral body plates.

In the cases where the annulus has ruptured and nucleus material has extruded outside of its normal confinement within the annulus, the reduction in fiber angle and resulting increase in annulus radius is primarily due to a loss of volume within the annulus rather than a stretching of the fibers. In this case, especially, repair of the rupture with a surgical adhesive and subsequently filling of the nuclear space can result in restored disc thickness and increased tensile strength of the annulus While it may be sufficient to fill the nucleus with a fluid or quasi-fluid material, a preferred material would be introduced as a fluid and subsequently become solid under unloaded conditions. Such a material would generate a restorative force in the nucleus that would tend to return the disc to proper thickness. It is important to keep in mind that the native nucleus is not a rigid solid. Therefore, a replacement material should be deformable yet effectively communicate forces between vertebral plates. Therefore, it is important that the nuclear replacement bond to the vertebral plate surfaces and to the wall of the annulus.

Other unique features of an adhesive in situ polymerizing fluid used to restore the proper distance between vertebral plates are its ability to bond to fibers naturally found in the nucleus, which still maintain structural connection between the vertebral plates. These fibers can then act as a reinforcing element within the formed polymerized mass.

The material of this invention has all of these feature, and one additional feature of great utility. Since the hydrogel material formed contains water and is hydrophilic, the occurrence of calcification in the nuclear space is reduced. The vertebral plate surfaces are cushioned, but also are effectively protected against abrasion due to solid calcium deposits in the nuclear space.

The method of restoring proper disc thickness with an adhesive in situ polymerizing material can be used on discs that are ruptured or merely dilated. The clinical approach in treating these two distinct conditions may be quite different. For example, if the annulus is not ruptured any effort to introduce a solid into the nuclear space will likely results in a severe reduction in annulus strength. In this case, two things are needed. The nuclear material which has undergone chemical degradation, including formation of calcification deposits must be isolated from the relatively nerve-rich vertebral plate surfaces. Introduction of a thin injector or needle into the nuclear space must be capable of maneuvering to a number of locations within the nucleus since even in the degenerated state the nucleus is not porous enough to allow fluid introduced at one location to travel to other locations within the nucleus. In the preferred embodiment the injector forms a space around the perimeter of the nucleus through which the polymer solution flows and from which it diffuses into the nuclear volume. It may also be advantageous to use the same catheter, or one with greater rigidity, to form intersecting volumes which pass through the center of the nucleus. The goal is to coat any degenerated material with hydrogel to chemically and physically isolate it from nerve endings without removing it.

Alternatively, if the annulus is already ruptured, the nuclear material can be removed, and replaced by filling the space with adhesive. Then the fissure is repaired with the filling polymer solution or one of greater tensile strength. In both approaches it is possible to pressurize the nuclear replacement fluid to attain a final increased disc thickness. This may be achieved by leaving the injector in place while the polymer polymerizes, blocking loss of the fluid prior to solidification.

Alternatively, the nuclear volume could be filled without pressure, the injector removed, and a second polymerizing material used to fill the hole created by the injector. The second fluid would have a cure time substantially less than the cure time of the fluid used to fill the nuclear volume. Secondly, the filling fluid could contain substantially more functional reactive groups, such as isocyanate in the preferred adhesive, so that normal production of carbon dioxide during the polymerization is sufficient to create gaseous carbon dioxide. The repair steps are: 1) the injector is removed, 2) the hole is bonded closed, and 3) the liquid nuclear replacement, while curing, produces a volume of carbon dioxide sufficient to pressurize the nuclear volume before solidification. The resulting voids created by the carbon dioxide gas are filled with water from the body as the carbon dioxide dissolves into the body.

Disc Thickness Augmentation

In a case where the disc is degenerated to the point where adjacent vertebral plate surfaces interact pathologically, it may be sufficient to refill the annulus with an in-situ polymerizing tissue adhesive. In this instance, the cross section of the delivery route through the annulus should be minimized to prevent compromising the integrity of the annulus. The simplest route of delivery is a small gauge hypodermic needle passed into the nucleus interior through the annulus. The injection can be performed under pressure to increase disc thickness and the adhesive should be allowed to cure before retracting the needle. In the case where a low cured modulus is beneficial, for example when mimicking the natural nuclear modulus is an advantage, then injection along a bias is desired.

Figure 15:
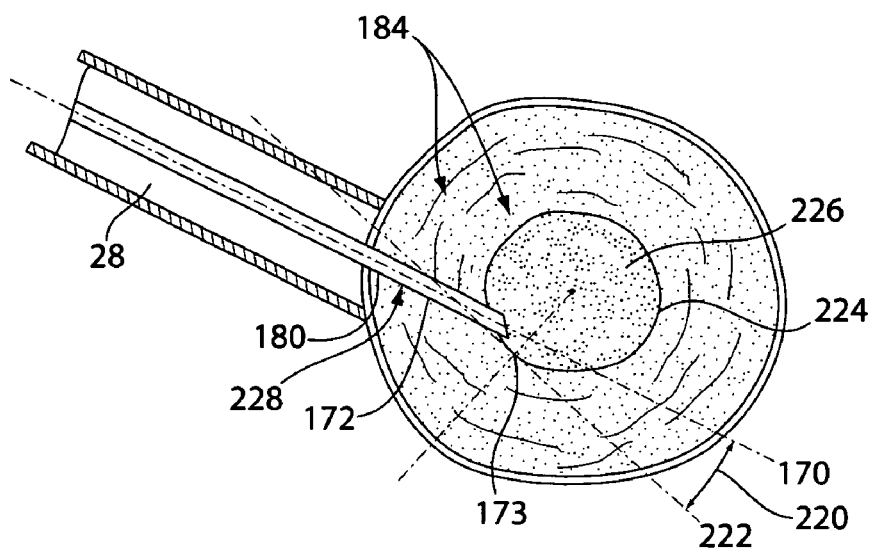
FIG. 15 is a cross-section view of a disc illustrating a needle advanced through the annulus wall.

Referring to FIGS. 13 and 15, the annulus is exposed at a site where the axis 170 of trocar 28 is slightly offset by an angle 220 from a line 222 collinear with a tangent 172 at the point of intersection 173 formed by a line 174 approximately perpendicular to trocar axis 170 that passes through disc center 176. Offset angle 220 is toward disc center 176. Intersection point 173 is on or near inner annulus surface 224. Axis 170 now defines an injection path that is long compared to an injection path that intersects disc center 176. A beveled hollow needle 180, flattened along a dimension 182 is introduced along trocar axis 170 with dimension 182 perpendicular to the plane defined by trocar axis 170 and disc bisector 174. Needle 180 is advanced through the annulus wall 178 until needle tip 182 enters nucleus 226 near intersection 173. This positioning can be achieved by estimation or fluoroscopy. This action causes needle 180 to cut through layers 184 of the annulus creating needle track 228.

Now using the set-up of FIG. 14, beveled hollow needle 180 with proximal end 194 with luer fitting 196 is attached to adhesive syringe 198. Subsequently, pressure is applied to plunger 206 of adhesive syringe 198 and a desired volume of adhesive is dispensed. If the adhesive is dispensed under pressure then when needle 180 is removed from needle track 228, the needle track will collapse behind the needle tip 182 as it is removed. Under this condition, even a very low modulus cured nuclear implant will be blocked from extrusion out needle track 228.

Figure 16A:
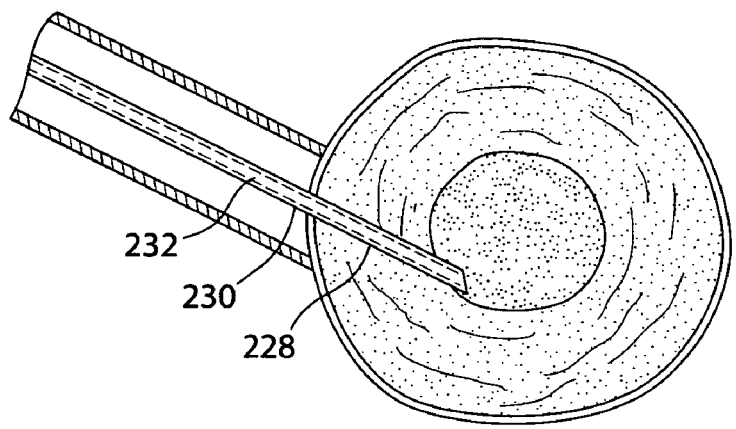
FIG. 16 is a cross-section view illustrating catheter delivery of the adhesive, with FIG. 16A showing placement of a catheter and FIG. 16B showing placement of an adhesive.
Figure 16B:
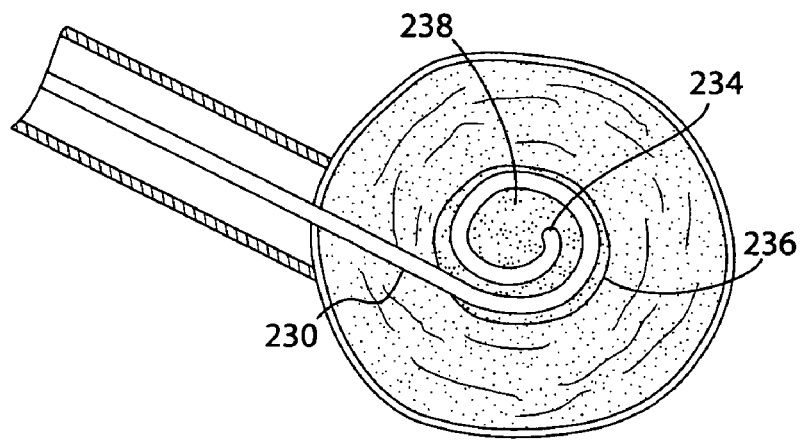

Referring to FIG. 16, the above approach may be particularly beneficial when the nucleus is degraded and comprised of fluids and loose particulate. In this case, instead of needle 180, flexible catheter 230 is used with stylet 232. Catheter 230 and stylet 232 form needle track 228, then stylet 232 is removed and catheter 230 is advanced into the nucleus. Blunt tip 234 causes catheter 230 to follow inner annulus wall 236 coiling around in the nucleus 238. This action further disaggregates the nucleus. The nuclear volume 238 may be substantially filled with catheter 230. During nuclear disaggregation suction may be applied to catheter 230 proximally to aspirate part or all of disaggregated nucleus 238. Then adhesive may be delivered through catheter 230 to nuclear volume 238 to bond together disaggregated nuclear parts and fill volume 238. Catheter 230 may be removed in synchrony with filling. Alternatively, adhesive may be injected into nuclear volume 238, mixed with disaggregated nuclear parts and subsequently aspirated one or more times. Each time the aspirated volume is replaced with fresh adhesive.

Figure 17A:
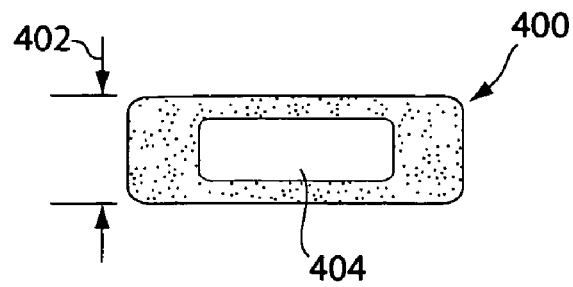
FIG. 17A shows disc height after the first application and FIG. 17B shows disc height after the second injection.
Figure 17B:
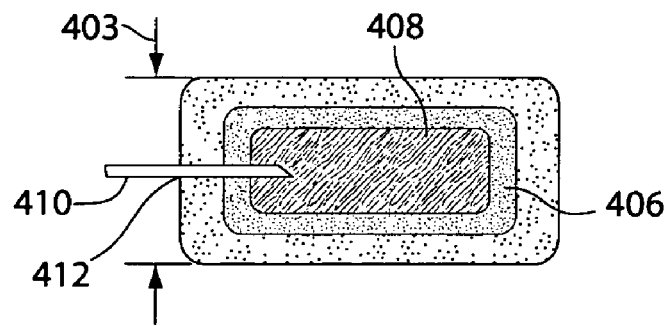

Referring now to FIG. 17, other methods of restoring a disc 400 to its proper thickness 403 (FIG. 17B) include removal of the nucleus 404 and subsequent mechanical expansion of the disc thickness 402. This can be accomplished with a first adhesive that substantially or completely polymerizes to make in-situ formed elastic volume 406 which is subsequently filled and pressurized with a second in-situ polymerizing substance 408. Preferably, the cure time of the first adhesive is much faster than the cure time of the second adhesive.

Using any of the above described techniques, access is made to the nucleus and all or part of the nucleus is removed. Catheter 410 is introduced into the nuclear space 404 and first adhesive is injected under light pressure. First adhesive polymerizes filling nuclear space 404 and sealing catheter 410 to annulus wall 412 with in-situ formed elastic volume 406. The injection is performed such that catheter tip 414 is completely surround by volume 406, and preferably is at the center of 406. After volume 406 is completely cured, second adhesive 408 is introduced into volume 406. Volume 406 encapsulates second adhesive 408 and expands around it. This action increases disc thickness 402. Once proper disc thickness 402 is achieved, the volume is allowed to polymerize to allow for catheter removal. This approach is particularly useful in a posterior lateral approach where a laminectomy is performed.

Figure 18:
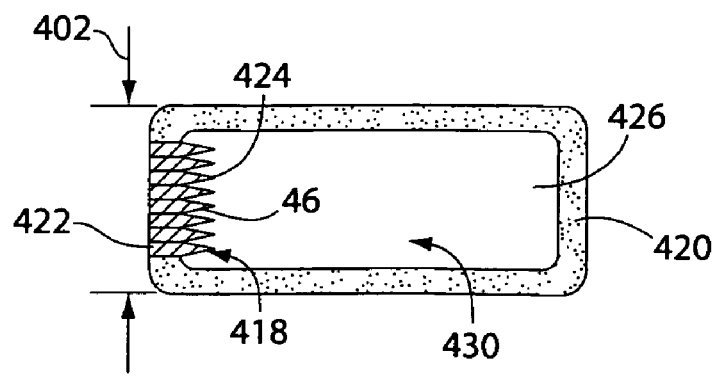
FIG. 18 illustrates the use of jacks or wedges to increase disc height prior to or during delivery of the adhesive.

Alternatively, disc thickness 402 can be improved by "jacking" the disc space using successively applied tapers 416. Referring to FIG. 18, access 418 is made through annulus 420. A taper 416 is selected and passed through access 418. Taper 416 has a cross section wherein primary axis 422 is larger than secondary axis 424 and secondary axis 424 is aligned with the disc plane 426. The secondary axis 424 decreases toward distal end 428 of taper 416 while primary axis 422 is unchanged. Multiple tapers may be stacked such that their primary axes add to increase disc thickness 402. When the proper disc thickness 402 is achieved, adhesive is delivered to the nucleus interior 430. After a substantial volume of the nucleus interior 430 is filled and polymerized, then the tapers can be removed and the remaining volume filled.

Prosthetic Immobilization

One embodiment of the present invention provides a method and apparatus for treating intervertebral disc disorders, particularly localization and fitting of a nucleus prosthetic, which may or may not be accompanied with sealing of the access window in the annulus and subsequent pressurization. The invention comprises coupling a tissue polymerizing agent with a guidable intervertebral disc apparatus or injector, as described above, and using this combination for accessing and delivering an in situ polymerizing agent at a location in an intervertebral disc having 1) a nucleus prosthetic inserted in the space formerly occupied by the disc nucleus and 2) at least part of the annulus fibrosus, the annulus having an inner wall.

The invention is distinguished from conventional percutaneous interventions in not being reliant on reference measurements and selection of appropriate prosthetic sizes. Such conventional approaches are further complicated by insufficient range of available prosthetic sizes, typically only one. Additionally, the present invention can be used with any insertional apparatus that provides proximity to the disc, including many such insertional apparatuses known in the art as an "introducer". An introducer, as described above, has an internal lumen with a distal opening at a terminus of the introducer to allow insertion/manipulation of the operational parts into the interior of a disc.

The method starts with a standard discectomy, where a window is formed in the annulus sufficient to accept the nucleus prosthetic and part or all of the nucleus is removed. Then the replacement nucleus is inserted into and centered in the cleared area of the disc. Then the guidable intervertebral injector apparatus is connected to a source of polymer solution. The tip of the device is introduced into the nuclear space through the window and guided through the space between prosthetic and natural disc annulus to a location approximately 180 degrees from the entrance point. In this way the dispensed solution fills toward the entrance point. The solution is injected until just filling the annulus opening. Then the device is slowly removed, and care is taken to dispense additional fluid to fill the space evacuated by the dispensing tip. Once the injector is removed, the location of the prosthetic can be adjusted and held in place until the polymer solution become sufficiently viscous to prevent prosthetic dislocation. The remaining void between the prosthetic and annulus exterior surface can be filled with additional polymer solution and allowed to cure. After the prosthetic nucleus is immobilized, the same polymer solution, or a solution with higher tensile strength and optionally with reinforcing fillers such as fibers, is injected to fill the window opening made in the annulus. If there is a significant fissure in the annulus through which the disk initially bulged, it can be filled with a high tensile reinforcing solution first, and then the rest of the space is filled as just described.

The prepolymer can be used without addition of an aqueous solution to prevent polymerization within the delivery device. In the case where an aqueous solution is mixed with the prepolymer, a second syringe (or other source) containing polymer solution will be needed to perform the topping off part of the procedure. If the prosthetic is sufficiently immobilized, the topping off step can be accomplished as the device is being removed and before polymerization.

In the case where a radio-opaque agent is added to provide visualization of the procedure during fluoroscopy, it may be beneficial to orient the fluoroscope such that the position of the annulus, prosthetic and polymer solution allow one to monitor movement of the prosthetic during delivery of the solution.

Nuclear Prosthetic Localization

Referring to FIG. 19, using any of the above described techniques, access is made to the nucleus and all or part of the nucleus is removed. Trocar 432 makes a sealed connection 434 with annulus surface 436. In FIG 19a (upper left), nucleus prosthetic 438 is introduced down trocar 432 using detachable driver 444 and passed through annulus opening 440 into nuclear space 442. In FIG. 19b (upper right), the nuclear prosthetic 438 is held by driver 444 at the center of nuclear space 442. Next, (FIG. 19c, lower left), flexible catheter 446 is introduced around driver 444 and into nuclear space 442. Adhesive 448 is delivered to nuclear space 442, such that adhesive flows around prosthetic 438 as described by path 450. Driver 444 is removed and catheter 446 is retracted to a position outside the disc and within trocar 432. Then a second application of adhesive is delivered. The result, shown in FIG. 19d, lower right, is that the nuclear space 442, annulus opening 440 and a small portion 452 of trocar 432 are filled with cured adhesive 448. Subsequently planer 454 is introduced inside of trocar 432. The outer dimension of planer 454 matches the inner dimension of trocar 432. Planer 454 has a screw-like cross section 456. The distal end 458 of planer 454 has a flat profile with slightly raised cutting blades 460 such that when planer 454 is turned about its axis 462 a smooth planed surface is formed and trimmings are forced proximally along screw-like surfaces of planer 454. As the planer is advanced distally, the planer first planes through the layer 452 providing very little resistance. When planer tip 458 engages annulus opening 440 resistance to turning planer 454 about its axis 462 increases noticeably. After this point a further full turn is performed to yield a flat surface.

Alternatively, it is contemplated that a first application of material, which may or may not be adhesive, is made to partially fill the disc nucleus space and then the adhesive is applied as described above to secure the in-situ formed implant in place and close the opening in the annulus. It is further contemplated that the implant may be formed in-situ by providing a balloon delivered inside the disc nucleus and filling the balloon with a suitable implant forming material. The balloon containing the implant formed therein may optionally then be secured in place by delivering adhesive to surround the implant and adhere to the surrounding annulus.

As described above, it is believed the ability of the fluid adhesive to penetrate the interstices of the fibrous annulus wall will substantially increase the ability to secure a disc nucleus implant in the proper position and substantially reduce if not eliminate post-surgical movement or expulsion of the disc implant.

Annulus Defect Repair

Figure 20:
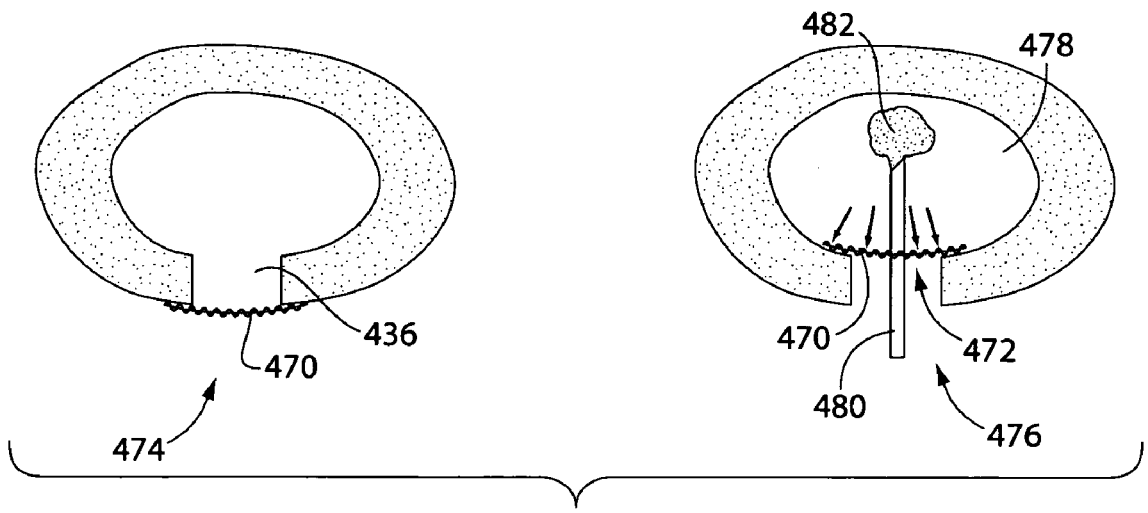
FIG. 20 illustrates in cross-section the repair of an annulus opening by gluing a mesh over the opening.

When access to the nuclear space requires a large window be cut from the annulus, such as in delivery of a nucleus prosthetic, it may be beneficial to reinforce closure of the annulus opening with mesh coupled with adhesive. Referring now to FIG. 20, mesh 470 may be positioned outside the annulus opening 472 as in configuration 474 or inside the annulus opening 472 as in configuration 476. When configuration 476 is used, pressure within the nucleus 478 may help seal mesh 470 to annulus opening 472. In this situation, mesh 470 may have minimal porosity to provide filling through the mesh without leakage. For example, mesh 470 is placed behind annulus opening 472. Hypodermic needle 480 pierces mesh 470 and delivers adhesive 482 behind mesh 470. Adhesive 482 causes mesh 470 to seal against annulus opening 472. When configuration 474 is used, repair of the nucleus is performed, then subsequently mesh 470 is laid over the opening and saturated with adhesive. In this case, mesh 470 is preferably porous.

It is also contemplated that a balloon may be filled inside the nucleus to hold the mesh in place as the adhesive holding the mesh in place cures. The balloon may be removed or may be left in place, and may be filled with adhesive if left in place inside the nucleus.

Figure 21:
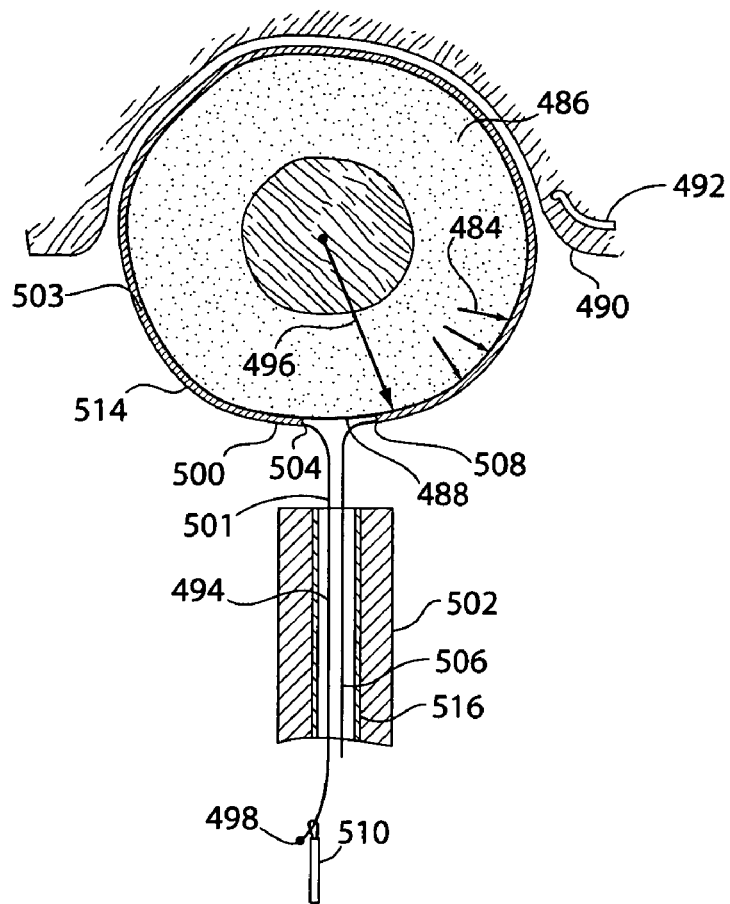
FIG. 21 illustrates dissection and repair of an annulus defect without treatment of the disc nucleus.

Referring now to FIG. 21, in some cases the annulus defect is pre-existing. In this case the treatment may consist only in repairing the defect without manipulation of the nucleus. The goal may be to seal the defect and to additionally constrain the outward bulge 484 of the annulus 486. A surface 488 of the annulus 486 is exposed. Tissue is dissected away from annulus 486 at sites 490 as much as possible. Vessels and nerves 492 on the caudal site are gently retracted away from the annulus surface 488. A dissecting ribbon or wire 494 is introduced at annulus surface 488. Dissecting ribbon 494 is stiff with preformed radius of curvature 496 which approximately matches the radius of annulus surface 488. When ribbon 494 is advanced along annulus surface 488 radius of curvature 496 forces blunt tip 498 to stay close to annulus surface 488 as it circumnavigates the annulus 486. Ribbon 494 is advanced until blunt tip 498 emerges on the other side 500 of annulus 486 and is advanced into trocar 502.

The proximal end 501 of ribbon 494 is attached to first end 504 of mesh 503, and an additional length of ribbon or wire 506 is attached to second mesh end 508. Loop snare 510 is placed into trocar 502 and blunt tip 498 is engaged. Loop snare 510 is pulled advancing mesh 508 to annulus surface 488. A flexible catheter, not illustrated (but similar to FIG. 14), is placed into trocar 502 and adhesive 514 is delivered to mesh 503. The flexible catheter is removed and mesh 503 is advanced around annulus 486 by further pulling on snare 510 a distance equal to the length of mesh 503. Mesh ends 504 and 508 are now exposed on opposite sides of annulus 486. Hollow tube 516 is placed over blunt end 498 of ribbon 494 and wire 506 to form a snare. When hollow tube 516 is introduced down trocar 502 while placing tension on blunt end 498 and wire 506 tension is placed on mesh 503 and ends 504 and 508 are brought together. Disc bulge 484 is controllably reduced by this configuration and held until the adhesive hardens. After the adhesive hardens, mesh end 504 is trimmed from ribbon 494 and mesh end 508 is trimmed from wire 506. The free mesh ends 504 and 508 are overlapped and bonded together with an additional application of adhesive.

It is possible to repair an annulus defect by coring the defect and filling the resulting channel with avascular tissue harvested from the patient at another site. In this case, the harvested core of tissue is placed in the defect channel and bonded to the walls of the channel. Bonding can be accomplished by coating the core with adhesive before placing in the defect channel or secondarily paving over the core placed in the defect channel with mesh soaked with adhesive, or adhesive alone.

Sealing of a Fissure in the Annulus

In many cases, the proximate cause of a disc repair operation is the formation of a fissure in the annulus, often accompanied by protrusion of the nucleus into and/or outside the annulus. Such fissures in the annulus are most problematic when they are in the posterior medial segment of the annulus, next to the spinal cord. Repair of such lesions via the lateral posterior route has been very difficult with prior art methods.

Figure 22:
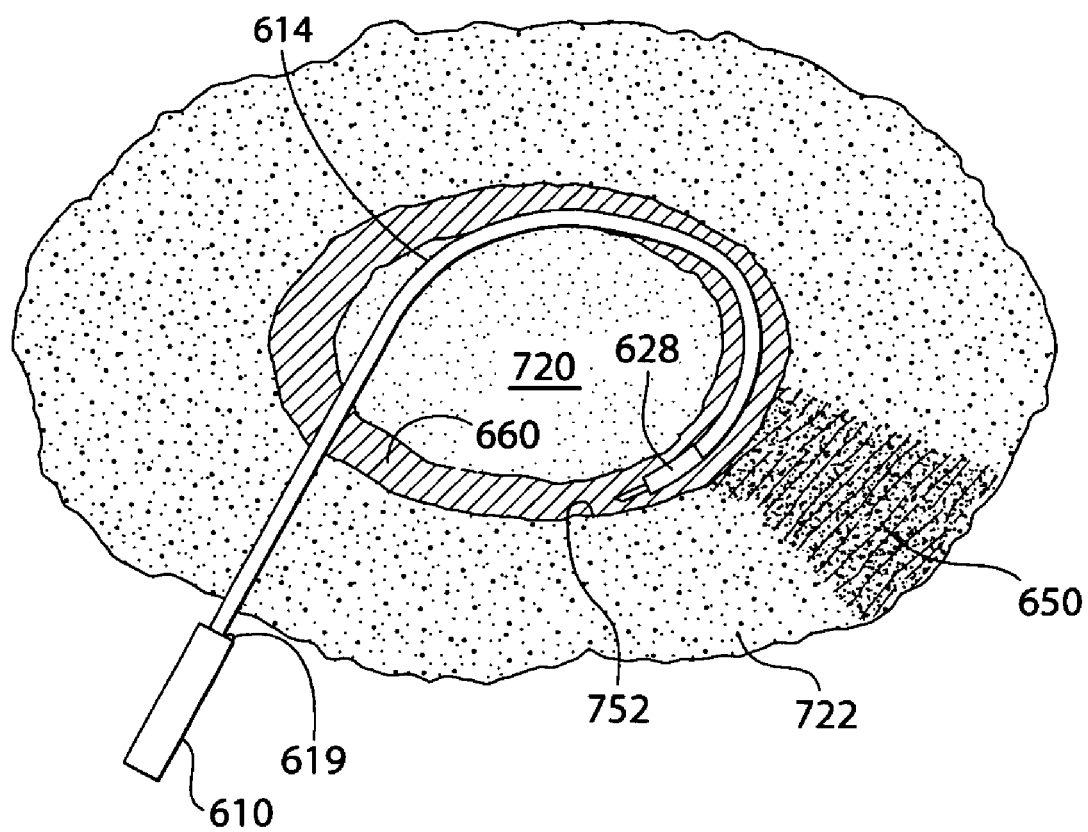
FIG. 22 illustrates repair of a fissure in the annulus.

In a method of the invention, the fissure defect is repaired in a simple, minimally invasive manner. Referring to FIG. 22, first, an introducer as in FIG. 2 is placed in the triangle by standard methods. To the extent possible, the introducer 612 is placed so that its tip 621 is positioned just inside the annular wall, without penetrating deeply into the relatively fluid nucleus. An injector 610 is inserted through the introducer. A tip 628 for the tubular portion of the injector is selected that has a relatively blunt, non-penetrating tip. The injector is rotated so that the tube 614 tends to curl towards the annulus. This prevents the tube from simply penetrating into the nucleus as it is introduced. The tube 614 of the injector is then slowly extended into the disc, generally following the inner wall of the annulus, until it reaches the fissure 650. The tip tends to angle into the fissure 650, since it is not supported by the annulus wall 752. This deviation can be detected by several methods, including observation through a fiber, or by fluoroscopy or ultrasound, or by a decrease in force required for insertion. Then, if not done previously, the injector is connected with a source 615 of a self-polymerizing adhesive solution, and the solution is injected into the fissure 650. Filling is monitored by visualization, ultrasound, fluoroscopy or other technique. The injector may be rotated 90 degrees to provide filling in the caudal or sacral directions. Next, the injector is reoriented if required, and retracted along the route of entry. Adhesive may be injected during withdrawal to fill the space created by entry, if required. The adhesive bonds to the walls of the fissure and cures in situ, bonding the surfaces of the fissure together via a resilient body of self-crosslinked adhesive.

For such an application, a relatively short cure time is preferable, to prevent migration of adhesive towards the spinal cord. The degree of hydration of the adhesive should be minimal, to attain maximum cured modulus and prevent bulging of the repair site. The use of additives fibers and other reinforcing materials providing resistance to tearing is potentially beneficial.

Encapsulated Nucleus Replacement

An encapsulating skin is useful to isolate tissue from an uncured polymer solution, especially if the cure time is long. An encapsulating skin can act as a restraining force, increasing the effective modulus of the formed implant. Such a skin can further generate an internal pressure in the hydrogel if the skin is formed before appreciable carbon dioxide is released due to polymerization of the bulk volume of the polymer solution. Alternatively, the skin can generate increased pressure when addition amounts of polymer solution or aqueous solution are added.

Such a skin can reinforce a failing annulus, prevent leakage prior to polymerization during injection into the nucleus, and be used to generate an internal pressure sufficient to increase the intervertebral distance. When the modulus of the skin is more than the modulus of the internally polymerized hydrogel, then the skin hydrogel system can be tailored to approximate the functional structure of the nucleus/annulus system, or disc.

Such a skin can be made by using the adhesive materials of the invention to pre-treat tissue or to pre-coat a surface of a void, for example from removal of a nucleus, intended to be filled later with the polymer solution. The adhesives act to form a skin on the tissue solution before the bulk volume of the polymer solution is inserted, or before it begins to gel. This skin is fully encapsulating and acts as a restraining force. Depending on the type of agent used, this skin can be made hard or elastic.

To achieve the skin effect, it is helpful if the polymer on the tissue surface can polymerize faster than the bulk polymer. There are various catalysts and crosslinking agents that can be used to accelerate the polymerization reaction. The catalysts include salts of tin. The crosslinking agents include free isocyanates, difunctional amines and various amino groups, e.g., lysine. Such materials, and/or other accelerants of polymerization, can be applied to tissue before applying the bulk polymeric solution. Methods of application of the faster curing fraction include spraying or painting directly to tissue, before or concurrently with application of the polymerizable adhesive material.

Nucleus Replacement

The present invention may be useful in polymerizing and enhancing the integrity of tissue-derived gels, for example derived from components of the nucleus, which may be present in the intervertebral space. Such gels, when infused with the adhesive of the present invention, become substantially more rigid and do not flow. This feature is also important in binding chemicals produced in a diseased disc, to prevent them from migrating to nerves and stimulating pain. The polymerization is not limited to the gel bulk, but may serve to elastically fix and structurally enhance the attachment of the endogenous gel to tissue and bone.

The polymerization and adjacent bonding does not require the polymerizing material to be delivered directly to the target site. When the solubility of the polymer is high and the cure time is long the adhesive prepolymer will diffuse throughout the nuclear space and become well mixed with the endogenous tissue before fixation.

Additionally, the material of the present invention may be mixed with any of the following to create a tissue bonding solid mass in situ: bone, metallic particulate, hydroxylapatite, carbon spheres, precipitating polymer solutions such as EVOH and DMSO.

Moreover, the material of the present invention may be placed in the nucleus of the disc under pressure to increase, or return to an appropriate distance, the spacing between vertebral bodies. The liquid polymer solution under pressure is capable of solidifying while the injector is in place. The injector can then easily be removed once the polymer is solid, thus providing a self-sealing nucleus replacement and/or augmentation therapy without compromising the integrity of the annulus. These nucleus augmentation methods can also be performed after a discectomy. The polymer hydrogel formed within the nucleus substitutes for the natural nucleus.

Generally, nucleus replacement devices need to be localized within the nucleus of the disc to prevent impinging on the spinal cord or associated branched nerves. The degree of localization determines the modulus requirements of the implant. For example, when a large window is made in the annulus for introducing a nucleus replacement device, the replacement device must have a high modulus, typically greater than 6000 psi, to prevent extrusion of the device through the large opening in the annulus. These high modulus devices essentially replace the functionality of the entire disc. If in other cases, the opening in the annulus is small compared to the nuclear space or can be closed after insertion of the replacement device, the annulus plays a role in supporting the disk thickness. Essentially, forces applied along the axis of the spine which tend to compress the nucleus are translated to the wall of the annulus in much the same way pressure applied to the gas in a tire is supported by the tire wall. As in the instance of the tire, the filling medium can have a low modulus. The basic requirement of a successful nucleus replacement device is that its modulus be large enough that the pressure required to extrude the implant through the opening in the annulus is greater than the pressure required to dilate the opening in the annulus. This assumes, of course, that the nucleus replacement device is substantially larger than the opening in the annulus.

Thus, there are three conditions that may be present in nucleus replacement: 1) the nuclear replacement device is smaller than the opening in the annulus and thus must be localized by a tissue bond or a post-implant dilation of the device and must possess a very high modulus, typically greater than 1000 psi; 2) the nuclear replacement device is larger than the opening in the annulus and the modulus of the device is moderate such that the pressure required to extrude the device through the opening exceeds the pressure to dilate the opening, and 3) the opening in the annulus is either closed or very small and the modulus of the device can be arbitrarily small.

Consequently, a replacement device can span a broad range of moduli. Factors that reduce modulus and enhance flexibility of the spine include: 1) bonding the implant to the vertebral plates, 2) maximizing the implant volume relative to the opening in the annulus, and 3) minimizing and/or post-operatively repairing the opening in the annulus. It is clear that a liquid tissue adhesive that forms a solid flexible implant is an ideal nucleus replacement device, or an important adjunct to the use of a pre-formed nucleus replacement device.

In some cases a large defect in the annulus is already present. In this case there are high modulus pillow-like implants available on the market that are substantially disc replacement devices. These high modulus devices must be smaller than the annulus opening to be successfully implanted. Some expand after implantation, but do not expand rapidly enough to prevent movement of the implant within the nuclear space causing pain. Consequently, there is a need for a space filling liquid polymer that can act to fill a void within the implant/nucleus combination that bonds the implant within the disc. Additionally, it is advantageous to have the polymer liquid bond to the implant to prevent extrusion of the space-filling polymer. These objectives can be met by injecting a suitable amount of the adhesive polymer solution of the invention, and if required maintaining the position of the prosthetic until the adhesive has cured. It is also possible to use a balloon, for example carried on a catheter or similar device, to shape or expand the nuclear space. A deflated balloon is positioned inside the annulus, and then it is inflated Other Features The present invention is intended to replace or augment traditional functional elements including: energy delivery to shrink or modify tissue, means for delivering material, use of sealants to seal tissue, insertion of solid replacement parts. The present invention may be incorporated with or delivered in addition to electrolytic solutions (such as saline), contrast media (such as Conray meglumine iothalamate, or tantalum powder), pharmaceutical agents, disinfectants, filling or binding material, or chemonucleolytic agents.

A variety of materials can be delivered to the fissure, including but not limited to electrolyte solutions, contrast media, pharmaceutical agents (such as the steroid methylprednisolone sodium succinate available from Pharmacia & Upjohn, Kalamazoo, Mich., nonsteroidal anti-inflammatory drugs and/or pair medications), chemonucleolytic enzyme (e.g. chymopapain), alternative or biological hydrogels (such as disclosed in U.S. Pat. No. 4,478,822), osteoinductive substances (e.g. BMP, see U.S. Pat. No. 5,364,839), chrondrocyte inductive substance (e.g. TGG-beta). The materials may be administered sequentially or simultaneously, such as beginning with an electrolyte (which aids in viewing), then following with products to effect a desired healing outcome. These materials are to be mixed with the polymer solution such that when it solidified or polymerizes, the materials are incorporated into the resulting hydrogel matrix and are available to act therapeutically.

In particular, the present invention may be useful in polymerizing and enhancing the integrity of gels present in the intervertebral space. Such gels, infused with the adhesive of the present invention, become substantially more rigid and do not flow. This feature is important in binding chemicals produced in a diseased disc to prevent them from migrating to nerves an affecting pain. The polymerization is not limited to the gel bulk, but serves to elastically fix and structurally enhance the endogenous gel to tissue and bone. The polymerization and adjacent bonding does not require the polymerizing material to be delivered directly to the target site. When the solubility of the polymer is high and the cure time is long the gel will become well mixed with the polymerizing material before fixation.

The method of the present invention may include the use of a mesh or absorbent biocompatible material to be inserted in a compressed or rolled state in the access hole and released into a cavity or space made in the nucleus pulposus. The cavity will be of sufficient size to allow the mesh to be opened, and will have at least one wall of the cavity located at the transition between annulus and nucleus such that the mesh can be placed planar to this transition. Subsequently, an injector is introduced through or around the mesh, so that polymer solution can be delivered through or behind the mesh and is allowed to cure. When the cavity is later filled and cured, the resulting fluid pressure is confined by the mesh. Subsequently, the cured polymer both seals the absorbent mesh and bonds it into place such that the implant volume is constrained.

The material of the present invention may be mixed with fibers, for example flock, to increase its tear resistance after polymerization without increasing prohibitively, the injectability of the solution. Additionally, selecting solutions with a higher proportion of polymerizing agent to aqueous solution creates a more rigid gel. Typically, the gel modulus can be controlled from a very loose gel to one of 50D Shore or greater. The material of the present invention may be used in conjunction with other disc therapies, including but not limited to disc replacement implants, cages and bone cements.

Additionally, the material of the present invention may be mixed with any of a number of materials to create a tissue bonding solid mass in-situ, including without limitation bone and bone particles, metallic particulate, hydroxylapatite, carbon spheres, and precipitating polymer solutions such as EVOH in DMSO.

While each of the components of the invention could be provided separately, it will generally be preferred to combine the elements of the invention into a kit for performing a particular spinal operation. The kit will contain the correct amount of surgical adhesive for the procedure. In addition, the kit will contain, in sterile form, the particular devices needed for the procedure. These will be selected from introducers, catheters, corers, wires, meshes, etc, as required for the particular procedure. Typically there will at least be an introducer or trocar, and a delivery device for the adhesive such as a syringe or catheter. In addition, the kit will typically contain or be provided in association with a set of directions for using the components to perform the procedure. As can be seen from examples above, the procedure can be quite complex; even with training, a detailed set of directions is desirable and potentially important.

While examples have been provided to illustrate the invention, its scope is not to be limited by the description or its examples, but only by the appended claims.

The invention claimed is:

1. A method of reinforcing a spinal annulus, the method comprising the steps of:
    creating an access opening in the annulus to be reinforced;
    providing a catheter through the access opening;
    introducing a wire or ribbon through the catheter, or deploying a balloon on the tip of the catheter, to create at least one of a pocket, a cavity, and a delamination within the annulus, wherein said at least one of a pocket, a cavity, and a delamination extends substantially circumferentially and solely within two or more layers of the annulus between the innermost annular surface adjacent to the nucleus, and the outermost annular surface;
    extending the pocket, cavity or delamination to at least partially circumnavigate the annulus;
    removing the wire, ribbon or balloon;
    introducing, through the same or another catheter, an injector for delivering a tissue adhesive composition that is reactive with functional groups normally found on tissue surfaces so as to bond to tissue;
    injecting a controlled amount of said tissue adhesive;
    gradually withdrawing the injector while filling the pocket, cavity or delamination with said tissue adhesive to bind the two or more layers of the annulus with the tissue adhesive; and
    allowing the tissue adhesive to cure to form a hydrophilic implant adherent to at least one tissue surface in the region of the circumferentially-extending pocket, cavity or delamination, thereby repairing at least a part of the defect; wherein the tissue adhesive composition comprises branched polyether polyols with polyisocyanate caps, and wherein the polyether polyol comprises a copolymer of ethylene oxide and propylene oxide containing at least about 70% ethylene oxide.

2. The method of claim 1, wherein the tissue adhesive is characterized in being hydrophilic; and in being capable of self-curing in the presence of water, optionally in the absence of added reactive materials or chain extenders, to form a solid material adherent to at least one tissue surface.

3. The method of claim 1 wherein the injector is bendable.

4. The method of claim 3 wherein the injector is selectable for penetration of tissue or for sliding on a fissure plane.

5. The method of claim 1 wherein multiple injections of adhesive polymer are performed.

6. The method of claim 5 wherein the injector is moved between injections.

7. The method of claim 1 wherein the curable tissue adhesive is naturally liquid at room or body temperature.

8. The method of claim 1 wherein the tissue adhesive contains water or an aqueous solution in the range of about 5% to about 95% by volume.

9. The method of claim 1 wherein the cured tissue adhesive swells in body fluids.

10. The method of claim 1 wherein the tissue adhesive comprises a water-soluble polyether polyol.

11. The method of claim 1 wherein the tissue adhesive also contains a polyreactive material with a molecular weight less than about 1000 Daltons.

12. The method of claim 1 wherein the curable tissue adhesive is curable via the reaction of a reactive group, which reactive group is isocyanate or isothiocyanate.

13. The method of claim 1 wherein the tissue adhesive composition comprises branched polyether polyols with polyisocyanate caps and excess polyisocyanate.

14. The method of claim 1 wherein the injector further comprises visualization means.

15. The method of claim 1 wherein the injector detects pressure.

16. The method of claim 1 wherein the tissue adhesive composition comprises one or more of contrast or visualization media, electrolytes, volume-control polymers, fillers or reinforcing materials, pharmaceutical or therapeutic agents including disinfectants, and nucleolytic agents including enzymes and chemicals.

17. The method of claim 1 wherein the tissue adhesive implanted within the two or more layers of the annulus is mixed with between about 5% and about 95% by volume of water or aqueous solution.

18. The method of claim 1 wherein the tissue adhesive implanted within the two or more layers of the annulus is tissue adhesive mixed with a small proportional amount of water or aqueous solution so as to have a high tensile bond.

19. The method of claim 1 wherein the tissue adhesive contains a radio opaque inert filler.

20. The method of claim 1 wherein the delivery of tissue adhesive is performed under pressure.

21. The method of claim 1 wherein the formed hydrophilic implant contains a radio opaque material.

22. The method of claim 1 wherein the tissue adhesive is injected and allowed to cure before removal of the introducer and injector.

23. The method of claim 1, wherein the tissue adhesive is characterized in being hydrophilic; reactive with functional groups normally found on tissue surfaces so as to bond to tissue; and capable of self-curing in the presence of water, optionally in the absence of added reactive materials or chain extenders, to form a solid material adherent to at least one tissue surface.

24. The method of claim 1 wherein the tissue adhesive, before any addition of water or aqueous solution, consists essentially of a water-soluble polyether polyol capped with isocyanate groups, and excess low molecular weight polyisocyanate.

25. The method of claim 1, wherein the step of allowing the adhesive to cure further comprises allowing the adhesive to adhere to at least one tissue surface.

26. The method of claim 1, wherein the curable adhesive is characterized in being hydrophilic; reactive with functional groups normally found on tissue surfaces so as to bond to tissue; and capable of self-curing in the presence of water, optionally in the absence of added reactive materials or chain extenders, to form a solid material adherent to at least one tissue surface.

27. The method of claim 1, further comprising the steps of:

inserting an introducer into the pocket, cavity, or delamination within the two or more layers of the annulus fibrosus;

inserting an injector through the introducer; and injecting a controlled amount of the curable polymeric composition, wherein the curable polymeric composition repairs a part of the pocket, cavity, or delamination by adhering to tissue during curing.

28. The method of claim 1, wherein the tissue adhesive comprises one or more of contrast or visualization media, electrolytes, volume-control polymers, fillers or reinforcing materials, pharmaceutical or therapeutic agents including disinfectants, and nucleolytic agents including enzymes and chemicals.

29. The method of claim 1, further comprising a step wherein the injector or an ancillary device is used to create the pocket, cavity, or delamination within the two or more layers of the annulus, and then the pocket, cavity or delaminated area is filled with the adhesive.

30. The method of claim 1 wherein the step of injecting further comprises delivery of said curable polymeric tissue adhesive under pressure, so as to cause said adhesive to do at least one of penetrate into the layers of the annulus, and fill defects in the annulus.

* * * * *

UNITED STATES PATENT AND TRADEMARK OFFICE
CERTIFICATE OF CORRECTION

PATENT NO. : 7,632,294 B2 Page 1 of 1
APPLICATION NO. : 10/873899
DATED : December 15, 2009
INVENTOR(S) : Michael T. Milbocker et al.

It is certified that error appears in the above-identified patent and that said Letters Patent is hereby corrected as shown below:

On the Title page, item (12), delete "Milbodker" and insert therefor -- Milbocker --; and item (75), delete "Milbodker" and insert therefor -- Milbocker --.

Signed and Sealed this

Sixteenth Day of February, 2010

David J. Kappos
*Director of the United States Patent and Trademark Office*